US012642802B2

(12) United States Patent
Modepalli et al.

(10) Patent No.: US 12,642,802 B2
(45) Date of Patent: *Jun. 2, 2026

(54) TOPICAL FORMULATIONS OF RUXOLITINIB WITH AN ORGANIC AMINE pH ADJUSTING AGENT FOR TREATMENT OF SKIN DISEASES

(71) Applicant: INCYTE CORPORATION, Wilmington, DE (US)

(72) Inventors: Naresh Modepalli, Wilmington, DE (US); Trupti Sheth, Wilmington, DE (US); Marc Brown, Guildford (GB); Charles Evans, Guildford (GB); James Fidge, Guildford (GB); Florencia Guidali, Guildford (GB); Tecashanell McIntosh, Guildford (GB); Vanessa Cofre, Guildford (GB)

(73) Assignee: Incyte Corporation, Wilmington, DE (US)

( * ) Notice: Subject to any disclaimer, the term of this patent is extended or adjusted under 35 U.S.C. 154(b) by 601 days.

This patent is subject to a terminal disclaimer.

(21) Appl. No.: 18/061,467

(22) Filed: Dec. 4, 2022

(65) Prior Publication Data

US 2023/0172937 A1    Jun. 8, 2023

Related U.S. Application Data

(63) Continuation-in-part of application No. 17/541,601, filed on Dec. 3, 2021, now Pat. No. 12,005,067.

(60) Provisional application No. 63/365,973, filed on Jun. 7, 2022.

(51) Int. Cl.
| | |
|---|---|
| *A61K 31/519* | (2006.01) |
| *A61K 9/00* | (2006.01) |
| *A61K 9/06* | (2006.01) |
| *A61K 9/12* | (2006.01) |
| *A61K 47/10* | (2017.01) |
| *A61K 47/18* | (2017.01) |

(52) U.S. Cl.
CPC .......... *A61K 31/519* (2013.01); *A61K 9/0014* (2013.01); *A61K 9/06* (2013.01); *A61K 9/124* (2013.01); *A61K 47/10* (2013.01); *A61K 47/186* (2013.01)

(58) Field of Classification Search
CPC .... A61K 31/519; A61K 47/10; A61K 47/186; A61K 9/06; A61K 9/0014; A61K 9/124
See application file for complete search history.

(56) References Cited

U.S. PATENT DOCUMENTS

| | | | | |
|---|---|---|---|---|
| 8,722,693 B2 * | 5/2014 | Rodgers | ................. | A61P 37/08 544/280 |
| 9,034,881 B2 | 5/2015 | Magilavy | | |

| | | | | |
|---|---|---|---|---|
| 2020/0063188 A1 | 2/2020 | Howell et al. | | |
| 2021/0113566 A1 | 4/2021 | Smith et al. | | |
| 2025/0249009 A1 * | 8/2025 | Modepalli | ............ | A61K 9/0014 |

FOREIGN PATENT DOCUMENTS

| | | |
|---|---|---|
| WO | 2000/064450 A1 | 11/2000 |
| WO | 2004/054588 A1 | 7/2004 |
| WO | 2016/198663 A1 | 12/2016 |
| WO | 2019/191679 A1 | 10/2019 |
| WO | 2020/222187 A1 | 11/2020 |
| WO | 2022/038365 A1 | 2/2022 |
| WO | 2022120131 A1 | 6/2022 |

OTHER PUBLICATIONS

LeQuang JA, Updates on psoriasis and cutaneous oncology: proceedings from the 2017 MauiDerm meeting, J Clin Aesthet Dermatol., 2017, 10(9 Suppl):S8-S41.

Dyring-Anderesen et al., "The Vitamin D Analogue Calcipotriol Reduces the Frequency of CD8+IL-17+ T Cells in Psoriasis Lesions," Human Immunology, 2015, pp. 84-91.

Lim et al., "Synergistic anticancer effects of ruxolitinib and calcitriol in estrogen receptor-positive, human epidermal growth factor receptor 2-positive breast cancer cells," Molecular Medicine Reports, 2018, 8 pages.

International Search Report dated Apr. 4, 2022, PCT/US2021/061744.

Punwani et al., "Preliminary clinical activity of a topical JAK1/2 inhibitor in the treatment of psoriasis," Journal of the American Academy of Dermatology, vol. 67, No. 4, Oct. 1, 2012, pp. 658-664.

Kim et al., "Treatment of atopic dermatitis with ruxolitinib cream (JAK1/JAK2 inhibitor) or triamcinolone cream," Journal of Allergy and Clinical Immunology, vol. 145, No. 2, Oct. 17, 2029, pp. 572-582.

Indushekhar et al., "Plasma pharmacokinetics and distribution of ruxolitinib into skin following oral and topical administration in minipigs," International Journal of Pharmaceutics, vol. 590, Sep. 17, 2020.

International Search Report dated Mar. 24, 2023, PCT/US2022/080873.

* cited by examiner

*Primary Examiner* — Erich A Leeser
(74) *Attorney, Agent, or Firm* — Finnegan, Henderson, Farabow, Garrett & Dunner, LLP

(57) ABSTRACT

The present disclosure relates to topical formulations and methods of treating skin diseases using topical formulations comprising a JAK 1/2 inhibitor, which is ruxolitinib, or a pharmaceutically acceptable salt thereof, and an organic amine pH adjusting agent. The skin diseases for treatment include, but are not limited to, psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, ichthyosis, and a disorder of keratinization. The organic amine pH adjusting agent is a tertiary amine or an alkanol amine.

49 Claims, 2 Drawing Sheets

TOPICAL FORMULATIONS OF RUXOLITINIB WITH AN ORGANIC AMINE pH ADJUSTING AGENT FOR TREATMENT OF SKIN DISEASES

The present application claims priority to U.S. application Ser. No. 17/541,601, filed Dec. 3, 2021, and U.S. Provisional Application No. 63/365,973, filed Jun. 7, 2022; the contents of each application is incorporated herein by reference in its entirety.

The present disclosure relates to topical formulations and methods of treating skin diseases administering a JAK 1/2 inhibitor, which is ruxolitinib, or a pharmaceutically acceptable salt thereof, and an organic amine pH adjusting agent.

Inflammation mediated by the Janus kinase (JAK)-signal transducer is one of the important characteristics of auto-immune skin diseases. Janus kinase (JAK) inhibitors have been developed as agents for the treatment of inflammatory skin diseases including atopic dermatitis, alopecia areata, psoriasis, and vitiligo. For example, the JAK 1/2 inhibitor, ruxolitinib, has been approved as a topical product for treatment of atopic dermatitis and has been investigated in clinical trials for the treatment of vitiligo and psoriasis.

Current topical formulations of ruxolitinib utilize the phosphate salt of ruxolitinib, which is described in described and patented in U.S. Pat. No. 8,722,693, which is incorporated herein by reference in its entirety. Due to the acidic nature of the phosphate salt, the topical cream product is generally of low pH. Further, due in part to the pH dependent solubility of ruxolitinib phosphate, higher pH formulations have not been studied clinically, and the current approved formulation is limited to a strength of 1.5% w/w ruxolitinib phosphate on a free base basis.

Unexpectedly, topical formulations of ruxolitinib of higher pH have been discovered and are disclosed herein.

SUMMARY

As described above, ruxolitinib phosphate has been approved as topical cream formulation at 1.5% w/w for the treatment of atopic dermatitis and has been investigated in clinical trials for the treatment of vitiligo and psoriasis. Due to the acidic nature of the phosphate salt, the cream product is generally of low pH (e.g., pH of not greater than 3.6). The cream product is approved a strength of 1.5% w/w ruxolitinib phosphate on a free base basis due to, in part, the pH dependent solubility of the acidic ruxolitinib phosphate. Indeed, the solubility of ruxolitinib phosphate has been shown to be dramatically higher in deionized water (about 1.8% w/w) than in a pH 7 buffer (0.03% w/w) (see Example 1).

Unexpectedly, topical formulations of ruxolitinib having higher pH have been discovered and are disclosed herein. The discovery utilizes an organic amine pH-adjusting agent which allows for good solubility of ruxolitinib to be attained in solutions and in the formulations and at pHs greater than 4 (e.g., pH 5.5). In some solvent systems of the formulations, higher saturated solubility for ruxolitinib in the formulation has surprisingly been obtained through use of an organic pH adjusting agent.

Further, it has been surprisingly discovered that formulations utilizing the organic pH adjusting agent could deliver higher amounts of ruxolitinib to the dermis of the skin as compared to formulations without the organic pH adjusting agent, even though the formulations utilizing the organic pH adjusting agent were of substantially lower ruxolitinib strengths.

Additionally, it has also been discovered that the use of the solvent combinations of transcutol P-glycerol and water-ethanol increase the solubility of ruxolitinib phosphate synergistically. These solvent combinations are useful to prepare new formulations of ruxolitinib.

Accordingly, the present disclosure provides for a topical formulation for treating a skin disease comprising a JAK 1/2 inhibitor, which is ruxolitinib, or a pharmaceutically acceptable salt thereof, and an organic amine pH adjusting agent. The present disclosure further provides for the organic amine pH adjusting agent is a tertiary amine or an alkanol amine. In some embodiments, the alkanol amine is a di- or tri-alkanolamine. In some embodiments, the alkanol amine is a trialkanolamine.

The present disclosure also provides for the formulation, wherein the JAK 1/2 inhibitor is a pharmaceutically acceptable salt of ruxolitinib. The present disclosure also provides for the formulation, wherein the JAK 1/2 inhibitor, or a pharmaceutically acceptable salt thereof, is ruxolitinib phosphate. The present disclosure also provides for the formulation, wherein the JAK 1/2 inhibitor, or a pharmaceutically acceptable salt thereof, is ruxolitinib sulfate. The present disclosure also provides for the formulation, wherein the JAK 1/2 inhibitor, or a pharmaceutically acceptable salt thereof, is ruxolitinib maleate. It is recognized that the organic pH adjusting agent may interact with acidic salts of ruxolitinib such as ruxolitinib phosphate, potentially resulting in the formation of ruxolitinib free base or other complex mixtures. It is therefore intended that embodiments and claims that recite ruxolitinib salts, including ruxolitinib phosphate, encompasses such species or mixtures.

The present disclosure provides for the formulation which comprises from about 0.05% to about 3.0% or about 0.05% to about 1.5% w/w of the ruxolitinib, or a pharmaceutically acceptable salt thereof, on a free base basis. Further for example, the present disclosure provides for the formulation which comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis of the ruxolitinib, or the pharmaceutically acceptable salt thereof.

The present disclosure provides for the formulation which is in a form chosen from a cream, a lotion, a foam or foamable formulation, a spray (e.g., a pump spray), an aqueous gel, a non-aqueous gel, and an emulsified gel. The present disclosure provides for the formulation which is a cream or a lotion.

The present disclosure also provides for the formulation further comprising one or more of water, an oil component, an emulsifier or stabilizer component, and a solvent component. The present disclosure provides for the formulation wherein the water is present in an amount from about 5% to about 90%, from about 10% to about 80%, from about 10% to about 70%, from about 10% to about 60%, about 20% to about 70%, about 20% to about 60%, or from about 20% to about 50% by weight of the formulation. The present disclosure provides for the formulation wherein the oil component is present in an amount from about 5% to about 90%, from about 5% to about 80%, from about 5% to about 70%, from about 5% to about 60%, from about 5% to about 50%, or from about 5% to about 40% by weight of the formulation. The present disclosure provides for the formulation wherein the emulsifier or stabilizer component is present in an amount from about 1% to about 30% or from about 5% to about 25% by weight of the formulation. The present disclosure provides for the formulation wherein the solvent component comprises from about 5% to about 20%, from about 2% to about 30%, from about 5% to about 30%, from about 5% to about 25%, from about 5% to about 20%, or from about 10% to about 20% by weight of the pharmaceutical formulation.

The present disclosure provides for the formulation further comprising one or more of a stabilizing agent and an antioxidant.

The present disclosure provides for the formulation having a pH of 4 or greater. The present disclosure provides for the formulation having a pH of from about 4.0 to about 8.0, from about 4.0 to about 7.0, from about 4.0 to about 6.0, about 5.0 to about 8.0, from about 5.5 to about 7.5, from about 5.5 to about 7.0, from about 5.5 to about 6.5, from about 5.0 to about 6.0, and at about 5.5. The present disclosure provides for the amine pH adjusting agent is independently selected from trolamine, tris, ethanolamine, diethanolamine, ammonia, diisopropanolamine, 1-amino-2-propanol, 2-amino-2-ethyl-1,3-propanediol, 2-amino-2-methyl-1-propanol, diisopropylamine, imidazole, and pyridine. The present disclosure provides for the formulation wherein the amine pH adjusting agent is trolamine. The present disclosure provides for the formulation wherein pH adjustment to >5.5% with trolamine increased drug loading to >8% w/w.

The present disclosure provides for the formulation further comprising one or more pH adjusting agents, chelating agents, preservatives, co-solvents, penetration enhancers, humectants, thickening agents, gelling agents, viscosity building agents, surfactants, propellants, fragrances, colorants, and any combination thereof.

The present disclosure provides for the formulation wherein the organic amine pH adjusting agent is trolamine and further comprising Transcutol P and glycerol. The present disclosure provides for the organic amine pH adjusting agent is trolamine and further comprising ethanol and water.

The present disclosure further provides for a method of treating a skin disease in a patient in need thereof, comprising topically administering to an affected area of the patient a topical formulation comprising a JAK 1/2 inhibitor, which is ruxolitinib, or a pharmaceutically acceptable salt thereof, and an organic amine pH adjusting agent. The present disclosure provides for the JAK 1/2 inhibitor, or a pharmaceutically acceptable salt thereof, is ruxolitinib phosphate. In some embodiments, the skin disease is an autoimmune or an inflammatory skin disease. In some embodiments, the skin disease is a Th1 or Th17 associated skin disease. The present disclosure provides for the skin disease is mediated by interleukin 22 (IL-22), C—X—C motif chemokine 10 (CXCL10), matrix metallopeptidase 12 (MMP12), or a combination thereof. In some embodiments, the skin disease is mediated by Defb4, S100a12, or Serpinb4. In some embodiments, the skin disease is mediated by filaggrin/FLG, Loricin/LOR, IL-31, TSLP, CAMP, CCL17, CCL22, DefB4a, interferon-gamma, IL-17A, IL-17F, IL-22, IL-33, IL-4, or TNFSF18. In some embodiments, the skin disease is selected from psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, and ichthyosis. In some embodiments, the skin disease is rosacea, psoriatic arthritis, dermal fibrosis, morphea, spitz nevi, dermatophytosis, or acne vulgaris. The present disclosure provides for the method wherein there is a synergistic effect occurs between the JAK1/2 inhibitor, or the pharmaceutically acceptable salt thereof, and the amine pH adjusting agent.

The present disclosure also provides for the method wherein the formulation is administered at least one time per day. The present disclosure provides for the method wherein the formulation is administered at least two times per day.

The present disclosure provides for the method wherein the topical formulation which is chosen from a cream, a lotion, a foam or foamable formulation, a spray (e.g., a pump spray), an aqueous gel, a non-aqueous gel, and an emulsified gel. The present disclosure provides for the formulation is a cream or a lotion. The present disclosure provides for the formulation having a pH of from about 4.0 to about 8.0, from about 4.0 to about 7.0, from about 4.0 to about 6.0, about 5.0 to about 8.0, from about 5.5 to about 7.5, from about 5.5 to about 7.0, from about 5.5 to about 6.5, from about 5.0 to about 6.0, and at about 5.5.

The present disclosure provides for the method wherein the organic amine pH adjusting agent is a tertiary amine or an alkanol amine. In some embodiments, the alkanol amine is a di- or tri-alkanolamine. The present disclosure provides for the method wherein the amine pH adjusting agent is independently selected from trolamine, tris, ethanolamine, diethanolamine, ammonia, diisopropanolamine, 1-amino-2-propanol, 2-amino-2-ethyl-1,3-propanediol, 2-amino-2-methyl-1-propanol, diisopropylamine, imidazole, and pyridine. The present disclosure provides for the amine pH adjusting agent is trolamine. The present disclosure provides for the method wherein the pH adjustment to >5.5% with trolamine increased drug loading to >8% w/w.

The present disclosure provides for the formulation which comprises one or more of water, an oil component, an emulsifier or stabilizer component, and a solvent component. The present disclosure provides for the water comprises from about 5% to about 90%, from about 10% to about 80%, from about 10% to about 70%, from about 10% to about 60%, about 20% to about 70%, about 20% to about 60%, or from about 20% to about 50% by weight of the pharmaceutical formulation. The present disclosure provides for the formulation wherein the oil component comprises from about 5% to about 90%, from about 5% to about 80%, from about 5% to about 70%, from about 5% to about 60%, from about 5% to about 50%, or from about 5% to about 40% by weight of the pharmaceutical formulation. The present disclosure provides for the formulation wherein the emulsifier or stabilizer component comprises from about 1% to about 30% or from about 5% to about 25% by weight of the formulation. The present disclosure provides for the formulation wherein the solvent component comprises from about 5% to about 20%, from about 2% to about 30%, from about 5% to about 30%, from about 5% to about 25%, from about 5% to about 20%, or from about 10% to about 20% by weight of the formulation.

The present disclosure provides for the formulation further comprising one or more of a stabilizing agent and an antioxidant. The present disclosure provides for the formulation further comprising one or more pH adjusting agents, chelating agents, preservatives, co-solvents, penetration enhancers, humectants, thickening agents, gelling agents, viscosity building agents, surfactants, propellants, fragrances, colorants, and any combination thereof. The present disclosure provides for the formulation wherein the organic amine pH adjusting agent is trolamine and further comprising Transcutol P and glycerol. The present disclosure provides for the formulation wherein the organic amine pH adjusting agent is trolamine and further comprising ethanol and water.

DESCRIPTION

Figure 1:
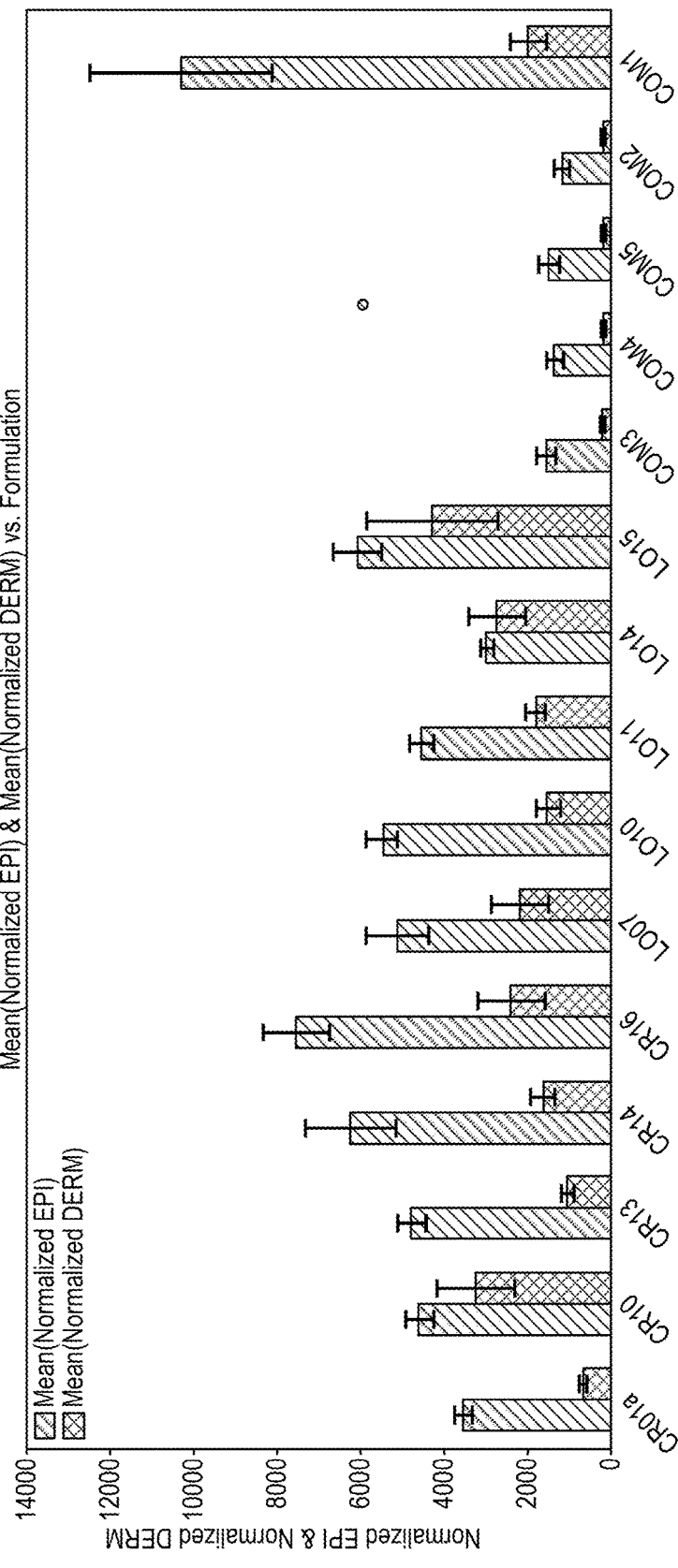
FIG. 1 illustrates the amount of ruxolitinib which permeated across the epidermis and dermis after 24 hours.

The present disclosure provides for topical formulations for treating a skin disease, comprising a JAK 1/2 inhibitor, which is ruxolitinib, or a pharmaceutically acceptable salt thereof, and an organic amine pH adjusting agent.

JAK 1/2 Inhibitor

In some embodiments, the JAK 1/2 inhibitor, or the pharmaceutically acceptable salt thereof, is ruxolitinib. Ruxolitinib is a JAK1/JAK2 inhibitor. Ruxolitinib has an $IC_{50}$ of less than 10 nM at 1 mM ATP at JAK1 and JAK2. ruxolitinib can be made by the procedure described in U.S. Pat. No. 7,598,257 (Example 67), filed Dec. 12, 2006, which is incorporated herein by reference in its entirety.

Ruxolitinib

In some embodiments, the JAK 1/2 inhibitor, or the pharmaceutically acceptable salt thereof, is a pharmaceutically acceptable salt of ruxolitinib. In some embodiments, the JAK 1/2 inhibitor, or the pharmaceutically acceptable salt thereof, is ruxolitinib sulfate. In some embodiments, the JAK 1/2 inhibitor, or the pharmaceutically acceptable salt thereof, is ruxolitinib maleate.

In some embodiments, the JAK inhibitor, or the pharmaceutically acceptable salt thereof, is ruxolitinib phosphate. In some embodiments, the JAK inhibitor, or the pharmaceutically acceptable salt thereof, is the 1:1 ruxolitinib phosphoric acid salt. Ruxolitinib can be prepared as described in U.S. Pat. Nos. 7,598,257 and 8,415,362, each of which is incorporated herein by reference in its entirety. The phosphoric acid salt can be made as described in U.S. Pat. No. 8,722,693, which is incorporated herein by reference in its entirety.

In some embodiments, the JAK 1/2 inhibitor, or the pharmaceutically acceptable salt thereof, is ruxolitinib, wherein one or more hydrogen atoms are replaced by deuterium atoms, or a pharmaceutically acceptable salt thereof.

In some embodiments, the ruxolitinib or the salt thereof is administered as a topical formulation. In some embodiments, the topical formulation comprises from about 0.05% to about 3.0%, or about 0.05% to about 1.5% by weight of the formulation on a free base basis of the ruxolitinib, or the pharmaceutically acceptable salt thereof. In some embodiments, the topical formulation comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis of the ruxolitinib, or the pharmaceutically acceptable salt thereof. In some embodiments, the topical formulation comprises from about 0.5% to about 1.5% by weight of the formulation on a free base basis of the ruxolitinib, or the pharmaceutically acceptable salt thereof.

Organic Amine pH Adjusting Agent

The present disclosure provides for topical formulations for treating a skin disease, comprising a JAK 1/2 inhibitor, which is ruxolitinib, or a pharmaceutically acceptable salt thereof, and an organic amine pH adjusting agent.

In some embodiments, the organic amine pH adjusting agent is a tertiary amine. In some embodiments, the organic amine pH adjusting agent is an alkanol amine. In some embodiments, the alkanol amine is a di- or tri-alkanolamine. In some embodiments, the organic amine pH adjusting agent is independently selected from trolamine, tris, ethanolamine, diethanolamine, ammonia, diisopropanolamine, 1-amino-2-propanol, 2-amino-2-ethyl-1,3-propanediol, 2-amino-2-methyl-1-propanol, diisopropylamine, imidazole, and pyridine.

In some embodiments, the organic amine pH adjusting agent is independently selected from trolamine, ethanolamine, diisopropanolamine, 2-amino-2-methyl-1-propanol, imidazole, and pyridine.

In some embodiments, the organic amine pH adjusting agent is independently selected from trolamine, ethanolamine, diethanolamine, ammonia, diisopropanolamine, 2-amino-2-ethyl-1,3-propanediol, 2-amino-2-methyl-1-propanol, diisopropylamine, imidazole, and pyridine. In some embodiments, the topical formulation is non-aqueous, and the organic amine pH adjusting agent is independently selected from trolamine, ethanolamine, diethanolamine, ammonia, diisopropanolamine, 2-amino-2-ethyl-1,3-propanediol, 2-amino methyl-1-propanol, diisopropylamine, imidazole, and pyridine. In some embodiments, the organic amine pH adjusting agent is trolamine.

In some embodiments, the organic amine pH adjusting agent is independently selected from trolamine, ethanolamine, diisopropanolamine, 2-amino-2-methyl-1-propanol, diisopropylamine, imidazole, and pyridine. In some embodiments, the topical formulation comprises water and a solvent component, and the organic amine pH adjusting agent is independently selected from trolamine, ethanolamine, diisopropanolamine, 2-amino-2-methyl-1-propanol, diisopropylamine, imidazole, and pyridine. In some embodiments, the solvent component comprises polyethylene glycol or propylene glycol, transcutol P, or mixtures thereof. In some embodiments, the water comprises 30% to 70% by weight of the topical formulation. In some embodiments, the water comprises 40% to 60% by weight of the topical formulation. In some embodiments, the solvent component comprises 40% to 80% by weight of the topical formulation. In some embodiments, the organic amine pH adjusting agent is trolamine.

In some embodiments, the organic amine pH adjusting agent is independently selected from trolamine, ethanolamine, diethanolamine, ammonia, diisopropanolamine, 2-amino-2-ethyl-1,3-propanediol, 2-amino-2-methyl-1-propanol, imidazole, and pyridine. In some embodiments, the topical formulation comprises water and a solvent component, and the organic amine pH adjusting agent is independently selected from trolamine, ethanolamine, diethanolamine, ammonia, diisopropanolamine, 2-amino-2-ethyl-1,3-propanediol, 2-amino-2-methyl-1-propanol, imidazole, and pyridine. In some embodiments, the solvent component comprises polyethylene glycol or propylene glycol, or mixtures thereof. In some embodiments, the solvent component comprises glycerol or transcutol P, or mixtures thereof. In some embodiments, the water comprises 10% to 40% by weight of the topical formulation. In some embodiments, the solvent comprises 10% to 40% by weight of the topical formulation. In some embodiments, the organic amine pH adjusting agent is trolamine.

In some embodiments, the amine pH adjusting agent is trolamine.

In some embodiments, pH adjustment of the formulation to >5.5% with trolamine increased drug loading to >8% w/w.

In some embodiments, the amine pH adjusting agent is present in an amount to adjust the pH of the formulation, wherein the formulation has a pH of from about 4.0 to about 8.0, from about 4.0 to about 7.0, from about 4.0 to about 6.0, about 5.0 to about 8.0, from about 5.5 to about 7.5, from about 5.5 to about 7.0, from about 5.5 to about 6.5, from about 5.0 to about 6.0, and at about 5.5. In some embodiments, the formulation has a pH of from about 4.0 to about 8.0. In some embodiments, the formulation has a pH of from about 4.0 to about 7.0. In some embodiments, the formulation has a pH of from about 4.0 to about 6.0. In some embodiments, the formulation has a pH of about 5.0 to about 8.0. In some embodiments, the formulation has a pH of from about 5.5 to about 7.5. In some embodiments, the formulation has a pH of from about 5.5 to about 7.0. In some embodiments, the formulation has a pH of from about 5.5 to about 6.5. In some embodiments, the formulation has a pH of from about 5.0 to about 6.0. In some embodiments, the formulation has a pH of about 5.5.

In some embodiments, the amine pH adjusting agent is present in an amount up to 11% w/w or up to 2.6% w/w by weight of the formulation. Further for example, in some embodiments, the amine pH adjusting agent is present in an amount from about 0.25% to about 0.5%, from about 0.5% to about 0.75%, from about 0.75% to about 1%, from about 1% to about 1.25%, from about 1.25% to about 1.5%, from about 1.5% to about 1.75%, from about 1.75% to about 2%, from about 2% to about 2.25%, from about 2.25% to about 2.5%, from about 2.5% to about 2.6%, from about 2.6% to about 2.75%, from about 2.75% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 11%, w/w, by weight of the formulation. In some embodiments, the amine pH adjusting agent is present in an amount up to 5%, w/w, by weight of the formulation. In some embodiments, the amine pH adjusting agent is present in an amount up to 4%, w/w, by weight of the formulation. In some embodiments, the amine pH adjusting agent is present in an amount up to 3%, w/w, by weight of the formulation. In some embodiments, the amine pH adjusting agent is present in an amount up to 2%, w/w, by weight of the formulation. In some embodiments, the amine pH adjusting agent is present in an amount of about 0.25% to about 5% w/w, by weight of the formulation. In some embodiments, the amine pH adjusting agent is present in an amount of about 0.5% to about 5% w/w, by weight of the formulation. In some embodiments, the amine pH adjusting agent is present in an amount of about 1% to about 5% w/w, by weight of the formulation. In some embodiments, the amine pH adjusting agent is present in an amount of about 2% to about 5% w/w, by weight of the formulation. In some embodiments, the amine pH adjusting agent is present in an amount of about 1% to about 3% w/w, by weight of the formulation. In some embodiments, the amine pH adjusting agent is trolamine.

In some embodiments, the organic amine pH adjusting agent is utilized without a need of a separate buffering solution (e.g., citric acid/sodium citrate buffer). In some embodiments, the organic amine pH adjusting agent is the only basic pH adjustment agent utilized. In some embodiments, there is no separate pH buffer.

In some embodiments, there is a synergistic effect between the JAK 1/2 inhibitor, or the pharmaceutically acceptable salt thereof, and the organic amine pH adjusting agent.

The present disclosure also provides for pharmaceutical formulations, wherein the formulation has a pH of from about 4.0 to about 8.0, from about 4.0 to about 7.0, from about 4.0 to about 6.0, about 5.0 to about 8.0, from about 5.5 to about 7.5, from about 5.5 to about 7.0, from about 5.5 to about 6.5, from about 5.0 to about 6.0, and at about 5.5. In some embodiments, the formulation has a pH of from about 4.0 to about 8.0. In some embodiments, the formulation has a pH of from about 4.0 to about 7.0. In some embodiments, the formulation has a pH of from about 4.0 to about 6.0. In some embodiments, the formulation has a pH of about 5.0 to about 8.0. In some embodiments, the formulation has a pH of from about 5.5 to about 7.5. In some embodiments, the formulation has a pH of from about 5.5 to about 7.0. In some embodiments, the formulation has a pH of from about 5.5 to about 6.5. In some embodiments, the formulation has a pH of from about 5.0 to about 6.0. In some embodiments, the formulation has a pH of about 5.5.

Topical Formulations

The present disclosure provides for topical formulations for treating a skin disease, comprising a JAK 1/2 inhibitor, which is ruxolitinib, or a pharmaceutically acceptable salt thereof, and an organic amine pH adjusting agent.

Topical (e.g., intradermal) administration provides the advantage of treating the skin diseases and/or disorder as described herein locally, minimizing potential adverse events associated with systemic exposure, and allowing an easier discontinuation of the therapy, if necessary. Additionally, some topical dosage forms such as creams, ointments, and gels have the benefit of excipients that may act as emollients or occlusive agents, which can increase patient well-being and compliance during the treatment period. Other dosage routes such as oral, parenteral, and inhalation may lead to supratherapeutic systemic drug levels, increased likelihood of adverse events, drug-drug interactions, and generation of active/toxic metabolites, which may result in treatment discontinuation and inadequate patient compliance.

Topical formulations intended for dermal delivery are typically solutions, suspensions, gels, creams, ointments, lotions, sprays, and foams or foamable formulation and can contain one or more conventional carriers as described herein. The formulation composition should be prepared with the goal of delivering the active ingredient to the appropriate layer(s) of the skin, minimizing systemic exposure, and preventing skin irritation. Additionally, the pharmaceutical composition should be physically and chemically stable. Depending on the selected dosage form, one or more additional excipients as described herein may be necessary, e.g., pH adjusting agents, chelating agents, preservatives, co-solvents, penetration enhancers, humectants, thickening agents, gelling agents, viscosity building agents, surfactants, propellants, fragrances, colorants, or any combination or mixture thereof.

In some embodiments, the topical formulation is an aqueous formulation. In some embodiments, the topical formulation is independently selected from creams, lotions, foams or foamable formulation, sprays, aqueous gels, non-aqueous gels, and emulsified gels. The present disclosure also provides for topical formulations, wherein the formulation is a cream or a lotion.

The present disclosure provides for topical formulations for treating a skin disease, comprising a JAK 1/2 inhibitor, which is ruxolitinib, or a pharmaceutically acceptable salt thereof, and an organic amine pH adjusting agent.

In some embodiments, the topical formulation further comprises one or more of water, an oil component, and a solvent component. In some embodiments, the oil component further comprises an emulsifier or stabilizing component (or alternatively, an emulsifier or wetting agent component). The present disclosure also provides for topical formulations, further comprising one or more of a stabilizing agent and an antioxidant. In some embodiments, the topical formulation comprises one or more of pH adjusting agents, chelating agents, preservatives, co-solvents, penetration enhancers, humectants, thickening agents, gelling agents, viscosity building agents, surfactants, propellants, fragrances, colorants, or any combination or mixture thereof.

In some embodiments, the topical formulation comprises water. In some embodiments, the topical formulation comprises water and an oil component. In some embodiments, the topical formulation comprises water, an oil component, and an emulsifier or stabilizer component. In some embodiments, the topical formulation comprises water, an oil component, an emulsifier or stabilizer component, and a solvent component.

In some embodiments, the topical formulation comprises an oil component. In some embodiments, the topical formulation comprises an oil component, and an emulsifier or stabilizer component. In some embodiments, the topical formulation comprises an oil component, an emulsifier or stabilizer component, and a solvent component.

In some embodiments, the topical formulation comprises an emulsifier or stabilizer component. In some embodiments, the topical formulation comprises water, and an emulsifier or stabilizer component. In some embodiments, the topical formulation comprises an oil component and an emulsifier or stabilizer component. In some embodiments, the topical formulation comprises an emulsifier or stabilizer component, and a solvent component.

In some embodiments, the topical formulation comprises a solvent component. In some embodiments, the topical formulation comprises water and a solvent component. In some embodiments, the topical formulation comprises an oil component and a solvent component.

In some embodiments, the topical formulation comprises:
from about 20% to 60% of water by weight of the formulation;
from about 10% to about 50% of a solvent component by weight of the formulation;
from about 10% to about 40% of an oil component by weight of the formulation; and
an organic amine adjusting agent;
wherein the pH of the formulation ranges from 5.5 to about 7.5.

In some embodiments, the topical formulation comprises:
from about 30% to 60% of water by weight of the formulation;
from about 10% to about 40% of a solvent component by weight of the formulation;
from about 10% to about 30% of an oil component by weight of the formulation;
from about 0.1% to about 20% glycerol;
an organic amine adjusting agent;
wherein the pH of the formulation ranges from 5.5 to about 7.5.

In some embodiments, the topical formulation comprises:
from about 30% to 60% of water by weight of the formulation;
from about 10% to about 40% of a solvent component by weight of the formulation;
from about 10% to about 30% of an oil component by weight of the formulation;
from about 5% to about 20% glycerol;
an organic amine adjusting agent;
wherein the pH of the formulation ranges from 5.5 to about 7.5 and wherein the topical formulation is a cream or a lotion.

In some embodiments, the topical formulation comprises:
from about 30% to 60% of water by weight of the formulation;
from about 10% to about 40% of a solvent component by weight of the formulation;
from about 10% to about 30% of an oil component by weight of the formulation;
from about 10% to about 20% glycerol;
an organic amine adjusting agent;
wherein the pH of the formulation ranges from 5.5 to about 7.5 and wherein the topical formulation is a cream or a lotion.

In some embodiments, the topical formulation comprises water, glycerol, transcutol P, polysorbate 80, cetyl alcohol, stearyl alcohol, light mineral oil, white soft paraffin, GTCC, and trolamine, and the topical formulation is a cream.

In some embodiments, the topical formulation comprises water, glycerol, transcutol P, polysorbate 80, cetyl alcohol, mineral oil, white soft paraffin, GTCC, and trolamine, and the topical formulation is a lotion.

The water, oil components, emulsifier or stabilizer/emulsifier or wetting agent components, solvent components, stabilizing agents, antioxidants, and additional components can be combined in any suitable combination from the embodiments described below.

In some embodiments, the formulation does not comprise a vitamin D3 analog.

Water

In some embodiments, the formulation comprises water. In some embodiments, the water is present in an amount from about 5% to about 90%, from about 10% to about 90%, from about 10% to about 80%, from about 10% to about 70%, from about 10% to about 60%, from about 10% to about 50%, from about 20% to about 70%, from about 20% to about 60%, from about 30% to about 60%, or from about 20% to about 50% by weight of the formulation.

In some embodiments, the water is present in an amount of about 35% to about 65% by weight of the formulation.

In some embodiments, the water is present in an amount of about 40% to about 60% by weight of the emulsion.

In some embodiments, the water is present in an amount of about 45% to about 55% by weight of the emulsion.

Oil Component

In some embodiments, the formulation comprises an oil component. In some embodiments, the oil component is present in an amount from about 5% to about 90%, from about 5% to about 80%, from about 5% to about 70%, from about 5% to about 60%, from about 5% to about 50%, or from about 5% to about 40% by weight of the formulation.

In some embodiments, the oil component is present in an amount of about 10% to about 40% by weight of the formulation.

In some embodiments, the oil component is present in an amount of about 10% to about 24% by weight of the formulation.

In some embodiments, the oil component is present in an amount of about 15% to about 24% by weight of the formulation.

In some embodiments, the oil component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), polyoxyethylene stearyl ether (Brij S721), ethoxylated stearic and cetyl alcohols (Kolliphor CS20)), waxes (e.g., paraffin (soft white paraffin), emulsifying waxes (Polawax)), mineral, natural, hydrogenated, and silicone oils (e.g., light mineral oil, castor oil, silicone oils (e.g., cyclomethicone, dimethicone), hydrogenated castor oils (Kolliphor HCO), fatty ester (cocoyl caprylocaprate (Kollicream 3C)), and triglycerides (caprylic/capric triglyceride (Crodamol GTCC), medium chain triglycerides), or combinations thereof. In some embodiments, the oil component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax), or combinations thereof.

In some embodiments, the oil component comprises one or more substances independently selected from petrolatums, fatty alcohols, mineral oils, triglycerides, and silicone oils.

In some embodiments, the oil component comprises one or more substances independently selected from white petrolatum, cetyl alcohol, stearyl alcohol, light mineral oil, medium chain triglycerides, and dimethicone.

In some embodiments, the oil component comprises an emulsifier or stabilizer component. The emulsifier or stabilizer component are described below.

In some embodiments, the oil component further comprises one or more substances independently selected from an emollient agent, an occlusive agent, and a stiffening agent, and combinations thereof.

In some embodiments, the emollient component is present in an amount of about 5% to about 15% by weight of the formulation.

In some embodiments, the emollient component comprises one or more substances independently selected from mineral oils and triglycerides.

In some embodiments, the emollient component comprises one or more substances independently selected from light mineral oil and medium chain triglycerides.

In some embodiments, the light mineral oil is present in an amount of about 0.1% to about 15% by weight of the formulation.

In some embodiments, the emollient component comprises one or more substances independently selected from light mineral oil, medium chain triglycerides, and dimethicone.

In some embodiments, the occlusive agent component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax).

In some embodiments, the occlusive agent component comprises one or more substances selected from lanolin acid fatty alcohols, lanolin alcohol, petrolatum, propylene glycol, dimethicone, cholesterol, cocoa butter, Carnauba wax, and bees wax.

In some embodiments, the occlusive agent component comprises petrolatum.

In some embodiments, the occlusive agent component comprises white petrolatum.

In some embodiments, the white petrolatum is present in an amount of about 0.1% to about 15% by weight of the formulation.

In some embodiments, the oil component comprises a stiffening agent component.

In some embodiments, the stiffening agent component is present in an amount of about 2% to about 8% by weight of the formulation.

In some embodiments, the stiffening agent component comprises one or more substances independently selected from fatty alcohols.

In some embodiments, the stiffening agent component comprises one or more substances independently selected from $C_{12-20}$ fatty alcohols.

In some embodiments, the stiffening agent component comprises one or more substances independently selected from $C_{16-18}$ fatty alcohols.

In some embodiments, the stiffening agent component comprises one or more substances independently selected from cetyl alcohol and stearyl alcohol.

In some embodiments, the cetyl alcohol is present in an amount of about 0.1% to about 15% by weight of the formulation.

In some embodiments, the stearyl alcohol is present in an amount of about 0.1% to about 15% by weight of the formulation.

In some embodiments, the stiffening agent component comprises one or more substances independently selected from cetyl alcohol, stearyl alcohol, oleyl alcohol, and cetosteryl alcohol.

Emulsifier or Stabilizer Component/Emulsifier or Wetting Agent Component

In some embodiments, the formulation comprises an emulsifier or stabilizer (or emulsifier or wetting agent) component. In some embodiments, the oil component comprises an emulsifier or stabilizer component. In some embodiments, the emulsifier or stabilizer component is present in an amount from about 1% to about 40%, from about 1% to about 30%, from about 1% to about 20%, from about 5% to about 40%, or from about 5% to about 25% by weight of the formulation. In some embodiments, the emulsifier component is added to the oil component and the weight percentages of the individual components may be adjusted accordingly. In some embodiments, the emulsifier component when added to the oil component may be a separate component of the formulations.

In some embodiments, the emulsifier component is present in an amount of about 1% to about 9% by weight of the formulation.

In some embodiments, the emulsifier component is present in an amount of about 2% to about 6% by weight of the formulation.

In some embodiments, the emulsifier component is present in an amount of about 3% to about 5% by weight of the formulation.

In some embodiments, the emulsifier component is present in an amount of about 4% to about 7% by weight of the formulation.

In some embodiments, the emulsion comprises an emulsifier component and a stiffening agent component, wherein the combined amount of emulsifier component and stiffening agent component is at least about 8% by weight of the formulation.

In some embodiments, the emulsifying or wetting agent component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), polyoxyethylene stearyl ether (Brij S721), ethoxylated stearic and cetyl alcohols (Kolliphor CS20)), and emulsifying waxes (Polawax)). In some embodiments, the emulsifying or wetting agent component comprises one or more substances selected from fatty alcohols (e.g., cetyl alcohol, stearyl alcohol, and cetostearyl alcohol (such as Kolliphor CSA50)), fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), and polyoxyethylene stearyl ether (Brij S721), ethoxylated stearic and cetyl alcohols (Kolliphor CS20)).

In some embodiments, the emulsifier component comprises one or more substances independently selected from glyceryl fatty esters and sorbitan fatty esters.

In some embodiments, the emulsifier component comprises one or more substances independently selected from glyceryl stearate, and polysorbate 20.

In some embodiments, the emulsifier component comprises a non-ionic surfactant.

In some embodiments, the non-ionic surfactant is cetomacrogol 1000 or poloxamer 407.

In some embodiments, the poloxamer is poloxamer 407.

In some embodiments, the emulsifier component further comprises glyceryl stearate andPEG-100 stearate, such as Arlacel™ 165.

Solvent Component

In some embodiments, the emulsion further comprises a solvent component. In some embodiments, the solvent component is present in an amount from about 1% to about 70%, from about 1% to about 60%, from about 1% to about 50%, from about 1% to about 40%, from about 1% to about 30%, from about 1% to about 20%, from about 10% to about 70%, from about 10% to about 60%, from about 10% to about 50%, about 10% to about 40%, about 10% to about 40%, about 10% to about 30%, from about 1% to about 20%, from about 5% to about 20%, from about 2% to about 30%, from about 5% to about 30%, from about 5% to about 25%, from about 5% to about 20%, or from about 10% to about 20% by weight of the pharmaceutical formulation.

In some embodiments, the solvent component is present in an amount of about 10% to about 35% by weight of the formulation.

In some embodiments, the solvent component is present in an amount of about 15% to about 30% by weight of the formulation.

In some embodiments, the solvent component is present in an amount of about 20% to about 25% by weight of the formulation.

In some embodiments, the solvent component comprises one or more hydroxylated solvents. In some embodiments, the solvent component comprises one or more substances selected from diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the solvent component comprises one or more substances independently selected from alkylene glycols and polyalkylene glycols.

In some embodiments, the solvent component comprises one or more substances independently selected from propylene glycol and polyethylene glycol.

In some embodiments, the solvent component comprises one or more substances independently selected from PEG200, PEG300, PEG400, propylene glycol.

In some embodiments, the solvent component comprises PEG300 and propylene glycol.

In some embodiments, the PEG300 is present in an amount of about 7% w/w by weight of the formulation.

In some embodiments, the solvent is a combination of PEG400 and propylene glycol.

In some embodiments, the propylene glycol is present of about 6.5% by weight of the formulation. In some embodiments, the solvent component comprises diethylene glycol monoethyl ether, such as Transcutol® P. In some embodiments, the diethylene glycol monoethyl ether is present in an amount of about 0.1% to about 30% w/w by weight of the emulsion. In some embodiments, the diethylene glycol monoethyl ether is present in an amount of about 0.1% to about 20% w/w by weight of the formulation.

Stabilizing Agent

In some embodiments, the formulation further comprises a stabilizing agent component.

In some embodiments, the stabilizing agent component is present in an amount of about 0.05% to about 5% by weight of the formulation.

In some embodiments, the stabilizing agent component is present in an amount of about 0.1% to about 2% by weight of the formulation.

In some embodiments, the stabilizing agent component is present in an amount of about 0.3% to about 0.5% by weight of the formulation.

In some embodiments, the stabilizing agent component comprises one or more substances independently selected from polysaccharides.

In some embodiments, the stabilizing agent component comprises xanthan gum.

Antioxidant

In some embodiments, the formulation further comprises an antioxidant.

In some embodiments, the antioxidant is butylated hydroxytoluene (BHT), butylated hydroxyanisole (BHA), or tocopherol, or a combination thereof.

Additional Components

In some embodiments, the formulation further comprises a chelating agent component.

In some embodiments, the chelating agent component comprises edetate disodium.

In some embodiments, the edetate disodium is present in an amount of about 0.001% to about 5% by weight of the formulation.

In some embodiments, the formulation further comprises a humectant.

In some embodiments, the humectant is glycerol.

In some embodiments, the glycerol is present in an amount of about 0.01% to about 20% by weight of the formulation.

In some embodiments, the glycerol is present in an amount of about 0.1% to about 20% by weight of the formulation.

In some embodiments, the formulation further comprises a surfactant.

In some embodiments, the surfactant is polysorbate 80. In some embodiments, the surfactant is polysorbate 80 is present in an amount of about 0.01% to about 15% by weight of the formulation. In some embodiments, the surfactant is polysorbate 80 is present in an amount of about 0.1% to about 15% by weight of the formulation.

In some embodiments, the formulation comprises one or more preservatives. In some embodiments, the one or more preservatives are benzyl alcohol, methyl paraben, propyl paraben, phenoxyethanol, and combinations thereof.

In some embodiments, the formulation comprises one or more propellant. In some embodiments, the propellant comprises one or more hydrofluorocarbons (HFCs) or hydrofluoroolefins (HFOs). In some embodiments, the propellant comprises one or more hydrofluorocarbons (HFCs). In some embodiments, the propellant comprises one or more hydrofluoroolefins (HFOs). In some embodiment, the propellant comprises HFA-134. In some embodiment, the propellant comprises HFO-1234ze.

In some embodiments, the formulation comprises a penetration enhancer. In some embodiments, penetration enhancers facilitate the delivery of the formulation across the affected area of the patient. In some embodiments, a penetration enhancer comprises a polyol such as polyethylene glycol (PEG), glycerol (glycerin), maltitol, sorbitol etc.; diethylene glycol monoethyl ether, azone, benzalkonium chloride (ADBAC), cetylperidium chloride, cetylmethylammonium bromide, dextran sulfate, lauric acid, menthol, methoxysalicylate, oleic acid, phosphatidylcholine, polyoxyethylene, polysorbate 80, sodium glycholate, sodium lauryl sulfate, sodium salicylate, sodium taurocholate, sodium taurodeoxycholate, sulfoxides, sodium deoxycholate, sodium glycodeoxycholate, sodium taurocholate and surfactants such as sodium lauryl sulfate, laureth-9, cetylpyridinium chloride and polyoxyethylene monoalkyl ethers, benzoic acids, such as sodium salicylate and methoxy salicylate, fatty acids, such as lauric acid, oleic acid, undecanoic acid and methyl oleate, fatty alcohols, such as octanol and nonanol, laurocapram, cyclodextrins, thymol, limonene, urea, chitosan and other natural and synthetic polymers.

In some embodiments, the formulation comprises a thickening agent. In some embodiments, a thickening agent comprises beeswax, hard paraffin or cetyl alcohol, xanthan gum, carboxymethyl cellulose, hydroxypropyl cellulose, carbomer, or povidone (e.g., Kollidon 90f).

In some embodiments, the formulation comprises a gelling agent. In some embodiments, a gelling agent is a material that can swell or expand when in contact with water. In some embodiments, the gelling agent comprises swellable polymers such as osmopolymers or hydrogels. In some embodiments, the gelling agent is non-cross linked or lightly cross-linked. In some embodiments, the gelling agent is olyhydroxyalkylcellulose having a molecular weight greater than 50,000, such as hydroxyl propylmethylcellulose (METHOCEL K 100M available from Dow Chemical); poly(hydroxyalkylmethacrylate) having a molecular weight of from 5,000 to 5,000,000; poly(vinylpyrrolidone) having a molecular weight of from 100,000 to 3,000,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams, and the like.

In some embodiments, the formulation comprises a viscosity building agent. In some embodiments, the viscosity building agent includes, but is not limited to, natural or synthetic waxes such as carnauba wax, cetyl ester wax, microcrystalline wax, white wax, yellow wax, bees wax, ozokerite, paraffin, ceresin, esparto wax, ouricury wax, and rezowax, hard fats (e.g., hydrogenated vegetable glycerides), hydrogenated vegetable oils, $C_{12}$-$C_{60}$ alcohols, $C_{12}$-$C_{60}$ acids, alpha-hydroxy fatty acids, polyhydroxy fatty acid esters, polyhydroxy fatty acid amides and combinations thereof.

In some embodiments, the formulation comprises one or more preservatives. In some embodiments, the one or more preservatives are benzyl alcohol, methyl paraben, propyl paraben, butylated hydroxytoluene (BHT), phenoxyethanol, and combinations thereof.

In some embodiments, the formulation further comprises one or more co-solvents. In some embodiments, the one or more co-solvents comprise one or more additional hydroxylated solvents. In some embodiments, the solvent component comprises one or more substances selected from diethylene glycol diethers (e.g., diethylene glycol monoethyl ether (Transcutol P)), alkylene glycols (e.g., propylene glycol), or polyethylene glycols (e.g., PEG400).

In some embodiments, topical formulations can contain one or more conventional carriers as described herein. In some embodiments, ointments can contain water and one or more hydrophobic carriers selected from, for example, liquid paraffin, polyoxyethylene alkyl ether, propylene glycol, white petrolatum, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like.

The formulations administered to a patient can be in the form of pharmaceutical compositions described above. These formulations or compositions can be sterilized by conventional sterilization techniques or may be sterile filtered. Aqueous solutions can be packaged for use as is, or lyophilized, the lyophilized preparation being combined with a sterile aqueous carrier prior to administration.

As will be appreciated, some components of the formulations described herein can possess multiple functions. For example, a given substance may act as both an emulsifying agent component and a stabilizing agent. In some such cases, the function of a given component can be considered singular, even though its properties may allow multiple functionalities. In some embodiments, each component of the formulation comprises a different substance or mixture of substances.

As described above, in some embodiments, the present disclosure provides a topical formulation which is in a form chosen from a cream, a lotion, a foam or foamable formulation, a spray (e.g., a pump spray), an aqueous gel, a non-aqueous gel, and an emulsified gel.

Creams

In some embodiments, the formulation is a cream formulation. In some embodiments, the formulation is an aqueous cream formulation. In some embodiments, the cream formulation is an oil-in-water emulsion. In some embodiments, the cream formulation comprises water and an oil component. In some embodiments, the cream formulation comprises water, a solvent component, and an oil component. In some embodiments, the oil component comprises an emulsifying or wetting agent component. In some embodiments, the oil component comprises one or more stabilizing agents.

In some embodiments, the water is present in an amount of about 10% to about 80% by weight of the formulation. In some embodiments, the water is present in an amount of about 10% to about 70% by weight of the formulation. In some embodiments, the water is present in an amount of about 10% to about 60% by weight of the formulation. In some embodiments, the water is present in an amount of about 20% to about 70% by weight of the formulation. In some embodiments, the water is present in an amount of about 20% to about 60% by weight of the formulation. In some embodiments, the water is present in an amount of about 30% to about 50% by weight of the formulation.

In some embodiments, the oil component is present in an amount of about 10% to about 60% by weight of the formulation. In some embodiments, the oil component is present in an amount of about 10% to about 50% by weight of the formulation. In some embodiments, the oil component is present in an amount of about 10% to about 40% by weight of the formulation. In some embodiments, the oil component is present in an amount of about 10% to about 30% by weight of the formulation.

In some embodiments, the oil component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters (isopropyl myristate), glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., polyethylene glycol hexadecyl ether (Cetomacrogol 1000), diethylene glycol monoethyl ether (Transcutol P), polyethylene glycol octadecyl ether (Brij S2), polyoxyethylene stearyl ether (Brij S721)), waxes (e.g., paraffin (soft white paraffin), emulsifying waxes (Polawax)), mineral, natural, hydrogenated, and silicone oils (e.g., light mineral oil, castor oil, silicone oils (e.g., cyclomethicone, dimethicone), hydrogenated castor oils (Kolliphor HCO), and triglycerides (caprylic/capric triglyceride (Crodamol GTCC), medium chain triglycerides), or combinations thereof. In some embodiments, the oil component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), xanthan gum, vegetable or animal fat (e.g., cocoa butter), vegetable wax (e.g., Carnauba wax), and wax ester (e.g., bees wax), or combinations thereof.

In some embodiments, the emulsifying or wetting agent component is present in amount of about 1% to about 40% by weight of the formulation. In some embodiments, the emulsifying or wetting agent component is present in amount of about 1% to about 30% by weight of the formulation. In some embodiments, the emulsifying or wetting agent component is present in amount of about 1% to about 20% by weight of the formulation. In some embodiments, the emulsifying or wetting agent component is present in amount of about 2% to about 20% by weight of the formulation. In some embodiments, the emulsifying or wetting agent component is present in amount of about 5% to about 20% by weight of the formulation.

In some embodiments, the emulsifying or wetting agent component comprises one or more non-ionic emulsifying agents and emulsifying waxes, or combinations thereof. In some embodiments, the emulsifying or wetting agent component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., polyethylene glycol hexadecyl ether (Cetomacrogol 1000), polyethylene glycol octadecyl ether (Brij S2), polyoxyethylene stearyl ether (Brij S721)), and emulsifying waxes (Polawax)), or combinations thereof.

In some embodiments, the oil phase comprises one or more stabilizing agents. In some embodiments, the one or more stabilizing agents comprises one or more substances independently selected from polysaccharides. In some embodiments, the one or more stabilizing agents is xanthan gum.

In some embodiments, the formulation comprises a solvent component. In some embodiments, the solvent component is present in amount of about 5% to about 60% by weight of the formulation. In some embodiments, the solvent component is present in amount of about 5% to about 50% by weight of the formulation. In some embodiments, the solvent component is present in amount of about 10% to about 60% by weight of the formulation. In some embodiments, the solvent component is present in amount of about 10% to about 50% by weight of the formulation. In some embodiments, the solvent component is present in amount of about 10% to about 40% by weight of the formulation.

In some embodiments, the solvent component comprises one or more hydroxylated solvents. In some embodiments, the solvent component comprises one or more substances selected from dimethyl glycol, diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the solvent component comprises about 0.1% to about 20% of glycerol by weight of the formulation. In some embodiments, the solvent component comprises about 1% to about 20% of glycerol by weight of the formulation. In some embodiments, the solvent component comprises about 5% to about 20% of glycerol by weight of the formulation. In some embodiments, the solvent component comprises about 10% to about 20% of glycerol by weight of the formulation.

In some embodiments, the formulation comprises one or more chelating agents. In some embodiments, the chelating agent is EDTA.

In some embodiments, the formulation comprises one or more preservatives. In some embodiments, the one or more preservatives are benzyl alcohol, methyl paraben, propyl paraben, phenoxyethanol, and combinations thereof.

Lotions

In some embodiments, the formulation is a lotion formulation. In some embodiments, the formulation is an aqueous lotion formulation. In some embodiments, the lotion formulation is an oil-in-water emulsion. In some embodiments, the lotion formulation comprises water and an oil component. In some embodiments, the lotion formulation comprises water, a solvent component, and an oil component. In some embodiments, the oil component comprises an emulsifying or wetting agent component. In some embodiments, the oil component comprises one or more stabilizing agents.

In some embodiments, the water is present in an amount of about 10% to about 90% by weight of the formulation. In some embodiments, the water is present in an amount of about 10% to about 80% by weight of the formulation. In some embodiments, the water is present in an amount of about 10% to about 70% by weight of the formulation. In some embodiments, the water is present in an amount of about 10% to about 60% by weight of the formulation. In some embodiments, the water is present in an amount of about 20% to about 90% by weight of the formulation. In some embodiments, the water is present in an amount of about 20% to about 80% by weight of the formulation. In some embodiments, the water is present in an amount of about 20% to about 70% by weight of the formulation. In some embodiments, the water is present in an amount of about 25% to about 60% by weight of the formulation. In some embodiments, the water is present in an amount of about 30% to about 60% by weight of the formulation.

In some embodiments, the oil component is present in an amount of about 5% to about 60% by weight of the formulation. In some embodiments, the oil component is present in an amount of about 5% to about 50% by weight of the formulation. In some embodiments, the oil component is present in an amount of about 10% to about 60% by weight of the formulation. In some embodiments, the oil component is present in an amount of about 10% to about 50% by weight of the formulation. In some embodiments, the oil component is present in an amount of about 10% to about 40% by weight of the formulation. In some embodiments, the oil component is present in an amount of about 10% to about 30% by weight of the formulation.

In some embodiments, the oil component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters (isopropyl myristate), glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), polyoxyethylene stearyl ether (Brij S721)), waxes (e.g., paraffin (soft white paraffin), emulsifying waxes (Polawax)), mineral, natural, hydrogenated, and silicone oils (e.g., light mineral oil, castor oil, silicone oils (e.g., cyclomethicone, dimethicone), hydrogenated castor oils (Kolliphor HCO), and triglycerides (caprylic/capric triglyceride (Crodamol GTCC), medium chain triglycerides), or combinations thereof. In some embodiments, the oil component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), xanthan gum, vegetable or animal fat (e.g., cocoa butter), vegetable wax (e.g., Carnauba wax), and wax ester (e.g., bees wax), or combinations thereof.

In some embodiments, the emulsifying or wetting agent component is present in amount of about 1% to about 40% by weight of the formulation. In some embodiments, the emulsifying or wetting agent component is present in amount of about 1% to about 30% by weight of the formulation. In some embodiments, the emulsifying or wetting agent component is present in amount of about 1% to about 20% by weight of the formulation. In some embodiments, the emulsifying or wetting agent component is present in amount of about 2% to about 20% by weight of the formulation. In some embodiments, the emulsifying or wetting agent component is present in amount of about 5% to about 20% by weight of the formulation.

In some embodiments, the emulsifying or wetting agent component comprises one or more non-ionic emulsifying agents and emulsifying waxes, or combinations thereof. In some embodiments, the emulsifying or wetting agent component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., polyethylene glycol hexadecyl ether (Cetomacrogol 1000), polyethylene glycol octadecyl ether (Brij S2), polyoxyethylene stearyl ether (Brij S721)), and emulsifying waxes (Polawax)), or combinations thereof.

In some embodiments, the oil phase comprises one or more stabilizing agents. In some embodiments, the one or more stabilizing agents comprises one or more substances independently selected from polysaccharides. In some embodiments, the one or more stabilizing agents is xanthan gum.

In some embodiments, the formulation comprises a solvent component. In some embodiments, the solvent component is present in amount of about 5% to about 70% by weight of the formulation. In some embodiments, the solvent component is present in amount of about 5% to about 60% by weight of the formulation. In some embodiments, the solvent component is present in amount of about 5% to about 50% by weight of the formulation. In some embodiments, the solvent component is present in amount of about 10% to about 70% by weight of the formulation. In some embodiments, the solvent component is present in amount of about 10% to about 60% by weight of the formulation. In some embodiments, the solvent component is present in amount of about 10% to about 50% by weight of the formulation. In some embodiments, the solvent component is present in amount of about 10% to about 40% by weight of the formulation.

In some embodiments, the solvent component comprises one or more hydroxylated solvents. In some embodiments, the solvent component comprises one or more substances selected from dimethyl glycol, diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the solvent component comprises about 0.1% to about 20% of glycerol by weight of the formulation. In some embodiments, the solvent component comprises about 1% to about 20% of glycerol by weight of the formulation. In some embodiments, the solvent component comprises about 5% to about 20% of glycerol by weight of the formulation. In some embodiments, the solvent component comprises about 10% to about 20% of glycerol by weight of the formulation.

In some embodiments, the formulation comprises one or more chelating agents. In some embodiments, the chelating agent is EDTA.

In some embodiments, the formulation comprises one or more preservatives. In some embodiments, the one or more preservatives are benzyl alcohol, methyl paraben, propyl paraben, phenoxyethanol, and combinations thereof.

Foams and Foamable Formulations

In some embodiments, the formulation is a foamable formulation. In some embodiments, the formulation is an aqueous foam or foamable formulation. In some embodiments, the foam or foamable formulation comprises a base component and a propellant component. In some embodiments, the base component is an oil-in-water emulsion. In some embodiments, the propellant phase comprises one or more hydrofluorocarbons (HFCs) or hydrofluoroolefins (HFOs). In some embodiments, the propellant phase comprises one or more hydrofluorocarbons (HFCs). In some embodiments, the propellant phase comprises one or more hydrofluoroolefins (HFOs). In some embodiment, the propellant phase comprises HFA-134. In some embodiment, the propellant phase comprises HFO-1234ze.

In some embodiments, the base component is present in an amount of about 50% to about 98% of the formulation. In some embodiments, the base component is present in an amount of about 50% to about 95% of the formulation. In some embodiments, the base component is present in an amount of about 60% to about 95% of the formulation. In some embodiments, the base component is present in an amount of about 70% to about 95% of the formulation. In some embodiments, the base component is present in an amount of about 75% to about 98% of the formulation. In some embodiments, the base component is present in an amount of about 75% to about 95% of the formulation. In some embodiments, the base component is present in an amount of about 80% to about 90% of the formulation.

In some embodiments, the propellant phase is present in an amount of about 2% to about 50% of the formulation. In some embodiments, the propellant phase is present in an amount of about 5% to about 50% of the formulation. In some embodiments, the propellant phase is present in an amount of about 5% to about 40% of the formulation. In some embodiments, the propellant phase is present in an amount of about 5% to about 30% of the formulation. In some embodiments, the propellant phase is present in an amount of about 2% to about 25% of the formulation. In some embodiments, the propellant phase is present in an amount of about 5% to about 25% of the formulation. In some embodiments, the propellant phase is present in an amount of about 10% to about 20% of the formulation.

In some embodiments, the base component comprises water and an oil component. In some embodiments, the base component comprises water, a solvent component, and an oil component. In some embodiments, the oil component comprises an emulsifying or wetting agent component. In some embodiments, the oil component comprises one or more stabilizing agents.

In some embodiments, the water is present in an amount of about 10% to about 90% by weight of the base component. In some embodiments, the water is present in an amount of about 10% to about 80% by weight of the base component. In some embodiments, the water is present in an amount of about 10% to about 70% by weight of the base component. In some embodiments, the water is present in an amount of about 10% to about 60% by weight of the base component. In some embodiments, the water is present in an amount of about 10% to about 50% by weight of the base component. In some embodiments, the water is present in an amount of about 20% to about 80% by weight of the base component. In some embodiments, the water is present in an amount of about 20% to about 70% by weight of the base component. In some embodiments, the water is present in an amount of about 20% to about 60% by weight of the base component. In some embodiments, the water is present in an amount of about 25% to about 50% by weight of the base component.

In some embodiments, the oil component is present in an amount of about 3% to about 60% by weight of the base component. In some embodiments, the oil component is present in an amount of about 5% to about 60% by weight of the base component. In some embodiments, the oil component is present in an amount of about 5% to about 50% by weight of the base component. In some embodiments, the oil component is present in an amount of about 5% to about 40% by weight of the base component. In some embodiments, the oil component is present in an amount of about 5% to about 30% by weight of the base component. In some embodiments, the oil component is present in an amount of about 10% to about 60% by weight of the base component. In some embodiments, the oil component is present in an amount of about 10% to about 50% by weight of the base component. In some embodiments, the oil component is present in an amount of about 10% to about 40% by weight of the base component. In some embodiments, the oil component is present in an amount of about 10% to about 30% by weight of the base component.

In some embodiments, the oil component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters (isopropyl myristate), glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), polyoxyethylene stearyl ether (Brij S721), ethoxylated stearic and cetyl alcohols (Kolliphor CS20)), waxes (e.g., paraffin (soft white paraffin), emulsifying waxes (Polawax)), mineral, natural, hydrogenated, and silicone oils (e.g., light mineral oil, castor oil, silicone oils (e.g., cyclomethicone, dimethicone), hydrogenated castor oils (Kolliphor HCO), fatty ester (cocoyl caprylocaprate (Kollicream 3C)), and triglycerides (caprylic/capric triglyceride (Crodamol GTCC), medium chain triglycerides), or combinations thereof. In some embodiments, the oil component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), xanthan gum, vegetable or animal fat (e.g., cocoa butter), vegetable wax (e.g., Carnauba wax), and wax ester (e.g., bees wax), or combinations thereof.

In some embodiments, the oil component comprises an emulsifier or stabilizer component, or an emulsifier or wetting agent component.

In some embodiments, the emulsifying or wetting agent component is present in amount of about 1% to about 40% by weight of the base component. In some embodiments, the emulsifying or wetting agent component is present in amount of about 1% to about 30% by weight of the base component. In some embodiments, the emulsifying or wetting agent component is present in amount of about 1% to about 20% by weight of the base component. In some embodiments, the emulsifying or wetting agent component is present in amount of about 2% to about 20% by weight of the base component. In some embodiments, the emulsifying or wetting agent component is present in amount of about 5% to about 20% by weight of the base component. In some embodiments, the emulsifying or wetting agent component is present in amount of about 10% to about 20% by weight of the base component.

In some embodiments, the emulsifying or wetting agent component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), polyoxyethylene stearyl ether (Brij S721), ethoxylated stearic and cetyl alcohols (Kolliphor CS20)), and emulsifying waxes (Polawax)). In some embodiments, the emulsifying or wetting agent component comprises one or more substances selected from fatty alcohols (e.g., cetyl alcohol, stearyl alcohol, and cetostearyl alcohol (such as Kolliphor CSA50)), fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), and polyoxyethylene stearyl ether (Brij S721), ethoxylated stearic and cetyl alcohols (Kolliphor CS20)).

In some embodiments, the oil phase comprises one or more stabilizing agents. In some embodiments, the one or more stabilizing agents comprises one or more substances independently selected from polysaccharides. In some embodiments, the one or more stabilizing agents is xanthan gum.

In some embodiments, the base component comprises a solvent component. In some embodiments, the solvent component is present in amount of about 5% to about 70% by weight of the base component. In some embodiments, the solvent component is present in amount of about 5% to about 60% by weight of the base component. In some embodiments, the solvent component is present in amount of about 5% to about 50% by weight of the base component. In some embodiments, the solvent component is present in amount of about 10% to about 70% by weight of the base component. In some embodiments, the solvent component is present in amount of about 10% to about 60% by weight of the base component. In some embodiments, the solvent component is present in amount of about 10% to about 50% by weight of the base component. In some embodiments, the solvent component is present in amount of about 10% to about 40% by weight of the base component. In some embodiments, the solvent component is present in amount of about 20% to about 70% by weight of the base component. In some embodiments, the solvent component is present in amount of about 20% to about 60% by weight of the base component. In some embodiments, the solvent component is present in amount of about 20% to about 50% by weight of the base component.

In some embodiments, the solvent component comprises one or more hydroxylated solvents. In some embodiments, the solvent component comprises one or more substances selected from dimethyl glycol, diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the solvent component comprises about 0.1% to about 20% of glycerol by weight of the base component. In some embodiments, the solvent component comprises about 1% to about 20% of glycerol by weight of the base component. In some embodiments, the solvent component comprises about 5% to about 20% of glycerol by weight of the base component. In some embodiments, the solvent component comprises about 10% to about 20% of glycerol by weight of the base component.

In some embodiments, the base component comprises one or more chelating agents. In some embodiments, the chelating agent is EDTA.

In some embodiments, the base component comprises one or more preservatives. In some embodiments, the one or more preservatives are benzyl alcohol, methyl paraben, propyl paraben, phenoxyethanol, and combinations thereof.

Sprays

In some embodiments, the formulation is a spray (e.g., a pump spray). In some embodiments, the formulation is an aqueous spray formulation. In some embodiments, the spray formulation comprises water, a solvent component, and a volatile excipient. In some embodiments, the spray formulation comprises water, a solvent component, a volatile excipient, and a film-forming component.

In some embodiments, the spray formulation comprises water, a solvent component, a volatile excipient, a film forming agent, and a preservative component. In some embodiments, the spray formulation comprises water, a solvent component, a volatile excipient, a film forming agent, a preservative component, and a chelating agent.

In some embodiments, the water is present in an amount of about 5% to about 65% by weight of the spray formulation. In some embodiments, the water is present in an amount of about 10% to about 70% by weight of the formulation. In some embodiments, the water is present in an amount of about 10% to about 60% by weight of the formulation. In some embodiments, the water is present in an amount of about 15% to about 50% by weight of the formulation. In some embodiments, the water is present in an amount of about 5% to about 60% by weight of the base component. In some embodiments, the water is present in an amount of about 5% to about 50% by weight of the formulation. In some embodiments, the water is present in an amount of about 10% to about 65% by weight of the formulation. In some embodiments, the water is present in an amount of about 10% to about 50% by weight of the formulation. In some embodiments, the water is present in an amount of about 15% to about 65% by weight of the formulation. In some embodiments, the water is present in an amount of about 15% to about 60% by weight of the formulation.

In some embodiments, the solvent component is present in an amount of about 1% to about 40% by weight of the formulation. In some embodiments, the solvent component is present in an amount of about 5% to about 40% by weight of the formulation. In some embodiments, the solvent component is present in an amount of about 5% to about 35% by weight of the formulation. In some embodiments, the solvent component is present in an amount of about 5% to about 30% by weight of the formulation. In some embodiments, the solvent component is present in an amount of about 10% to about 40% by weight of the formulation. In some embodiments, the solvent component is present in an amount of about 10% to about 35% by weight of the formulation. In some embodiments, the solvent component is present in an amount of about 10% to about 30% by weight of the formulation. In some embodiments, the solvent component is present in an amount of about 15% to about 40% by weight of the formulation. In some embodiments, the solvent component is present in an amount of about 15% to about 35% by weight of the formulation. In some embodiments, the solvent component is present in an amount of about 15% to about 30% by weight of the formulation. In some embodiments, the solvent component is present in an amount of about 15% to about 25% by weight of the formulation.

In some embodiments, the solvent component comprises one or more hydroxylated solvents. In some embodiments, the solvent component comprises one or more substances selected from sorbitol, dimethyl glycol, diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the volatile excipient is present in an amount of about 20% to about 90% by weight of the formulation. In some embodiments, the volatile excipient is present in an amount of about 30% to about 90% by weight of the formulation. In some embodiments, the volatile excipient is present in an amount of about 35% to about 85% by weight of the formulation. In some embodiments, the volatile excipient is present in an amount of about 40% to about 80% by weight of the formulation. In some embodiments, the volatile excipient is present in an amount of about 45% to about 75% by weight of the formulation. In some embodiments, the volatile excipient is present in an amount of about 45% to about 75% by weight of the formulation. In some embodiments, the volatile excipient is present in an amount of about 50% to about 70% by weight of the formulation. In some embodiments, the volatile excipient is present in an amount of about 30% to about 85% by weight of the formulation. In some embodiments, the volatile excipient is present in an amount of about 30% to about 80% by weight of the formulation. In some embodiments, the volatile excipient is present in an amount of about 30% to about 75% by weight of the formulation. In some embodiments, the volatile excipient is present in an amount of about 30% to about 70% by weight of the formulation.

In some embodiments, the volatile excipient comprises one or more alcohols. In some embodiments, the volatile excipient comprises one or more small alkyl chain alcohols. In some embodiments, the volatile excipient comprises ethanol.

In some embodiments, the spray formulation comprises a film forming component. In some embodiments, the film forming component comprises one or more film forming agents. In some embodiments, the film forming component is present in amount of about 0.1% to about 30% by weight of the formulation. In some embodiments, the film forming component is present in amount of about 0.1% to about 20% by weight of the formulation. In some embodiments, the filming forming component is present in amount of about 1% to about 30% by weight of the formulation. In some embodiments, the film forming component is present in amount of about 0.5% to about 20% by weight of the formulation. In some embodiments, the film forming component is present in amount of about 0.1% to about 15% by weight of the formulation. In some embodiments, the film forming component is present in amount of about 0.1% to about 5% by weight of the formulation.

In some embodiments, the film forming component comprises one or more film forming polymers. In some embodiments, the film forming component comprises one or more film forming cationic copolymers. In some embodiments, the film forming component comprises one or more film forming non-ionic polymers. In some embodiments, the film forming component comprises one or more film forming anionic copolymers. In some embodiments, the film forming component comprises one or more film forming agents selected from polyvinypyrrolidine, a cationic methacrylate polymer (e.g., Eudragit 100), hydrophilic non-ionic surfactant (e.g., Poloxamer 407 which is a triblock copolymer consisting of polypropylene glycol flanked by two hydrophilic blocks of polyethylene glycol), and a copolymer of monoalkyl ester of poly (methyl vinyl ether/maleic acid) (e.g., Gantres™ ES-435). In some embodiments, the filming forming component comprises cationic copolymer of dimethylaminoethyl methacrylate, butyl methacrylate, and methyl methacrylate with a ratio of 2:1:1 (Eudragit E 100), a polyethylene glycol-copolypropylene glycol-co-polyethylene glycol triblock copolymer (e.g., a poloxamer such as poloxamer 407), or a copolymer of monoalkyl ester of poly(methyl vinyl ether/maleic acid) (e.g., Gantrez ES-435), or a combination thereof.

In some embodiments, the spray formulation comprises one or more preservatives. In some embodiments, the one or more preservatives are benzyl alcohol, methyl paraben, propyl paraben, phenoxyethanol, butylated hydroxytoluene (BHT), and combinations thereof.

In some embodiments, the spray formulation comprises one or more chelating agents. In some embodiments, the chelating agent is EDTA.

In some embodiments, the spray formulation is a propellant spray formulation. In some embodiments, the propellant spray formulation comprises one or more of a solvent, a volatile excipient, a film forming polymer, and a propellant. In some embodiments, the propellant spray formulation does not comprise water. The solvents, volatile excipients, and film forming polymers are those as described above for the pump sprays.

In some embodiments, the propellant spray formulation comprises one or more solvent component. In some embodiments, the solvent component is present in an amount of about 0.5% to about 10% by weight of the formulation. In some embodiments, the solvent component is present in an amount of about 0.5% to about 5% by weight of the formulation. In some embodiments, the solvent component is present in an amount of about 0.5% to about 1% by weight of the formulation.

In some embodiments, the propellant spray formulation comprises one or more film-forming polymer. In some embodiments, the film-forming polymer is present in an amount of about 0.5% to about 10% by weight of the formulation. In some embodiments, the film-forming polymer is present in an amount of about 0.5% to about 5% by weight of the formulation. In some embodiments, the film-forming polymer is present in an amount of about 0.5% to about 1% by weight of the formulation.

In some embodiments, the propellant spray formulation comprises one or more volatile excipient. In some embodiments, the volatile excipient is present in an amount of about 5% to about 35% by weight of the formulation. In some embodiments, the volatile excipient is present in an amount of about 10% to about 30% by weight of the formulation. In some embodiments, the volatile excipient is present in an amount of about 15% to about 30% by weight of the formulation.

In some embodiments, the propellant spray formulation comprises one or more propellant. In some embodiments, the propellant comprises one or more hydrofluorocarbons (HFCs) or hydrofluoroolefins (HFOs). In some embodiments, the propellant comprises one or more hydrofluorocarbons (HFCs). In some embodiments, the propellant comprises one or more hydrofluoroolefins (HFOs). In some embodiment, the propellant comprises HFA-134. In some embodiment, the propellant comprises HFO-1234ze. In some embodiments, the propellant is present in an amount of about 10% to about 90% of the formulation. In some embodiments, the propellant is present in an amount of about 10% to about 95% of the formulation. In some embodiments, the propellant is present in an amount of about 20% to about 80% of the formulation. In some embodiments, the propellant phase is present in an amount of about 30% to about 80% of the formulation.

Aqueous Gels

In some embodiments, the formulation is an aqueous gel. In some embodiments, the aqueous gel comprises water, a solvent component, a stabilizing component, and a gelling agent component. In some embodiments, the aqueous gel formulation comprises water, a solvent component, a stabilizing component, a gelling agent component, and a preservative. In some embodiments, the aqueous gel formulation comprises water, a solvent component, a stabilizing component, a gelling agent component, a preservative, and a chelating agent.

In some embodiments, the water is present in an amount of about 10% to about 80% by weight of the formulation. In some embodiments, the water is present in an amount of about 10% to about 70% by weight of the formulation. In some embodiments, the water is present in an amount of about 10% to about 60% by weight of the formulation. In some embodiments, the water is present in an amount of about 20% to about 70% by weight of the formulation. In some embodiments, the water is present in an amount of about 20% to about 60% by weight of the formulation. In some embodiments, the water is present in an amount of about 30% to about 50% by weight of the formulation.

In some embodiments, the formulation comprises a solvent component. In some embodiments, the solvent component is present in amount of about 5% to about 95% by weight of the formulation. In some embodiments, the solvent component is present in amount of about 10% to about 95% by weight of the formulation. In some embodiments, the solvent component is present in amount of about 20% to about 95% by weight of the formulation. In some embodiments, the solvent component is present in amount of about 25% to about 90% by weight of the formulation. In some embodiments, the solvent component is present in amount of about 30% to about 85% by weight of the formulation. In some embodiments, the solvent component is present in amount of about 35% to about 85% by weight of the formulation. In some embodiments, the solvent component is present in amount of about 20% to about 90% by weight of the formulation. In some embodiments, the solvent component is present in amount of about 20% to about 85% by weight of the formulation.

In some embodiments, the solvent component comprises one or more hydroxylated solvents. In some embodiments, the solvent component comprises one or more substances selected from diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the stabilizing component is present in an amount of about 0.05% to about 10% by weight of the formulation. In some embodiments, the stabilizing component is present in an amount of about 0.05% to about 8% by weight of the formulation. In some embodiments, the stabilizing component is present in an amount of about 0.5% to about 8% by weight of the formulation. In some embodiments, the stabilizing component is present in an amount of about 1% to about 6% by weight of the formulation.

In some embodiments, the stabilizing component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), or polyethylene glycol fatty ethers (e.g., polyoxylcastor oil, polyethylene glycol hexadecyl ether (Cetomacrogol 1000), diethylene glycol monoethyl ether (Transcutol P), polyethylene glycol octadecyl ether (Brij S2), polyoxyethylene stearyl ether (Brij S721)), or combinations thereof.

In some embodiments, the aqueous gel formulation comprises a gelling agent component. In some embodiments, the gelling agent component comprises hydroxyethyl cellulose, hypermellose, hydroxypropyl cellulose, and combinations thereof.

In some embodiments, the aqueous gel formulation comprises one or more preservatives. In some embodiments, the one or more preservatives are benzyl alcohol, methyl paraben, propyl paraben, butylated hydroxytoluene (BHT), phenoxyethanol, and combinations thereof.

In some embodiments, the aqueous gel formulation comprises one or more chelating agents. In some embodiments, the chelating agent is EDTA.

Non Aqueous Gels

In some embodiments, the formulation is a non-aqueous gel formulation. In some embodiments, the non-aqueous gel formulation comprises a solvent component. In some embodiments, the non-aqueous gel formulation comprises a solvent component and a gelling agent component. In some embodiments, the non-aqueous gel formulation comprises a solvent component and a volatile excipient. In some embodiments, the non-aqueous gel formulation comprises a solvent component, a volatile excipient, and a preservative. In some embodiments, the non-aqueous gel formulation comprises a solvent component, a volatile excipient, a preservative, and a gelling agent component.

In some embodiments, the formulation comprises a solvent component. In some embodiments, the solvent component is present in amount of about 60% to about 99% by weight of the formulation. In some embodiments, the solvent component is present in amount of about 65% to about 99% by weight of the formulation. In some embodiments, the solvent component is present in amount of about 70% to about 99% by weight of the formulation. In some embodiments, the solvent component is present in amount of about 75% to about 99% by weight of the formulation. In some embodiments, the solvent component comprises one or more hydroxylated solvents. In some embodiments, the solvent component comprises one or more substances selected from diethylene glycol diethers (e.g., diethylene glycol monoethyl ether (Transcutol P)), glycerol, alkylene glycols (e.g., propylene glycol, hexylene glycol), or polyethylene glycols (e.g., PEG400), and glycerol.

In some embodiment, the formulation comprises a volatile excipient. In some embodiments, the volatile excipient is a solvent for the ruxolitinib, or a pharmaceutically acceptable salt thereof. In some embodiments, the volatile excipient is present in an amount of about 1% to about 60% by weight of the formulation. In some embodiments, the volatile excipient is present in an amount of about 1% to about 50% by weight of the formulation. In some embodiments, the volatile excipient is present in an amount of about 1% to about 40% by weight of the formulation. In some embodiments, the volatile excipient is present in an amount of about 10% to about 40% by weight of the formulation. In some embodiments, the volatile excipient is present in an amount of about 10% to about 35% by weight of the base component. In some embodiments, the volatile excipient is present in an amount of about 10% to about 30% by weight of the formulation. In some embodiments, the volatile excipient is present in an amount of about 15% to about 30% by weight of the formulation. In some embodiments, the volatile excipient is present in an amount of about 15% to about 40% by weight of the formulation. In some embodiments, the volatile excipient is present in an amount of about 15% to about 35% by weight of the formulation. In some embodiments, the volatile excipient comprises one or more alcohols. In some embodiments, the volatile excipient comprises ethanol.

In some embodiments, the formulation comprises one or more preservatives. In some embodiments, the one or more preservatives are benzyl alcohol, methyl paraben, propyl paraben, phenoxyethanol, and combinations thereof.

In some embodiments, the non-aqueous gel formulation comprises a gel forming component. In some embodiments, the gel forming component comprises hydroxyethyl cellulose, hypermellose, hydroxypropyl cellulose, and combinations thereof.

Emulsified Gels

In some embodiments, the formulation is an emulsified gel formulation. In some embodiments, the emulsified gel formulation comprises water, a solvent component, and an oil component. In some embodiments, the oil component comprises an emulsifier component. In some embodiments, the emulsified gel formulation comprises water, a solvent component, an oil component, an emulsifier component, and a chelating agent. In some embodiments, the emulsified gel formulation comprises water, a solvent component, an oil component, an emulsifier component, a chelating agent, and a preservative component.

In some embodiments, the water is present in an amount of about 10% to about 80% by weight of the formulation. In some embodiments, the water is present in an amount of about 10% to about 70% by weight of the formulation. In some embodiments, the water is present in an amount of about 10% to about 60% by weight of the formulation. In some embodiments, the water is present in an amount of about 20% to about 70% by weight of the formulation. In some embodiments, the water is present in an amount of about 20% to about 60% by weight of the formulation. In some embodiments, the water is present in an amount of about 30% to about 50% by weight of the formulation. In some embodiments, the water is present in an amount of about 40%.

In some embodiments, the oil component is present in an amount of about 5% to about 60% by weight of the formulation. In some embodiments, the oil component is present in an amount of about 10% to about 60% by weight of the formulation. In some embodiments, the oil component is present in an amount of about 10% to about 50% by weight of the formulation. In some embodiments, the oil component is present in an amount of about 10% to about 40% by weight of the formulation. In some embodiments, the oil component is present in an amount of about 10% to about 30% by weight of the formulation.

In some embodiments, the oil component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters (isopropyl myristate), glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., polyethoxyl castor oil, polyethylene glycol hexadecyl ether (Cetomacrogol 1000), diethylene glycol monoethyl ether (Transcutol P), polyethylene glycol octadecyl ether (Brij S2), polyoxyethylene stearyl ether (Brij S721)), waxes (e.g., paraffin (soft white paraffin), emulsifying waxes (Polawax)), mineral, natural, hydrogenated, and silicone oils (e.g., light mineral oil, castor oil, silicone oils (e.g., cyclomethicone, dimethicone), hydrogenated castor oils (Kolliphor HCO), acrylamide/sodium acryloyldimethyl taurate copolymer (e.g., Sepino P600), and triglycerides (caprylic/capric triglyceride (Crodamol GTCC), medium chain triglycerides), or combinations thereof. In some embodiments, the oil component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), xanthan gum, vegetable or animal fat (e.g., cocoa butter), vegetable wax (e.g., Carnauba wax), and wax ester (e.g., bees wax), or combinations thereof.

In some embodiments, the emulsifier component is present in amount of about 1% to about 30% by weight of the formulation. In some embodiments, the emulsifier component is present in amount of about 2% to about 30% by weight of the formulation. In some embodiments, the emulsifier component is present in amount of about 1% to about 20% by weight of the formulation. In some embodiments, the emulsifier component is present in amount of about 5% to about 30% by weight of the formulation. In some embodiments, the emulsifier component is present in amount of about 5% to about 20% by weight of the formulation. In some embodiments, the emulsifier component is present in amount of about 0.5% to about 10% by weight of the formulation. In some embodiments, the emulsifying or wetting agent component is present in amount of about 0.5% to about 8% by weight of the formulation. In some embodiments, the emulsifying or wetting agent component is present in amount of about 0.5% to about 5% by weight of the formulation. In some embodiments, the emulsifying or wetting agent component is present in amount of about 1% to about 5% by weight of the formulation.

In some embodiments, the emulsifier component comprises one or more non-ionic emulsifying agents and emulsifying waxes, or combinations thereof. In some embodiments, the emulsifying or wetting agent component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., polyethylene glycol hexadecyl ether (Cetomacrogol 1000), polyethylene glycol octadecyl ether (Brij S2), polyoxyethylene stearyl ether (Brij S721)), and emulsifying waxes (Polawax)), Polyoxyl castor oil and polyoxyl hydrogenated castor oil (polyoxyl 35 castor oil) or combinations thereof.

In some embodiments, the formulation comprises a solvent component. In some embodiments, the solvent component is present in amount of about 5% to about 60% by weight of the formulation. In some embodiments, the solvent component is present in amount of about 5% to about 50% by weight of the formulation. In some embodiments, the solvent component is present in amount of about 10% to about 60% by weight of the formulation. In some embodiments, the solvent component is present in amount of about 10% to about 50% by weight of the formulation. In some embodiments, the solvent component is present in amount of about 10% to about 40% by weight of the formulation.

In some embodiments, the solvent component comprises one or more hydroxylated solvents. In some embodiments, the solvent component comprises one or more substances selected from diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the formulation comprises one or more chelating agents. In some embodiments, the chelating agent is EDTA.

In some embodiments, the formulation comprises one or more preservatives. In some embodiments, the one or more preservatives are benzyl alcohol, methyl paraben, propyl paraben, phenoxyethanol, and combinations thereof.

Methods of Treating

The present disclosure is further directed to methods of treating a skin disease in a patient in need thereof, comprising topically administering to an affected area of the patient a topical formulation comprising a JAK 1/2 inhibitor, which is ruxolitinib, or a pharmaceutically acceptable salt thereof, and an organic amine pH adjusting agent. The present disclosure also provides methods, wherein the organic amine pH adjusting agent is a tertiary amine. The present disclosure also provides for methods, wherein the JAK1/2 inhibitor, or a pharmaceutically acceptable salt thereof, is ruxolitinib phosphate. The present disclosure also provides for methods, the skin disease is an autoimmune or an inflammatory skin disease.

The present disclosure also provides for methods, wherein a synergistic effect occurs between the JAK1/2 inhibitor, or the pharmaceutically acceptable salt thereof, and the amine pH adjusting agent.

The present disclosure also provides for methods, wherein the pharmaceutical formulation is administered at least one time per day. The present disclosure also provides for methods, wherein the pharmaceutical formulation is administered at least two times per day.

The present disclosure also provides for methods, wherein the topical formulation is in a form chosen from a cream, a lotion, a foam or foamable formulation, a spray (e.g., a pump spray), an aqueous gel, a non-aqueous gel, and an emulsified gel The present disclosure also provides for methods, wherein the topical formulation is a cream or a lotion.

Skin Diseases

The present disclosure also provides methods for treating a skin disease in a patient in need thereof, comprising topically administering to an affected area of the patient a topical formulation comprising a JAK 1/2 inhibitor, which is ruxolitinib, or a pharmaceutically acceptable salt thereof, and an organic amine pH adjusting agent. In some embodiments, the skin disease is an autoimmune skin disease.

In some embodiments, the skin disease is an inflammatory skin disease.

In some embodiments, the skin disease is associated with Th1 or Th2. T helper (Th)1 and/or T helper (Th)17 cells are involved in many inflammatory and autoimmune skin diseases. For example, the following diseases are primarily Th17 biased: (i) psoriasis (Fletcher, et al., *Clin Exp Immunol*, 201(2):121-134 (2020) at PMID: 32379344; Liu, et al., *Front Immunol*, 11:594735 (2020) at PMID: 33281823); (ii) ichthyosis (Czarnowicki, et al., *J Invest Dermatol*, 138(10): 2157-2167 (2018) at PMID: 29660300; Paller, et al, *J Allergy Clin Immunol*, 139(1):152-165 (2017) at PMID: 27554821); and (iii) pityriasis rubra pilaris (Liu, supra, at PMID: 33281823). Further, the following diseases are primarily Th1 biased: (i) alopecia areata (Żeberkiewicz, et al., *Cent Eur J Immunol*, 45(3):325-333 (2020) at PMID: 33437185; and (ii) vitiligo (Boniface, et al., *Clin Rev Allergy Immunol*, 54(1):52-67 (2018) at PMID: 28685247). Some diseases are associated with both Th1 and Th17, including: (i) hidradenitis suppurativa (Fletcher, supra, at PMID: 32379344; Liu, supra, at PMID: 33281823; Banerjee, et al., *Immunol Invest*, 46(2):149-158 (2017) at PMID: 27819528; Moran, et al., *J Invest Dermatol*, 137(11):2389-2395 (2017) at PMID: 28652108); and (ii) cutaneous lichen planus (Aghamajidi, et al., *Scand J Immunol*, e13000 (2020) at PMID: 33190330). Further, blocking of inflammatory cytokines, such as IL-22 and CXCL10 which are involved in Th1 or Th17 lymphocyte proliferation, survival and function, can be useful for treating Th1 or Th17 associated diseases. For example, T helper (Th)17 cells are a distinct lineage of effector CD4+ T cells characterized by their production of IL-17. See Liang, et al., *J Exp Med*, 203(10):2271-9 (2006) at PMID: 16982811. Th17 cells have been shown to express IL-22 at substantially higher amounts than Th1 or Th2 cells. Further, expansion of IL-22-producing cells is dependent on IL-23. In turn, blocking IL-17 and IL-23 are clinically validated approaches in psoriasis. Examples of this approach in treating psoriasis, a Th17 associated disease, include secukinumab and guselkumab, which block blocking IL-17 and IL-23, respectively. T helper (Th)1 cells are a distinct lineage of effector CD4+ T cells characterized by their production of IFN-gamma and T-bet transcriptional marker. See Szabo, et al., *Cell*, 100(6):655-69 (2000) at PMID: 10761931. CXCL10, also known as interferon gamma-induced protein 10 (IP-10), attracts lymphocytes to the skin. Further, CXCR3 is the receptor for the CXCL10 ligand. In turn, diseases such as vitiligo appear to be Th1 associated, as lymphocyte infiltration into vitiliginous skin is thought to be driven by CXCR3-positive Th1 cells responding to the CXCL10 ligand.

In some embodiments, the skin disease is mediated by interleukin 22 (IL-22), C—X—C motif chemokine 10 (CXCL10), matrix metallopeptidase 12 (MMP12), or a combination thereof. In some embodiments, the skin disease is mediated by IL-22. In some embodiments, the skin disease is mediated by MMP12. In some embodiments, the skin disease is mediated by CXCL10.

In some embodiments, the skin disease is mediated by Defb4, S100a12, or Serpinb4. S100a12 is a significant marker for psoriasis disease activity (Wilsmann-Theis, D, et al., J Eur Acad Dermatol Venereol, 30(7):1165-70 (2016); doi: 10.1111/jdv.13269, which is incorporated herein by reference in its entirety). Defb4 encodes human beta-defensin 2(hBD2), an antimicrobial peptide that plays an essentially role in inflammatory processes in the skin and is important in the pathogenesis of psoriasis (Johansen C, et al., J Invest Derm, 136(8):1608-1616 (2016); doi: 10.1016/j.jid.2016.04.012, which is incorporated herein by reference in its entirety). Serpinb4 contributes to inflammation in patients with chronic skin diseases, including atopic dermatitis (Sivaprasad, U, et al., J Invest Derm 135(1):160-169 (2015); DOI:10.1038/jid.2014.353, which is incorporated herein by reference in its entirety).

In some embodiments, the skin disease is selected from psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, ichthyosis, prurigo nodularis, lichen planus, and a disorder of keratinization.

In some embodiments, the skin disease is selected from psoriasis, atopic dermatitis, alopecia, vitiligo, Reiter's syndrome, pityriasis rubra pilaris, epidermolysis bullosa simplex, palmoplantar keratoderma, pachyonychia congenita, steatocystoma multiplex, cutaneous lichen planus, cutaneous T-cell lymphoma, hidradenitis suppurativa, contact dermatitis, prurigo nodularis, lichen planus, and ichthyosis.

In some embodiments, the skin disease is psoriasis. In some embodiments, the psoriasis is mediated by interleukin 22 (IL-22), C—X—C motif chemokine 10 (CXCL10), matrix metallopeptidase 12 (MMP12), or a combination thereof. The nexus between psoriasis and IL-22, CXCL10, and/or MMP12 can be found, for example, at IL-22, CXCL10, and/or MMP12, see He et al. "Tape strips detect distinct immune and barrier profiles in atopic dermatitis and psoriasis" J Allergy Clin Immunol. 2020 Jul. 9; S0091-6749 (20)30824-1, PMID: 32709423, which is incorporated by reference in its entirety herein. In some embodiments, the psoriasis is mediated by interleukin 22 (IL-22). In some embodiments, the psoriasis is mediated by C—X—C motif chemokine 10 (CXCL10). In some embodiments, the psoriasis is mediated by matrix metallopeptidase 12 (MMP12). In some embodiments, the psoriasis is selected from plaque psoriasis, nail psoriasis, intertriginous psoriasis, palmoplantar psoriasis, and pustular psoriasis. In some embodiments, the psoriasis is plaque psoriasis. In some embodiments, the plaque psoriasis is mediated by interleukin 22 (IL-22). In some embodiments, the plaque psoriasis is mediated by C—X—C motif chemokine 10 (CXCL10). In some embodiments, the plaque psoriasis is mediated by matrix metallopeptidase 12 (MMP12).

In some embodiments, the skin disease is atopic dermatitis. In some embodiments, the atopic dermatitis is mediated by interleukin 22 (IL-22), C—X—C motif chemokine 10 (CXCL10), matrix metallopeptidase 12 (MMP12), or a combination thereof. The nexus between atopic dermatitis and IL-22 and/or MMP12 can be found, for example, at He et al. "Tape strips detect distinct immune and barrier profiles in atopic dermatitis and psoriasis" J Allergy Clin Immunol. 2020 Jul. 9; S0091-6749(20)30824-1, PMID: 32709423. The nexus between atopic dermatitis and CXCL10 can be found, for example, at Brunner et al. "Nonlesional atopic dermatitis skin shares similar T-cell clones with lesional tissues" Allergy. 2017 December; 72(12):2017-2025, PMID: 28599078. Each of the references cited herein is incorporated by reference in its entirety herein. In some embodiments, the atopic dermatitis is mediated by interleukin 22 (IL-22). In some embodiments, the atopic dermatitis is mediated by C—X—C motif chemokine 10 (CXCL10). In some embodiments, the atopic dermatitis is mediated by matrix metallopeptidase 12 (MMP12).

In some embodiments, the skin disease is alopecia. In some embodiments, the skin disease is alopecia areata. The nexus between alopecia areata and IL-22 can be found, for example, at Loh et al. "Role of T helper 17 cells and T regulatory cells in alopecia areata: comparison of lesion and serum cytokine between controls and patients" J Eur Acad Dermatol Venereol. 2018 June; 32(6):1028-1033, PMID: 29283462. The nexus between alopecia areata and CXCL10 can be found, for example, at Duca et al. "Frontal fibrosing alopecia shows robust T helper 1 and Janus kinase 3 skewing" Br J Dermatol. 2020 Mar. 25, PMID: 32215911. Each of the references cited herein is incorporated by reference in its entirety herein. In some embodiments, the alopecia is mediated by interleukin 22 (IL-22). In some embodiments, the alopecia is mediated by C—X—C motif chemokine 10 (CXCL10).

In some embodiments, the skin disease is vitiligo. The nexus between vitiligo and IL-22 can be found, for example, at Czarnowicki et al. "Blood endotyping distinguishes the profile of vitiligo from that of other inflammatory and autoimmune skin diseases" J Allergy Clin Immunol. 2019 June; 143(6):2095-2107. PMID: 30576756. The nexus between vitiligo and CXCL10 can be found, for example, at Abdallah et al. "CXCL-10 and Interleukin-6 are reliable serum markers for vitiligo activity: A multicenter cross-sectional study" Pigment Cell Melanoma Res. 2018 March; 31(2):330-336. PMID: 29094481. Each of the references cited herein is incorporated by reference in its entirety herein. In some embodiments, the vitiligo is mediated by interleukin 22 (IL-22). In some embodiments, the vitiligo is mediated by C—X—C motif chemokine 10 (CXCL10).

In some embodiments, the skin disease is Reiter's syndrome. The nexus between Reiter's syndrome and IL-22 can be found, for example, at Zhao et al. "IL-22+CD4+ T cells in patients with rheumatoid arthritis" Int J Rheum Dis. 2013 October; 16(5):518-26, PMID: 24164838. The nexus between Reiter's syndrome and CXCL10 can be found, for example, at Pandya et al. "Blood chemokine profile in untreated early rheumatoid arthritis: CXCL10 as a disease activity marker" Arthritis Res Ther. 2017 Feb. 2; 19(1):20, PMID: 28148302. Each of the references cited herein is incorporated by reference in its entirety herein. In some embodiments, the Reiter's syndrome is mediated by interleukin 22 (IL-22). In some embodiments, the Reiter's syndrome is mediated by C—X—C motif chemokine 10 (CXCL10).

In some embodiments, the skin disease is pityriasis rubra pilaris. The nexus between pityriasis rubra pilaris and IL-22 can be found, for example, at Feldmeyer et al. "Interleukin 23-Helper T Cell 17 Axis as a Treatment Target for Pityriasis Rubra Pilaris" JAMA Dermatol. 2017 Apr. 1; 153(4):304-308, PMID: 28122069. The nexus between pityriasis rubra pilaris and CXCL10 can be found, for example, at Adnot-Desanlis et al. "Effectiveness of infliximab in pityriasis rubra pilaris is associated with pro-inflammatory cytokine inhibition" Dermatology 2013; 226(1):41-6, PMID: 23548788. Each of the references cited herein is incorporated by reference in its entirety herein. In some embodiments, the pityriasis rubra pilaris is mediated by interleukin 22 (IL-22). In some embodiments, the pityriasis rubra pilaris is mediated by C—X—C motif chemokine 10 (CXCL10).

In some embodiments, the skin disease is epidermolysis bullosa simplex. The nexus between epidermolysis bullosa simplex and IL-22 and/or CXCL10 can be found, for example, at Castela et al. "Epidermolysis bullosa simplex generalized severe induces a T helper 17 response and is improved by apremilast treatment" Br J Dermatol. 2019 February; 180(2):357-364, PMID: 29932457, which is incorporated by reference in its entirety herein. In some embodiments, the epidermolysis bullosa simplex is mediated by interleukin 22 (IL-22). In some embodiments, the epidermolysis bullosa simplex is mediated by C—X—C motif chemokine 10 (CXCL10).

In some embodiments, the skin disease is palmoplantar keratoderma. The nexus between almoplantar keratoderma and IL-22 can be found, for example, at Druetz et al. "Association of Transient Palmoplantar Keratoderma With Clinical and Immunologic Characteristics of Bullous Pemphigoid" JAMA Dermatol. 2019 Feb. 1; 155(2):216-220, PMID: 30484821, which is incorporated by reference in its entirety herein. In some embodiments, the palmoplantar keratoderma is mediated by interleukin 22 (IL-22).

In some embodiments, the skin disease is pachyonychia congenita. The nexus between pachyonychia congenita and IL-22 can be found, for example, at Yang et al. "Keratin 17 in disease pathogenesis: from cancer to dermatoses" J Pathol. 2019 February; 247(2):158-165, PMID: 30306595, which is incorporated by reference in its entirety herein. In some embodiments, the pachyonychia congenita is mediated by interleukin 22 (IL-22).

In some embodiments, the skin disease is steatocystoma multiplex. The nexus between steatocystoma multiplex and IL-22 can be found, for example, at Yang et al. "Keratin 17 in disease pathogenesis: from cancer to dermatoses" J Pathol. 2019 February; 247(2):158-165, PMID: 30306595, which is incorporated by reference in its entirety herein. In some embodiments, the steatocystoma multiplex is mediated by interleukin 22 (IL-22).

In some embodiments, the skin disease is cutaneous lichen planus. The nexus between cutaneous lichen planus and IL-22 can be found, for example, at Chen et al. "Immunoexpression of interleukin-22 and interleukin-23 in oral and cutaneous lichen planus lesions: a preliminary study" Mediators Inflamm. 2013; 2013:801974, PMID: 24376306. The nexus between cutaneous lichen planus and CXCL10 can be found, for example, at Domingues et al. "The dysfunctional innate immune response triggered by Toll-like receptor activation is restored by TLR7/TLR8 and TLR9 ligands in cutaneous lichen planus" Br J Dermatol. 2015 January; 172(1):48-55, PMID: 24976336 and Wenzel et al. "CXCR3<-> ligand-mediated skin inflammation in cutaneous lichenoid graft-versus-host disease" J Am Acad Dermatol. 2008 March; 58(3):437-42, PMID: 18280341, each of which is incorporated by reference in its entirety herein. In some embodiments, the cutaneous lichen planus is mediated by interleukin 22 (IL-22). In some embodiments, the cutaneous lichen planus is mediated by C—X—C motif chemokine 10 (CXCL10).

In some embodiments, the skin disease is cutaneous T-cell lymphoma. In some embodiments, the cutaneous T-cell lymphoma is mediated by interleukin 22 (IL-22), C—X—C motif chemokine 10 (CXCL10), matrix metallopeptidase 12 (MMP12), or a combination thereof. The nexus between cutaneous T-cell lymphoma and IL-22 and/or MMP12 can be found, for example, at Litvinov et al. "The Use of Transcriptional Profiling to Improve Personalized Diagnosis and Management of Cutaneous T-cell Lymphoma (CTCL)" Clin Cancer Res. 2015 Jun. 15; 21(12):2820-9, PMID: 25779945. The nexus between cutaneous T-cell lymphoma and CXCL10 can be found, for example, at Mehul et al. "Proteomic analysis of stratum corneum in Cutaneous T-Cell Lymphomas and psoriasis" Exp Dermatol. 2019 March; 28(3):317-321, PMID: 30637808. Each of the references cited herein is incorporated by reference in its entirety herein. In some embodiments, the cutaneous T-cell lymphoma is mediated by interleukin 22 (IL-22). In some embodiments, the cutaneous T-cell lymphoma is mediated by C—X—C motif chemokine 10 (CXCL10). In some embodiments, the cutaneous T-cell lymphoma is mediated by matrix metallopeptidase 12 (MMP12).

In some embodiments, the skin disease is hidradenitis suppurativa. The nexus between hidradenitis suppurativa and IL-22 can be found, for example, at Rumberger et al. "Transcriptomic analysis of hidradenitis suppurativa skin suggests roles for multiple inflammatory pathways in disease pathogenesis" Inflamm Res. 2020 October; 69(10):967-973, PMID: 32661800, which is incorporated by reference in its entirety herein. In some embodiments, the hidradenitis suppurativa is mediated by interleukin 22 (IL-22).

In some embodiments, the skin disease is contact dermatitis. In some embodiments, the contact dermatitis is mediated by interleukin 22 (IL-22), C—X—C motif chemokine 10 (CXCL10), matrix metallopeptidase 12 (MMP12), or a combination thereof. The nexus between contact dermatitis and IL-22 can be found, for example, at Robb et al. "Prostaglandin E 2 stimulates adaptive IL-22 production and promotes allergic contact dermatitis" J Allergy Clin Immunol. 2018 January; 141(1):152-162, PMID: 28583370. The nexus between contact dermatitis and CXCL10 can be found, for example, at Brans et al. "Stratum corneum levels of inflammatory mediators and natural moisturizing factor in patch test reactions to thiurams and fragrances and their possible role in discrimination between irritant and allergic reactions to hapten mixtures" Contact Dermatitis. 2020 Nov. 21, PMID: 33222241. The nexus between contact dermatitis and MMP12 can be found, for example, at Meguro et al. "SOCS3 Expressed in M2 Macrophages Attenuates Contact Hypersensitivity by Suppressing MMP-12 Production" J Invest Dermatol. 2016 March; 136(3):649-657, PMID: 27015453. Each of the references cited herein is incorporated by reference in its entirety herein. In some embodiments, the contact dermatitis is mediated by interleukin 22 (IL-22). In some embodiments, the contact dermatitis is mediated by C—X—C motif chemokine 10 (CXCL10). In some embodiments, the contact dermatitis is mediated by matrix metallopeptidase 12 (MMP12).

In some embodiments, the skin disease is ichthyosis. The nexus between ichthyosis and IL-22 can be found, for example, at Czarnowicki et al. "The Major Orphan Forms of Ichthyosis Are Characterized by Systemic T-Cell Activation and Th-17/Tc-17/Th-22/Tc-22 Polarization in Blood" J Invest Dermatol. 2018 October; 138(10):2157-2167, PMID: 29660300, which is incorporated by reference in its entirety herein. In some embodiments, the ichthyosis is mediated by interleukin 22 (IL-22). In some embodiments, the ichthyosis is ichthyosis vulgaris, x-linked ichthyosis, bullous congenital ichthyosiform erythroderma (BCIE), nonbullous congenital ichthyosiform erythroderma (NBCIE), lamellar ichthyosis, harlequin ichthyosis, ichthyosis syndrome, or acquired ichthyosis.

Generally, disorders of keratinization are a group of disorders of cornification. The nexus between a disorder of keratinization and IL-22 can be found, for example, at Yang et al. "Keratin 17 in disease pathogenesis: from cancer to dermatoses" J Pathol. 2019 February; 247(2):158-165, PMID: 30306595, which is incorporated by reference in its entirety herein. In some embodiments, the disorder of keratinization is mediated by IL-22. In some embodiments, the disorder of keratinization is selected from ichthyosis, palmoplantar keratoderma, keratosis pilari, and acantholytic dermatosis.

In some embodiments, the skin disease is rosacea, psoriatic arthritis, dermal fibrosis, morphea, spitz nevi, dermatophytosis, or acne vulgaris. In some embodiments, the skin disease is rosacea. In some embodiments, the rosacea is mediated by interleukin 22 (IL-22) or C—X—C motif chemokine 10 (CXCL10), or a combination thereof. The nexus between rosacea and IL-22 and CXCL10 can be found, for example, see Buhl, et al., J. Invest. Derm., 135(9), P2198-2208 (2015), PMID: 25848978, which is incorporated by reference in its entirety herein. In some embodiments, the rosacea is mediated by interleukin 22 (IL-22). In some embodiments, the psoriasis is rosacea by C—X—C motif chemokine 10 (CXCL10). In some embodiments, the skin disease is psoriasis mediated by S100a12. In some embodiments, the skin disease is psoriatic arthritis mediated by S100a12. In some embodiments, the skin disease is dermal fibrosis mediated by S100a12. In some embodiments, the skin disease is morphea mediated by S100a12. In some embodiments, the skin disease is atopic dermatitis mediated by S100a12. In some embodiments, the skin disease is spitz nevi mediated by S100a12.

In some embodiments, the skin disease is psoriasis mediated by Defb4. In some embodiments, the skin disease is psoriatic arthritis mediated by Defb4. In some embodiments, the skin disease is dermatophytosis mediated by Defb4. In some embodiments, the skin disease is acne vulgaris mediated by Defb4. In some embodiments, the skin disease is hidradenitis suppurativa mediated by Defb4.

In some embodiments, the skin disease is psoriasis mediated by Serpinb4. In some embodiments, the skin disease is psoriatic arthritis mediated by Serpinb4.

In some embodiments, the ruxolitinib or the salt thereof is administered as a topical formulation. In some embodiments, the topical formulation comprises from about 0.05% to about 3.0%, or about 0.05% to about 1.5% by weight of the formulation on a free base basis of the ruxolitinib, or the pharmaceutically acceptable salt thereof. In some embodiments, the topical formulation comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis of the ruxolitinib, or the pharmaceutically acceptable salt thereof. In some embodiments, the topical formulation comprises from about 0.5% to about 1.5% by weight of the formulation on a free base basis of the ruxolitinib, or the pharmaceutically acceptable salt thereof. In some embodiments, ruxolitinib is ruxolitinib phosphate.

In some embodiments, as disclosed above, the amine pH adjusting agent is a tertiary amine. In some embodiments, the organic amine pH adjusting agent is an alkanol amine. In some embodiments, the alkanol amine is a di- or tri-alkanolamine. In some embodiments, as disclosed above, the amine pH adjusting agent is independently selected from trolamine, tris, ethanolamine, diethanolamine, ammonia, diisopropanolamine, 1-amino-2-propanol, 2-amino-2-ethyl-1,3-propanediol, 2-amino-2-methyl-1-propanol, diisopropylamine, imidazole, and pyridine.

In some embodiments, the amine pH adjusting agent is trolamine.

In some embodiments, pH adjustment of the formulation to >5.5% with trolamine increased drug loading to >8% w/w.

In some embodiments, the amine pH adjusting agent is present in an amount to adjust the pH of the formulation, wherein the formulation has a pH of from about 5.0 to about 8.0, from about 5.5 to about 7.5, or from about 5.5 to about 7.0. In some embodiments, the amine pH adjusting agent is present in an amount up to 11% w/w or up to 2.6% w/w. Further for example, in some embodiments, the amine pH adjusting agent is present in an amount from about 0.25% to about 0.5%, from about 0.5% to about 0.75%, from about 0.75% to about 1%, from about 1% to about 1.25%, from about 1.25% to about 1.5%, from about 1.5% to about 1.75%, from about 1.75% to about 2%, from about 2% to about 2.25%, from about 2.25% to about 2.5%, from about 2.5% to about 2.6%, from about 2.6% to about 2.75%, from about 2.75% to about 3%, from about 3% to about 4%, from about 4% to about 5%, from about 5% to about 6%, from about 6% to about 7%, from about 7% to about 8%, from about 8% to about 9%, from about 9% to about 10%, from about 10% to about 11%, w/w, by weight of the formulation.

In some embodiments, there is a synergistic effect between the JAK 1/2 inhibitor, or the pharmaceutically acceptable salt thereof, and the organic amine pH adjusting agent.

The present disclosure also provides for pharmaceutical formulations, wherein the formulation has a pH of from about 5.0 to about 8.0, from about 5.5 to about 7.5, or from about 5.5 to about 7.0.

In some embodiments, provided are the methods as described herein, wherein the JAK 1/2 inhibitor, or the pharmaceutically acceptable salt thereof, is administered in a therapeutically effective amount.

In some embodiments of each of the aforementioned, the patient is a human patient.

Formulations Having Water and Ethanol

The present disclosure further provides a topical formulation for treating a skin disease comprising a JAK 1/2 inhibitor, which is ruxolitinib, or a pharmaceutically acceptable salt thereof, water and ethanol. In some embodiments, the JAK 1/2 inhibitor is a pharmaceutically acceptable salt of ruxolitinib. In some embodiments, the JAK 1/2 inhibitor, or a pharmaceutically acceptable salt thereof, is ruxolitinib phosphate. In some embodiments, the JAK 1/2 inhibitor, or a pharmaceutically acceptable salt thereof, is ruxolitinib sulfate. In some embodiments, the JAK 1/2 inhibitor, or a pharmaceutically acceptable salt thereof, is ruxolitinib maleate.

In some embodiments, the ruxolitinib, or the pharmaceutically acceptable salt thereof is present in an amount from about 0.05% to about 3.0% or about 0.05% to about 1.5% w/w of the ruxolitinib, or a pharmaceutically acceptable salt thereof, on a free base basis. Further for example, the present disclosure provides for the formulation which comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis.

The present disclosure provides for the formulation which is in a form chosen from a cream, a lotion, a foam or foamable formulation, a spray (e.g., a pump spray), an aqueous gel, a non-aqueous gel, and an emulsified gel. The present disclosure provides for the formulation which is a cream or a lotion. In some embodiments, the formulation is a spray formulation (e.g., a pump spray formulation).

In some embodiments, the ethanol comprises about 20% to about 90% by weight of the formulation. In some embodiments, the ethanol comprises about 30% to about 90% by weight of the formulation. In some embodiments, the ethanol comprises about 30% to about 80% by weight of the formulation. In some embodiments, the ethanol comprises about 40% to about 80% by weight of the formulation. In some embodiments, the ethanol comprises about 30% to about 90% by weight of the formulation. In some embodiments, the ethanol comprises about 40% to about 90% by weight of the formulation.

In some embodiments, the formulation further comprises an organic pH adjusting agent. In some embodiments, the organic amine pH adjusting agent is a tertiary amine. In some embodiments, the organic amine pH adjusting agent is an alkanol amine. In some embodiments, the alkanol amine is a di- or tri-alkanolamine. In some embodiments, the organic amine pH adjusting agent is independently selected from trolamine, tris, ethanolamine, diethanolamine, ammonia, diisopropanolamine, 1-amino-2-propanol, 2-amino-2-ethyl-1,3-propanediol, 2-amino-2-methyl-1-propanol, diisopropylamine, imidazole, and pyridine. In some embodiments, the amine pH adjusting agent is trolamine.

In some embodiments, the formulation is a spray formulation. In some embodiments, the formulation comprises water, a solvent component, and ethanol. In some embodiments, the spray formulation comprises water, a solvent component, ethanol, and a film-forming component.

In some embodiments, the water is present in an amount of about 5% to about 65% by weight of the formulation. In some embodiments, the water is present in an amount of about 10% to about 70% by weight of the formulation. In some embodiments, the water is present in an amount of about 10% to about 60% by weight of the formulation. In some embodiments, the water is present in an amount of about 15% to about 50% by weight of the formulation. In some embodiments, the water is present in an amount of about 5% to about 60% by weight of the formulation. In some embodiments, the water is present in an amount of about 5% to about 50% by weight of the formulation. In some embodiments, the water is present in an amount of about 10% to about 65% by weight of the formulation. In some embodiments, the water is present in an amount of about 10% to about 50% by weight of the formulation. In some embodiments, the water is present in an amount of about 15% to about 65% by weight of the formulation. In some embodiments, the water is present in an amount of about 15% to about 60% by weight of the formulation.

In some embodiments, the solvent component is present in an amount of about 1% to about 40% by weight of the formulation. In some embodiments, the solvent component is present in an amount of about 5% to about 40% by weight of the formulation. In some embodiments, the solvent component is present in an amount of about 5% to about 35% by weight of the formulation. In some embodiments, the solvent component is present in an amount of about 5% to about 30% by weight of the formulation. In some embodiments, the solvent component is present in an amount of about 10% to about 40% by weight of the formulation. In some embodiments, the solvent component is present in an amount of about 10% to about 35% by weight of the formulation. In some embodiments, the solvent component is present in an amount of about 10% to about 30% by weight of the formulation. In some embodiments, the solvent component is present in an amount of about 15% to about 40% by weight of the formulation. In some embodiments, the solvent component is present in an amount of about 15% to about 35% by weight of the formulation. In some embodiments, the solvent component is present in an amount of about 15% to about 30% by weight of the formulation. In some embodiments, the solvent component is present in an amount of about 15% to about 25% by weight of the formulation.

In some embodiments, the solvent component comprises one or more hydroxylated solvents. In some embodiments, the solvent component comprises one or more substances selected from sorbitol, diethylene glycol diethers (e.g., diethylene glycol monoethyl ether (Transcutol P)), glycerol, alkylene glycols (e.g., propylene glycol), or polyethylene glycols (e.g., PEG400).

In some embodiments, the ethanol is present in an amount of about 20% to about 90% by weight of the formulation. In some embodiments, the ethanol is present in an amount of about 30% to about 90% by weight of the formulation. In some embodiments, the ethanol is present in an amount of about 35% to about 85% by weight of the formulation. In some embodiments, the ethanol is present in an amount of about 40% to about 80% by weight of the formulation. In some embodiments, the ethanol is present in an amount of about 45% to about 75% by weight of the formulation. In some embodiments, the ethanol is present in an amount of about 45% to about 75% by weight of the formulation. In some embodiments, the ethanol is present in an amount of about 50% to about 70% by weight of the formulation. In some embodiments, the ethanol is present in an amount of about 30% to about 85% by weight of the formulation. In some embodiments, the ethanol is present in an amount of about 30% to about 80% by weight of the formulation. In some embodiments, the ethanol is present in an amount of about 30% to about 75% by weight of the formulation. In some embodiments, the ethanol is present in an amount of about 30% to about 70% by weight of the formulation.

In some embodiments, the formulation comprises a film forming component. In some embodiments, the film forming component comprises one or more film forming agents. In some embodiments, the film forming component is present in amount of about 0.1% to about 30% by weight of the formulation. In some embodiments, the film forming component is present in amount of about 0.1% to about 20% by weight of the formulation. In some embodiments, the filming forming component is present in amount of about 1% to about 30% by weight of the formulation. In some embodiments, the film forming component is present in amount of about 0.5% to about 20% by weight of the formulation. In some embodiments, the film forming component is present in amount of about 0.1% to about 15% by weight of the formulation. In some embodiments, the film forming component is present in amount of about 0.1% to about 5% by weight of the formulation.

In some embodiments, the film forming component comprises one or more film forming polymers. In some embodiments, the film forming component comprises one or more film forming cationic copolymers. In some embodiments, the film forming component comprises one or more film forming non-ionic polymers. In some embodiments, the film forming component comprises one or more film forming anionic copolymers. In some embodiments, the film forming component comprises one or more film forming agents selected from polyvinypyrrolidine, a cationic methacrylate polymer (e.g., Eudragit 100), hydrophilic non-ionic surfactant (e.g., Poloxamer 407 which is a triblock copolymer consisting of polypropylene glycol flanked by two hydrophilic blocks of polyethylene glycol), and a copolymer of monoalkyl ester of poly (methyl vinyl ether/maleic acid) (e.g., Gantres™ ES-435). In some embodiments, the filming forming component comprises cationic copolymer of dimethylaminoethyl methacrylate, butyl methacrylate, and methyl methacrylate with a ratio of 2:1:1 (Eudragit E 100), a polyethylene glycol-copolypropylene glycol-co-polyethylene glycol triblock copolymer (e.g., a poloxamer such as poloxamer 407), or a copolymer of monoalkyl ester of poly(methyl vinyl ether/maleic acid) (e.g., Gantrez ES-435), or a combination thereof.

In some embodiments, the formulation comprises one or more preservatives. In some embodiments, the one or more preservatives are benzyl alcohol, methyl paraben, propyl paraben, phenoxyethanol, butylated hydroxytoluene (BHT), and combinations thereof.

In some embodiments, the formulation comprises one or more chelating agents. In some embodiments, the chelating agent is EDTA.

Formulations Having Glycerol and Transcutol P

The present disclosure further provides a topical formulation for treating a skin disease comprising a JAK 1/2 inhibitor, which is ruxolitinib, or a pharmaceutically acceptable salt thereof, and a solvent component, wherein a solvent component comprises glycerol and transcutol P. The present disclosure further provides a topical formulation for treating a skin disease comprising a JAK 1/2 inhibitor, which is ruxolitinib, or a pharmaceutically acceptable salt thereof, water, and a solvent component, wherein the solvent component comprises glycerol and transcutol P. In some embodiments, the JAK 1/2 inhibitor is a pharmaceutically acceptable salt of ruxolitinib. In some embodiments, the JAK 1/2 inhibitor, or a pharmaceutically acceptable salt thereof, is ruxolitinib phosphate. In some embodiments, the JAK 1/2 inhibitor, or a pharmaceutically acceptable salt thereof, is ruxolitinib sulfate. In some embodiments, the JAK 1/2 inhibitor, or a pharmaceutically acceptable salt thereof, is ruxolitinib maleate.

In some embodiments, the ruxolitinib, or the pharmaceutically acceptable salt thereof is present in an amount from about 0.05% to about 3.0% or about 0.05% to about 1.5% w/w of the ruxolitinib, or a pharmaceutically acceptable salt thereof, on a free base basis. Further for example, the present disclosure provides for the formulation which comprises about 0.05%, about 0.06%, about 0.07%, about 0.08%, about 0.09%, about 0.1%, about 0.15%, about 0.2%, about 0.25%, about 0.3%, about 0.35%, about 0.4%, about 0.45%, about 0.5%, about 0.55%, about 0.6%, about 0.65%, about 0.7%, about 0.75%, about 0.8%, about 0.85%, about 0.9%, about 0.95%, about 1.0%, about 1.05%, about 1.1%, about 1.15%, about 1.2%, about 1.25%, about 1.3%, about 1.35%, about 1.4%, about 1.45%, about 1.5%, about 1.55%, about 1.6%, about 1.65%, about 1.7%, about 1.75%, about 1.8%, about 1.85%, about 1.9%, about 1.95%, about 2.0%, about 2.5%, or about 3.0% by weight of the formulation on a free base basis.

The present disclosure provides for the formulation which is in a form chosen from a cream, a lotion, a foam or foamable formulation, a spray (e.g., a pump spray), an aqueous gel, a non-aqueous gel, and an emulsified gel. The present disclosure provides for the formulation which is a cream or a lotion. In some embodiments, the formulation is a spray formulation (e.g., a pump spray formulation).

In some embodiments, the solvent component comprises glycerol in an amount from about 10% to about 90% by weight of the component and transcutol P in an amount of about 10% to about 90% by weight of the component. In some embodiments, the solvent component comprises glycerol in an amount from about 20% to about 80% by weight of the component and transcutol P in an amount of about 20% to about 80% by weight of the component. In some embodiments, the solvent component comprises glycerol in an amount from about 30% to about 70% by weight of the component and transcutol P in an amount of about 30% to about 70% by weight of the component. In some embodiments, the solvent component comprises glycerol in an amount from about 40% to about 60% by weight of the component and transcutol P in an amount of about 40% to about 60% by weight of the component. In some embodiments, the ratio of glycerol:transcutol is about 1:1.

In some embodiments, the formulation further comprises an organic pH adjusting agent. In some embodiments, the organic amine pH adjusting agent is a tertiary amine. In some embodiments, the organic amine pH adjusting agent is an alkanol amine. In some embodiments, the alkanol amine is a di- or tri-alkanolamine. In some embodiments, the organic amine pH adjusting agent is independently selected from trolamine, tris, ethanolamine, diethanolamine, ammonia, diisopropanolamine, 1-amino-2-propanol, 2-amino-2-ethyl-1,3-propanediol, 2-amino-2-methyl-1-propanol, diisopropylamine, imidazole, and pyridine. In some embodiments, the amine pH adjusting agent is trolamine.

In some embodiments, the formulation is a lotion formulation. In some embodiments, the formulation is an aqueous lotion formulation. In some embodiments, the lotion formulation is an oil-in-water emulsion. In some embodiments, the lotion formulation comprises water and an oil component. In some embodiments, the lotion formulation comprises water, a solvent component, and an oil component. In some embodiments, the oil component comprises an emulsifying or wetting agent component. In some embodiments, the oil component comprises one or more stabilizing agents.

In some embodiments, the water is present in an amount of about 10% to about 90% by weight of the formulation. In some embodiments, the water is present in an amount of about 10% to about 80% by weight of the formulation. In some embodiments, the water is present in an amount of about 10% to about 70% by weight of the formulation. In some embodiments, the water is present in an amount of about 10% to about 60% by weight of the formulation. In some embodiments, the water is present in an amount of about 20% to about 90% by weight of the formulation. In some embodiments, the water is present in an amount of about 20% to about 80% by weight of the formulation. In some embodiments, the water is present in an amount of about 20% to about 70% by weight of the formulation. In some embodiments, the water is present in an amount of about 25% to about 60% by weight of the formulation. In some embodiments, the water is present in an amount of about 30% to about 60% by weight of the formulation.

In some embodiments, the oil component is present in an amount of about 5% to about 60% by weight of the formulation. In some embodiments, the oil component is present in an amount of about 5% to about 50% by weight of the formulation. In some embodiments, the oil component is present in an amount of about 10% to about 60% by weight of the formulation. In some embodiments, the oil component is present in an amount of about 10% to about 50% by weight of the formulation. In some embodiments, the oil component is present in an amount of about 10% to about 40% by weight of the formulation. In some embodiments, the oil component is present in an amount of about 10% to about 30% by weight of the formulation.

In some embodiments, the oil component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., PEG 100 stearate (component of Arlacel 165), polyethylene glycol hexadecyl ether (Cetomacrogol 1000), polyethylene glycol octadecyl ether (Brij S2), polyoxyethylene stearyl ether (Brij S721)), waxes (e.g., paraffin (soft white paraffin), emulsifying waxes (Polawax)), mineral, natural, hydrogenated, and silicone oils (e.g., light mineral oil, castor oil, silicone oils (e.g., cyclomethicone, dimethicone), hydrogenated castor oils (Kolliphor HCO), and triglycerides (caprylic/capric triglyceride (Crodamol GTCC), medium chain triglycerides), or combinations thereof. In some embodiments, the oil component comprises one or more substances selected from fatty acids (e.g., lanolin acid), fatty alcohols (e.g., lanolin alcohol), hydrocarbon oils & waxes (e.g., petrolatum), polyhydric alcohols (e.g., propylene glycol), silicones (e.g., dimethicone), sterols (e.g., cholesterol), vegetable or animal fat (e.g., cocoa butter), vegetable wax (e.g., Carnauba wax), and wax ester (e.g., bees wax), or combinations thereof.

In some embodiments, the emulsifying or wetting agent component is present in amount of about 1% to about 40% by weight of the formulation. In some embodiments, the emulsifying or wetting agent component is present in amount of about 1% to about 30% by weight of the formulation. In some embodiments, the emulsifying or wetting agent component is present in amount of about 1% to about 20% by weight of the formulation. In some embodiments, the emulsifying or wetting agent component is present in amount of about 2% to about 20% by weight of the formulation. In some embodiments, the emulsifying or wetting agent component is present in amount of about 5% to about 20% by weight of the formulation.

In some embodiments, the emulsifying or wetting agent component comprises one or more non-ionic emulsifying agents and emulsifying waxes, or combinations thereof. In some embodiments, the emulsifying or wetting agent component comprises one or more substances selected from fatty alcohols (e.g., cetyl alcohol, stearyl alcohol, cetostearyl alcohol (such as Kolliphor CSA50), and octodecanol (Kolliphor OD)), fatty acids, fatty esters, glyceryl fatty esters (e.g., glyceryl monostearate (Kolliwax GMS II)), sorbitan fatty esters (e.g., polysorbate 20, polysorbate 80 (Span 80)), polyethylene glycol fatty ethers (e.g., polyethylene glycol hexadecyl ether (Cetomacrogol 1000), polyethylene glycol octadecyl ether (Brij S2), polyoxyethylene stearyl ether (Brij S721)), and emulsifying waxes (Polawax)), or combinations thereof.

In some embodiments, the oil phase comprises one or more stabilizing agents. In some embodiments, the one or more stabilizing agents comprises one or more substances independently selected from polysaccharides. In some embodiments, the one or more stabilizing agents is xanthan gum.

In some embodiments, the formulation comprises a solvent component. In some embodiments, the solvent component is present in amount of about 5% to about 70% by weight of the formulation. In some embodiments, the solvent component is present in amount of about 5% to about 60% by weight of the formulation. In some embodiments, the solvent component is present in amount of about 5% to about 50% by weight of the formulation. In some embodiments, the solvent component is present in amount of about 10% to about 70% by weight of the formulation. In some embodiments, the solvent component is present in amount of about 10% to about 60% by weight of the formulation. In some embodiments, the solvent component is present in amount of about 10% to about 50% by weight of the formulation. In some embodiments, the solvent component is present in amount of about 10% to about 40% by weight of the formulation.

In some embodiments, the solvent component further comprises one or more additional hydroxylated solvents. In some embodiments, the solvent component comprises one or more substances selected from diethylene glycol diethers (e.g., diethylene glycol monoethyl ether (Transcutol P)), alkylene glycols (e.g., propylene glycol), or polyethylene glycols (e.g., PEG400).

In some embodiments, the solvent component comprises about 0.1% to about 20% of glycerol by weight of the formulation. In some embodiments, the solvent component comprises about 1% to about 20% of glycerol by weight of the formulation. In some embodiments, the solvent component comprises about 5% to about 20% of glycerol by weight of the formulation. In some embodiments, the solvent component comprises about 10% to about 20% of glycerol by weight of the formulation.

In some embodiments, the formulation comprises one or more chelating agents. In some embodiments, the chelating agent is EDTA.

In some embodiments, the formulation comprises one or more preservatives. In some embodiments, the one or more preservatives are benzyl alcohol, methyl paraben, propyl paraben, phenoxyethanol, and combinations thereof.

Definitions

As used herein, "an affected skin area" refers to an area of the patient's skin having a skin disease as described herein.

As used herein, "ruxolitinib phosphate" means the phosphoric acid salt of ruxolitinib, wherein the ruxolitinib and phosphoric acid are in a 1:1 ratio.

As used herein, an "alkanol amine" is an $HO$—$(C_{2-6}$ alkyl$)_n$ amine, wherein n is 1, 2, or 3 and the $C_{2-6}$ alkyl groups are independently selected and can be branched or straight chain alkyl groups.

As used herein, "cream" means an emulsion, semisolid dosage form for application to the skin.

As used herein, "topical formulation," "pharmaceutical composition," or "pharmaceutical formulation" are used interchangeably and refer to compositions, and/or dosage forms, which are, within the scope of sound medical judgment, suitable for use in contact with tissues of humans and animals.

As used herein, the term "$C_{3-4}$ cycloalkyl", employed alone or in combination with other terms, refers to a non-aromatic monocyclic hydrocarbon moiety, having 3-4 carbon atoms, which may optionally contain one or more alkenylene groups as part of the ring structure. One or more ring-forming carbon atoms of a cycloalkyl group can be oxidized to form carbonyl linkages. Exemplary $C_{3-4}$ cycloalkyl groups include cyclopropyl, cyclobutyl, and the like. In some embodiments, the cycloalkyl group is cyclopropyl. In some embodiments, the cycloalkyl group is cyclobutyl.

As used herein, the term "synergy" or "synergistic effect" when used in connection with a description of the efficacy of a combination of agents or compounds, means any measured effect of the combination which is greater that the effect predicted from a sum of the effects of the individual agents or compounds.

As used herein, "statistically significant" means a p-value of <0.05 (preferably <0.001, and most preferably <0.0001).

As used herein, "apparent pH" refers to a pH value measured in the presence of an organic solvent.

As used herein, the phrase "pharmaceutically acceptable" means those compounds, materials, compositions, and/or dosage forms, which are, within the scope of sound medical judgment, suitable for use in contact with tissues of humans and animals. In some embodiments, "pharmaceutically acceptable" means approved by a regulatory agency of the Federal or a state government or listed in the U.S. Pharmacopeia or other generally recognized pharmacopeia for use in animals, and more particularly in humans.

The presently claimed subject matter also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the presently claimed subject matter include the conventional non-toxic salts of the parent compound formed, for example, from non-toxic inorganic or organic acids. The pharmaceutically acceptable salts of the presently claimed subject matter can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. In some embodiments, the pharmaceutically acceptable salt is a phosphoric acid salt, a sulfuric acid salt, or a maleic acid salt.

As used herein, the term "emulsifier component" refers, in one aspect, to a substance, or mixtures of substances that maintains an element or particle in suspension within a fluid medium. In some embodiments, the emulsifier component allows an oil phase to form an emulsion when combined with water. In some embodiments, the emulsifier component refers to one or more non-ionic surfactants.

As used herein, the term "occlusive agent component" refers to a hydrophobic agent or mixtures of hydrophobic agents that form an occlusive film on skin that reduces transepidermal water loss (TEWL) by preventing evaporation of water from the stratum corneum.

As used herein, the term "stiffening agent component" refers to a substance or mixture of substances that increases the viscosity and/or consistency of the cream or improves the rheology of the cream.

As used herein, the term "emollient component" refers to an agent that softens or soothes the skin or soothes an irritated internal surface.

As used herein, the term "stabilizing agent component" refers to a substance or mixture of substances that improves the stability of the cream and/or the compatibility of the components in the cram.

As used herein, the term "solvent component" is a liquid substance or mixture of liquid substances capable of dissolving ruxolitinib, or a pharmaceutically acceptable salt thereof, or other substances in the cream. In some embodiments, the solvent component is a liquid substance or mixture of liquid substances in which, ruxolitinib, or its pharmaceutically acceptable salt, has reasonable solubility. For example, a solvent is a substance or mixture thereof, in which ruxolitinib, or its pharmaceutically acceptable salt (whichever is used), has a solubility of at least about 0.5% or greater, 1% or greater, 10 mg/mL or greater, at least about 15 mg/mL or greater, or at least about 20 mg/mL or greater.

As used herein, the phrase "antimicrobial preservative component" is a substance or mixtures of substances, which inhibits microbial growth in the cream.

As used herein, the phrase "chelating agent component" refers to a compound or mixtures of compounds that has the ability to bind strongly with metal ions.

As used herein, "% by weight of the formulation" means the percent concentration of the component in the formulation is on weight/weight basis. For example, 1% w/w of component A=[(mass of component A)/(total mass of the formulation)]×100.

As used herein, "% by weight of the emulsion on a free base basis" of a JAK inhibitor as described herein such as ruxolitinib, or a pharmaceutically acceptable salt thereof" means that the % w/w is calculated based on the weight of ruxolitinib in the total emulsion. For example, "1.5% w/w on a free base basis" of ruxolitinib phosphate means that for 100 grams of total formulation, there are 1.98 grams of ruxolitinib phosphate in the emulsion (which equates to 1.5 grams of the free base, ruxolitinib).

As used herein, "% by weight of the formulation on a free base basis" of a JAK inhibitor as described herein such as ruxolitinib, or pharmaceutically acceptable salt thereof" means that the % w/w is calculated based on the weight of ruxolitinib in the total formulation. For example, "1.5% w/w on a free base basis" of ruxolitinib phosphate means that for 100 grams of total formulation, there are 1.98 grams of ruxolitinib phosphate in the formulation (which equates to 1.5 grams of the free base, ruxolitinib). If not already indicated in the Examples, the percentages of ruxolitinib phosphate can be converted to a free base basis by multiplying by the conversion factor of 0.7575.

As used herein, the term "component" can mean one substance or a mixture of substances.

As used herein, the term "fatty acid" refers to an aliphatic acid that is saturated or unsaturated. In some embodiments, the fatty acid is in a mixture of different fatty acids. In some embodiments, the fatty acid has between about eight to about thirty carbons on average. In some embodiments, the fatty acid has about 12 to 20, 14-20, or 16-18 carbons on average. Suitable fatty acids include, but are not limited to, cetyl acid, stearic acid, lauric acid, myristic acid, erucic acid, palmitic acid, palmitoleic acid, capric acid, caprylic acid, oleic acid, linoleic acid, linolenic acid, hydroxystearic acid, 12-hydroxystearic acid, cetostearic acid, isostearic acid, sesquioleic acid, sesqui-9-octadecanoic acid, sesquiisoocta-decanoic acid, behenic acid, isobehenic acid, and arachi-donic acid, or mixtures thereof.

As used herein, the term "fatty alcohol" refers to an aliphatic alcohol that is saturated or unsaturated. In some embodiments, the fatty alcohol is in a mixture of different fatty alcohols. In some embodiments, the fatty alcohol has between about 12 to about 20, about 14 to about 20, or about 16 to about 18 carbons on average. Suitable fatty alcohols include, but are not limited to, stearyl alcohol, lauryl alco-hol, palmityl alcohol, cetyl alcohol, capryl alcohol, caprylyl alcohol, oleyl alcohol, linolenyl alcohol, arachidonic alco-hol, behenyl alcohol, isobehenyl alcohol, selachyl alcohol, chimyl alcohol, and linoleyl alcohol, or mixtures thereof.

As used herein, the term "polyalkylene glycol", employed alone or in combination with other terms, refers to a polymer containing oxyalkylene monomer units, or copolymer of different oxyalkylene monomer units, wherein the alkylene group has 2 to 6, 2 to 4, or 2 to 3 carbon atoms. As used herein, the term "oxyalkylene", employed alone or in com-bination with other terms, refers to a group of formula —O-alkylene-. In some embodiments, the polyalkylene gly-col is polyethylene glycol.

As used herein, the term, "sorbitan fatty ester" includes products derived from sorbitan or sorbitol and fatty acids and, optionally, poly (ethylene glycol) units, including sor-bitan esters and polyethoxylated sorbitan esters. In some embodiments, the sorbitan fatty ester is a polyethoxylated sorbitan ester.

As used herein, the term "sorbitan ester" refers to a compound, or mixture of compounds, derived from the esterification of sorbitol and at least one fatty acid. Fatty acids useful for deriving the sorbitan esters include, but are not limited to, those described herein. Suitable sorbitan esters include, but are not limited to, the Span™ series (available from Uniqema), which includes Span 20 (sorbitan monolaurate), 40 (sorbitan monopalmitate), 60 (sorbitan monostearate), 65 (sorbitan tristearate), 80 (sorbitan monooleate), and 85 (sorbitan trioleate). Other suitable sorbitan esters include those listed in R. C. Rowe and P. J. Shesky, Handbook of pharmaceutical excipients, (2006), 5th ed., which is incorporated herein by reference in its entirety.

As used herein, the term "polyethoxylated sorbitan ester" refers to a compound, or mixture thereof, derived from the ethoxylation of a sorbitan ester. The polyoxethylene portion of the compound can be between the fatty ester and the sorbitan moiety. As used herein, the term "sorbitan ester" refers to a compound, or mixture of compounds, derived from the esterification of sorbitol and at least one fatty acid. Fatty acids useful for deriving the polyethoyxlated sorbitan esters include, but are not limited to, those described herein. In some embodiments, the polyoxyethylene portion of the compound or mixture has about 2 to about 200 oxyethylene units. In some embodiments, the polyoxyethylene portion of the compound or mixture has about 2 to about 100 oxyeth-ylene units. In some embodiments, the polyoxyethylene portion of the compound or mixture has about 4 to about 80 oxyethylene units. In some embodiments, the polyoxyeth-ylene portion of the compound or mixture has about 4 to about 40 oxyethylene units. In some embodiments, the polyoxyethylene portion of the compound or mixture has about 4 to about 20 oxyethylene units. Suitable polyethoxy-lated sorbitan esters include, but are not limited to the Tween™ series (available from Uniqema), which includes Tween 20 (POE(20) sorbitan monolaurate), 21 (POE(4) sorbitan monolaurate), 40 (POE(20) sorbitan monopalmi-tate), 60 (POE(20) sorbitan monostearate), 60K (POE(20) sorbitan monostearate), 61 (POE(4) sorbitan monostearate), 65 (POE(20) sorbitan tristearate), 80 (POE(20) sorbitan monooleate), 80K (POE(20) sorbitan monooleate), 81 (POE (5) sorbitan monooleate), and 85 (POE(20) sorbitan tri-oleate). As used herein, the abbreviation "POE" refers to polyoxyethylene. The number following the POE abbrevia-tion refers to the number of oxyethylene repeat units in the compound. Other suitable polyethoxylated sorbitan esters include the polyoxyethylene sorbitan fatty acid esters listed in R. C. Rowe and P. J. Shesky, Handbook of pharmaceutical excipients, (2006), 5th ed., which is incorporated herein by reference in its entirety. In some embodiments, the poly-ethoxylated sorbitan ester is a polysorbate. In some embodi-ments, the polyethoxylated sorbitan ester is polysorbate 20.

As used herein, the term "glyceryl fatty esters" refers to mono-, di- or triglycerides of fatty acids. The glyceryl fatty esters may be optionally substituted with sulfonic acid groups, or pharmaceutically acceptable salts thereof. Suit-able fatty acids for deriving glycerides of fatty acids include, but are not limited to, those described herein. In some embodiments, the glyceryl fatty ester is a mono-glyceride of a fatty acid having 12 to 18 carbon atoms. In some embodi-ments, the glyceryl fatty ester is glyceryl stearate.

As used herein, the term "triglycerides" refers to a tri-glyceride of a fatty acid. In some embodiments, the triglyc-eride is medium chain triglycerides.

As used herein, the term "alkylene glycol" refers to a group of formula —O-alkylene-, wherein the alkylene group has 2 to 6, 2 to 4, or 2 to 3 carbon atoms. In some embodiments, the alkylene glycol is propylene glycol (1,2-propanediol).

As used herein, the term "polyethylene glycol" refers to a polymer containing ethylene glycol monomer units of formula —O—$CH_2$—$CH_2$—. Suitable polyethylene glycols may have a free hydroxyl group at each end of the polymer molecule, or may have one or more hydroxyl groups etheri-fied with a lower alkyl, e.g., a methyl group. Also suitable are derivatives of polyethylene glycols having esterifiable carboxy groups. Polyethylene glycols useful in the present disclosure can be polymers of any chain length or molecular weight, and can include branching. In some embodiments, the average molecular weight of the polyethylene glycol is from about 200 to about 9000. In some embodiments, the average molecular weight of the polyethylene glycol is from about 200 to about 5000. In some embodiments, the average molecular weight of the polyethylene glycol is from about 200 to about 900. In some embodiments, the average molecular weight of the polyethylene glycol is about 400. Suitable polyethylene glycols include, but are not limited to polyethylene glycol-200, polyethylene glycol-300, polyeth-ylene glycol-400, polyethylene glycol-600, and polyethyl-ene glycol-900. The number following the dash in the name refers to the average molecular weight of the polymer.

As used herein, "contains" is equivalent to "comprises".

As used herein, the term "subject," "individual," or "patient," used interchangeably, refers to humans. In some embodiments, the "subject," "individual," or "patient" is in need of said treatment.

In some embodiments, the compounds, or pharmaceutically acceptable salts thereof, or pharmaceutical formulations thereof, topical formulations thereof, as described herein are administered in a therapeutically effective amount. As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease; or (3) preventing the disease, condition or disorder in an individual who may be predisposed to the disease, condition or disorder but does not yet experience or display the pathology or symptomatology of the disease. In some embodiments, treating refers to inhibiting or ameliorating the disease. In some embodiments, treating is preventing the disease.

In some embodiments, the components are present in exactly the ranges specified (e.g., the term "about" is not present). In some embodiments, "about" means plus or minus 10% of the value.

EXAMPLES

The presently claimed subject matter will be described in greater detail by way of specific examples. The following examples are offered for illustrative purposes and are not intended to limit the presently claimed subject matter in any manner. Those of skill in the art will readily recognize a variety of non-critical parameters, which can be changed or modified to yield essentially the same results.

Example 1: Solubility of Ruxolitinib Phosphate

The solubility of ruxolitinib phosphate in aqueous media are presented in Table 1. Ruxolitinib phosphate was substantially more soluble (ca. 1.8% w/w) in unbuffered water as compared to pH 5 or 7 water.

TABLE 1

| System | Solubility (% w/w) Ruxolitinib phosphate |
|---|---|
| Deionised water | 1.81 (1.80-1.81) |
| Buffer (pH 5)* | 0.04 (0.04-0.04) |
| Buffer (pH 7)* | 0.03 (0.03-0.03) |

Solubility (% w/w) of ruxolitinib phosphate (in terms of their salt forms) in aqueous media. Data is presented as the mean of n = 3, with the range in brackets.

*- Loaded at 0.1% w/w drug (in terms of freebase)

Example 2: Ruxolitinib Phosphate Solubility with Trolamine as a pH Adjusting Agent Unexpected, it was found that use of trolamine to adjust the pH of solvent systems improved the solubility of ruxolitinib phosphate. Various iterations of the solvent systems were assessed where trolamine (approved for topical on the FDA IID up to 2.6% w/w) was used as a pH adjusting solution instead of NaOH and the solvent system was made to volume with either water or PEG 200. The compositions of the solvent systems, their apparent pH, and the solubility of ruxolitinib phosphate in the systems has been detailed in Tables 2 and 3.

SSCR27-29 had different levels of pH adjustment, with SSCR30 being a control with no pH adjustment. SSCR31-32 have pH adjustments to 4.0 and 5.0. SSAG05 was based on SSAG01 without pH adjustment, whilst SSAG06 and SSAG07 have pH adjustments to 4.0 and 5.5, respectively. SSNA03 has a pH adjustment to 5.5.

These experiments demonstrated that as more trolamine is included in the solvent system to adjust the solvent system to >5.0 pH, the solubility of ruxolitinib phosphate increases. For example, as more trolamine is included in the solvent system to adjust the solvent system to >5.0 pH, the solubility of ruxolitinib phosphate increases in systems with low (≤25% w/w) water content (4.82% w/w drug in SSCR27 at pH 4.11, compared to ca. 11.29% w/w drug in SSCR29 at 7.27 pH). (See FIG. 1). Here, the apparent pH of the systems were maintained and an increase (or no change) in drug solubility was observed and it is believed that these would be surprising to with a person of ordinary skill in the art (POSA) based on pre-formulation data, e.g., Example 1. It is postulated, without being bound to a particular theory, that trolamine is changing the drug polymorphic form to one with a higher solubility profile, enabling a higher drug load over ca. 24 hr of stir at 20° C. than when trolamine is not included. Further, at low levels of water (<25% w/w), it was found unexpectedly that pH adjustment to >5.5% with trolamine increased drug loading to >8% w/w in some systems.

TABLE 2

Composition (% w/w) of solvent systems suitable for cream formulations.

| Excipient | SSCR27 | SSCR28 | SSCR29 | SSCR30 | SSCR31 | SSCR32 |
|---|---|---|---|---|---|---|
| Purified water | 15.00 | 15.00 | 15.00 | 15.00 | 25.00 | 25.00 |
| Polyethylene Glycol 200 | 18.88 | 18.88 | 18.88 | 37.75 | 15.45 | 15.45 |
| Propylene Glycol | 18.00 | 18.00 | 18.00 | 18.00 | 15.00 | 15.00 |
| Methyl paraben | 0.10 | 0.10 | 0.10 | 0.10 | 0.10 | 0.10 |
| Propyl paraben | 0.05 | 0.05 | 0.05 | 0.05 | 0.05 | 0.05 |
| Phenoxyethanol | 0.50 | 0.50 | 0.50 | 0.50 | 0.50 | 0.50 |
| Edetate di sodium | 0.05 | 0.05 | 0.05 | 0.05 | 0.05 | 0.05 |
| Phosphoric Acid Solution | To pH | To pH | To pH | — | To pH | To pH |
| Trolamine | 4.0 | 5.5 | 7.0 | — | 4.0 | 5.5 |
| Q.S. Polyethylene Glycol 200 | To 71.45% | | | — | To 71.59% | |
| Total | 71.45 | 71.45 | 71.45 | 71.45 | 71.59 | 71.59 |
| Saturated Solubility of ruxolitinib phosphate (free base) (% w/w) | 4.82 | 11.68 | 11.29 | 2.75 | 3.84 | 4.92 |

TABLE 2-continued

Composition (% w/w) of solvent systems suitable for cream formulations.

| Excipient | SSCR27 | SSCR28 | SSCR29 | SSCR30 | SSCR31 | SSCR32 |
|---|---|---|---|---|---|---|
| pH of Solvent System | 4.11 | 5.73 | 7.49 | 6.91 | 4.10 | 5.35 |

TABLE 2-continued

Composition (% w/w) of solvent systems suitable for cream formulations.

| Excipient | SSCR27 | SSCR28 | SSCR29 | SSCR30 | SSCR31 | SSCR32 |
|---|---|---|---|---|---|---|
| pH of Sat Sol Supernatant | 4.12 | 5.89 | 7.27 | 3.59 | 3.86 | 5.46 |

TABLE 3

Composition (% w/w) of solvent systems suitable for the inclusion in aqueous and non-aqueous gel formulations.

| Excipient | SSAG01 | SSAG05 | SSAG06 | SSAG07 | SSNA03 |
|---|---|---|---|---|---|
| Purified water | — | 10.00 | 10.00 | 10.00 | — |
| 0.1M Citrate-Phosphate Buffer pH 7.0 | 10.00 | — | — | — | — |
| Polyethylene Glycol 200 | 56.90 | 56.90 | 28.45 | 28.45 | 45.90 |
| Hexylene glycol | | — | — | — | 9.90 |
| Propylene Glycol | 15.00 | 15.00 | 15.00 | 15.00 | 18.00 |
| Transcutol P | 18.00 | 18.00 | 18.00 | 18.00 | 15.00 |
| Butylhydroxytoluene (BHT) | 0.10 | 0.10 | 0.10 | 0.10 | 0.10 |
| Phosphoric Acid Solution | — | — | to pH 4.0 | to pH 5.5 | to pH 5.5 |
| Trolamine | — | — | | | |
| Q.S. Purified water | — | — | To 100% | To 100% | To 100% |
| Total | 100.00 | 100.00 | 100.00 | 100.00 | 100.00 |
| Saturated Solubility of ruxolitinib phosphate (free base) (% w/w) | 2.778 | 2.86 | 3.90 | 11.89 | 4.96 |
| pH of Solvent System | 9.24 | 8.64 | 4.03 | 5.86 | 5.24 |
| pH of Sat Sol Supernatant | 3.90 | 3.72 | 4.06 | 5.63 | 4.37 |

Example 3: Solvent Systems for Creams, Lotions, and Foams

Solvent systems for ruxolitinib phosphate suitable for inclusion in creams, lotions and foams were investigated and are shown in Table 4. Saturated solubility data is presented as the ruxolitinib freebase, and the potential drug load in formulations represents the solubility value following adjustment for the amount of solvent system in the final formulation (assuming there is no solubility in the oil phase) and adjustment to ensure the drug is at ca. 80% of saturation. All systems were loaded at ca. 5% w/w of the ruxolitinib phosphate salt form (ca. 3.79% w/w of the freebase).

TABLE 4

Compositions (% w/w) of the solvent systems useful for cream, lotion and foam formulations.

| Excipient | Cream, lotion, and foam solvent systems | | | | |
|---|---|---|---|---|---|
| | SSCR06 | SSCR07 | SSCR28 | SSCR29 | SSCR30 |
| Water | 15.00 | 17.00 | 29.00 | 41.00 | 33.00 |
| (total water following Q.S.) | (30.14) | (33.31) | (31.17) | (44.26) | (39.32) |
| PEG 400 | 8.00 | — | 12.00 | — | — |
| Glycerol | 20.00 | 20.00 | 20.00 | 15.00 | 20.00 |
| Propylene glycol | 10.00 | — | 10.00 | — | — |
| Transcutol P | — | 15.00 | — | 15.00 | 18.00 |
| Benzyl alcohol | 2.00 | 2.00 | — | — | — |
| Phenoxyethanol | — | — | 1.00 | 1.00 | 1.00 |

TABLE 4-continued

Compositions (% w/w) of the solvent systems useful for cream, lotion and foam formulations.

| | Cream, lotion, and foam solvent systems | | | | |
|---|---|---|---|---|---|
| Excipient | SSCR06 | SSCR07 | SSCR28 | SSCR29 | SSCR30 |
| Disodium EDTA | 0.05 | 0.05 | 0.05 | 0.05 | 0.05 |
| Polysorbate 80 | — | — | 3.00 | 3.00 | — |
| Phosphoric acid solution | To pH 5.5 | To pH 5.5 | To pH 5.5 | To pH 5.5 | To pH 5.5 |
| Trolamine | | | | | |
| 2nd addition of water | Q.S. | Q.S. | Q.S. | Q.S. | Q.S. |
| Total | 71.59 | 71.59 | 80.00 | 80.00 | 80.00 |
| Saturated solubility (% w/w) (MP20200248) | 1.92 | ≥3.79 | 1.60 | 1.72 | 1.72 |

Example 4: Development of Cream Formulations

Utilizing trolamine to adjust pH, a selection of cream formulations were prepared for ruxolitinib phosphate. The formulations selected for short term stability testing with the compositions are presented in Tables 5 and 6, and characterization of these formulations presented in Table 7.

All formulations had similarly low instability indexes (0.024 for CR03 and 0.011 for CR07) and were described as high viscosity creams with smooth application. Due to their apparent pH (ca. 5.5), these formulations should have a reduced risk for causing potential irritation.

The cream formulations were prepared based on the following generic manufacturing methods for the preparation of cream and lotion formulations:

(i) The aqueous phases of the formulations were prepared in amber Durans and stirred by magnetic stirrer bar at 400 RPM until visually homogenous.

(ii) For formulations containing EDTA and/or propyl gallate, these were initially dissolved in a portion of the water and stirred at 400 RPM, then added to the vessel from Step (i).

(iii) Ruxolitinib phosphate was added to the aqueous phases and stirred at 400 RPM for ca. 5 mins, before pH adjustment. The apparent pH of the phases was monitored until the API was observed to visually dissolve.

(iv) The oil phases of the formulations were prepared in separate amber Durans.

(v) For formulations containing a gelling agent, these were dispersed in an appropriate liquid oil and stirred at 500 RPM until visually homogenous, then will be added to the vessel from Step (iv).

(vi) The oil phases were placed into a water bath at 70° C. until melted (ca. 1 hr), or 90° C. for solid oil phases containing Kolliphor HCO. Additionally, the aqueous phases, liquid oil phases and homogeniser head were heated.

(vii) The three phases (aqueous, liquid oil and molten solid oil phase) were combined, and homogenised using an IKA T25 Ultra Turrax for 2 mins at 10,000 RPM.

(viii) Following homogenisation, the formulations were allowed to cool to room temperature whilst stirring using an IKA stirrer at 200 RPM.

(ix) Once the formulation had reached room temperature, phenoxyethanol was added and the formulation hand stirred until incorporated.

(x) The apparent pH of the formulation was checked, and any final pH adjustment, or Q.S. with water completed.

TABLE 5

Compositions (% w/w) of the cream formulations.

| | Cream formulations | | | | |
|---|---|---|---|---|---|
| Excipients | CR01 PBO SSCR06 | CR03 ACT SSCR06 | CR06 ACT SSCR29 | CR07 ACT SSCR06 | CR08 ACT (LO14) SSCR06 |
| Ruxolitinib phosphate | — | 1.450 | 1.452 | 1.450 | 1.450 |
| (free base) | | (1.10) | (1.10) | (1.10) | (1.10) |
| Water | 23.55 | 22.10 | 42.00 | 29.00 | 29.00 |
| PEG 400 | 8.00 | 8.00 | — | 8.00 | 8.00 |
| Glycerol | 20.00 | 20.00 | 15.00 | 20.00 | 20.00 |
| Propylene glycol | 10.00 | 10.00 | — | 10.00 | 10.00 |
| Transcutol P | — | — | 15.00 | — | — |
| Benzyl alcohol | 2.00 | 2.00 | — | — | — |
| Disodium EDTA | 0.05 | 0.05 | 0.05 | 0.05 | 0.05 |
| Polysorbate 80 | — | — | 3.00 | — | — |
| Glyceryl monostearate (Kolliwax GMS II) | 3.00 | 1.91 | — | — | 0.36 |
| Brij S2 | — | — | 1.37 | 3.61 | — |
| Brij S721 | — | — | — | 1.39 | — |
| Cetomacrogol 1000 | — | 3.09 | 3.63 | — | 4.64 |
| Polawax NF | — | 6.00 | — | 6.50 | 8.00 |
| Cetyl alcohol | 3.00 | — | 3.00 | — | — |
| Stearyl alcohol | 1.75 | — | 2.00 | — | — |
| Cetostearyl alcohol | — | 2.00 | — | — | — |

TABLE 5-continued

Compositions (% w/w) of the cream formulations.

|  | Cream formulations | | | | |
|---|---|---|---|---|---|
| Excipients | CR01 PBO SSCR06 | CR03 ACT SSCR06 | CR06 ACT SSCR29 | CR07 ACT SSCR06 | CR08 ACT (LO14) SSCR06 |
| Light Mineral Oil | 4.00 | 5.00 | 3.00 | 5.00 | — |
| White Soft Paraffin | 7.00 | — | — | — | — |
| Castor oil | — | — | — | 3.00 | — |
| Hydrogenated castor oil (Kolliphor HCO) | — | — | — | — | — |
| Isopropyl myristate | — | — | — | — | 3.41 |
| GTCC | 5.00 | 7.40 | 7.00 | 8.91 | 10.00 |
| ST-Cyclomethicone 5-NF | — | 1.00 | — | — | — |
| Kolliphor OD | — | — | — | — | 2.00 |
| Dimethicone 350 | 1.00 | — | — | — | — |
| Polysorbate 20 | 1.25 | — | — | — | — |
| Xanthan gum | 0.40 | — | — | — | — |
| Phosphoric acid solution Trolamine | To pH 5.5 | To pH 5.5 | To pH 5.5 | To pH 5.5 | To pH 5.5 |
| 2nd addition of water | Q.S. | Q.S. | Q.S. | Q.S. | Q.S. |
| Phenoxyethanol | — | — | 1.00 | 1.00 | 1.00 |
| Total | 100.00 | 100.00 | 100.00 | 100.00 | 100.00 |

TABLE 6

Compositions (% w/w) of the cream formulations.

|  | Cream formulations | | | |
|---|---|---|---|---|
| Excipients | CR10 ACT SSCR28 | CR11 ACT (LO15) SSCR29 | CR13 ACT SSCR29 | CR14 ACT SSCR30 |
| Ruxolitinib phosphate (free base) | 1.355 (1.03) | 1.452 (1.10) | 1.452 (1.10) | 1.452 (1.10) |
| Water | 30.00 | 42.00 | 37.00 | 37.00 |
| PEG 400 | 12.00 | — | — | — |
| Glycerol | 20.00 | 15.00 | 20.00 | 20.00 |
| Propylene glycol | 10.00 | — | — | — |
| Transcutol P | — | 15.00 | 18.00 | 18.00 |
| Benzyl alcohol | — | — | — | — |
| Disodium EDTA | 0.05 | 0.05 | 0.05 | 0.05 |
| Polysorbate 80 | 3.00 | 3.00 | — | — |
| Glyceryl monostearate (Kolliwax GMS II) | — | — | — | 1.49 |
| Brij S2 | — | 2.18 | 2.00 | — |
| Brij S721 | — | 2.82 | 3.00 | — |
| Cetomacrogol 1000 | 1.80 | — | — | 3.51 |
| Polawax NF | — | — | 6.50 | |
| Cetyl alcohol | — | 5.00 | — | 3.00 |
| Stearyl alcohol | — | — | — | 2.00 |
| Cetostearyl alcohol | 8.00 | — | — | — |
| Light Mineral Oil | 4.00 | 3.50 | 2.50 | 8.00 |

TABLE 6-continued

Compositions (% w/w) of the cream formulations.

|  | Cream formulations | | | |
|---|---|---|---|---|
| Excipients | CR10 ACT SSCR28 | CR11 ACT (LO15) SSCR29 | CR13 ACT SSCR29 | CR14 ACT SSCR30 |
| White Soft Paraffin | 2.00 | 1.50 | — | — |
| Castor oil | — | — | — | — |
| Hydrogenated castor oil (Kolliphor HCO) | — | — | — | 2.00 |
| Isopropyl myristate | — | — | — | — |
| GTCC | 4.20 | 5.00 | 6.00 | — |
| ST-Cyclomethicone 5-NE | — | — | — | — |
| Kolliphor OD | — | — | — | — |
| Dimethicone 350 | — | — | — | — |
| Polysorbate 20 | — | — | — | — |
| Xanthan gum | — | — | — | — |
| Phosphoric acid solution Trolamine | To pH 5.5 | To pH 5.5 | To pH 5.5 | To pH 5.5 |
| 2nd addition of water | Q.S. | Q.S. | Q.S. | Q.S. |
| Phenoxyethanol | 1.00 | 1.00 | 1.00 | 1.00 |
| Total | 100.00 | 100.00 | 100.00 | 100.00 |

TABLE 7

Characterization of the cream formulations.

| Formulation | Macroscopic appearance | Microscopic appearance | Apparent pH | Instability index |
|---|---|---|---|---|
| CR01 PBO | Faint grey, opaque, smooth application, high viscosity | Excipient particulates observed | 5.15 | 0.035 |
| CR03 ACT | Faint grey, opaque, smooth application, high viscosity | Excipient particulates observed | — | 0.024 |
| CR06 ACT | White, opaque, smooth application, high viscosity. Lotion like consistency. | No API or excipient particulates observed | 5.38 | 0.318 |

TABLE 7-continued

| | | | Apparent | Instability |
|---|---|---|---|---|
| Formulation | Macroscopic appearance | Microscopic appearance | pH | index |
| CR07 ACT | White, opaque, smooth application, high viscosity. | No API or excipient particulates observed | 5.81 | 0.011 |
| CR08 ACT (LO14) | White, opaque, smooth application, medium viscosity. Lotion like consistency. | No API or excipient particulates observed | 5.45 | 0.532 |
| CR10 ACT | White, opaque, smooth application, high viscosity. Lotion like consistency. | No API or excipient particulates observed | 5.45 | 0.334 |
| CRI1 ACT (LO15) | White, opaque, smooth application, high viscosity. Lotion like consistency. | No API or excipient particulates observed | 5.56 | 0.235 |
| CR13 ACT | White, opaque, smooth application, high viscosity. | No API or excipient particulates observed | 5.76 | 0.005 |
| CR14 ACT | White, opaque, smooth, high viscosity. | No API or excipient particulates observed | 5.51 | 0.071 |

Characterization of the cream formulations.

Example 5: Development of Lotion Formulations

A selection of lotion formulations for ruxolitinib phosphate were prepared and are presented in Table 8, and characterization of these formulations are presented in Table 9: These incorporate various oil phases which provide differing organoleptic properties.

The lotion formulations were prepared based on the following generic manufacturing methods for the preparation of cream and lotion formulations:

(i) The aqueous phases of the formulations were prepared in amber Durans and stirred by magnetic stirrer bar at 400 RPM until visually homogenous.

(ii) For formulations containing EDTA and/or propyl gallate, these were initially dissolved in a portion of the water and stirred at 400 RPM, then added to the vessel from Step (i).

(iii) Ruxolitinib phosphate was added to the aqueous phases and stirred at 400 RPM for ca. 5 mins, before pH adjustment. The apparent pH of the phases was monitored until the API was observed to visually dissolve.

(iv) The oil phases of the formulations were prepared in separate amber Durans.

(v) For formulations containing a gelling agent, these were dispersed in an appropriate liquid oil and stirred at 500 RPM until visually homogenous, then will be added to the vessel from Step (iv).

(vi) The oil phases were placed into a water bath at 70° C. until melted (ca. 1 hr), or 90° C. for solid oil phases containing Kolliphor HCO. Additionally, the aqueous phases, liquid oil phases and homogenizer head were heated.

(vii) The three phases (aqueous, liquid oil and molten solid oil phase) were combined, and homogenized using an IKA T25 Ultra Turrax for 2 mins at 10,000 RPM.

(viii) Following homogenization, the formulations were allowed to cool to room temperature whilst stirring using an IKA stirrer at 200 RPM.

(ix) Once the formulation had reached room temperature, phenoxyethanol was added and the formulation hand stirred until incorporated.

(x) The apparent pH of the formulation was checked, and any final pH adjustment, or Q.S. with water completed.

TABLE 8

Compositions (% w/w) of the lotion formulations.

| | Lotion formulations | | | | |
|---|---|---|---|---|---|
| Excipients | LO07 ACT SSCR28 | LO08 ACT (CR15) SSCR06 | LO10 ACT SSCR28 | LO11 ACT SSCR28 | LO13 ACT (CR16) SSCR29 |
| Ruxolitinib phosphate | 1.36 | 1.45 | 1.36 | 1.21 | 1.45 |
| (free base) | (1.03) | (1.10) | (1.03) | (0.92) | (1.10) |
| Water | 30.00 | 26.00 | 27.00 | 30.00 | 42.00 |
| PEG 400 | 12.00 | 8.00 | 12.00 | 12.00 | — |
| Glycerol | 20.00 | 20.00 | 20.00 | 20.00 | 15.00 |
| Propylene glycol | 10.00 | 10.00 | 10.00 | 10.00 | — |
| Transcutol P | — | — | — | — | 15.00 |
| Disodium EDTA | 0.05 | 0.05 | 0.05 | 0.05 | 0.05 |
| Polysorbate 80 (Tween 80) | 3.00 | — | 3.00 | 3.00 | 3.00 |

TABLE 8-continued

Compositions (% w/w) of the lotion formulations.

| | Lotion formulations | | | | |
|---|---|---|---|---|---|
| Excipients | LO07 ACT SSCR28 | LO08 ACT (CR15) SSCR06 | LO10 ACT SSCR28 | LO11 ACT SSCR28 | LO13 ACT (CR16) SSCR29 |
| Brij S2 | 2.18 | — | 2.00 | — | — |
| Brij S721 | 2.82 | — | 3.00 | — | — |
| Glyceryl monostearate (GMS II) | — | — | — | — | 3.00 |
| Cetomacrogol 1000 | — | 1.80 | — | 1.80 | — |
| Cetostearyl alcohol | — | 7.61 | 3.00 | 5.00 | — |
| Cetyl alcohol | 3.00 | — | — | — | 3.00 |
| Stearyl alcohol | — | — | — | — | 1.75 |
| Light Mineral Oil | 3.50 | 8.00 | 4.50 | 4.00 | 2.70 |
| White Soft Paraffin | 1.50 | 2.00 | — | 2.00 | 5.50 |
| Isopropyl myristate | — | — | 6.00 | — | — |
| GTCC | 7.00 | 9.00 | — | 7.20 | 3.65 |
| ST-Cyclomethicone 5-NF | — | — | 1.50 | — | — |
| Xanthan gum | — | — | 0.20 | — | 0.40 |
| Phosphoric acid solution Trolamine | To pH 5.5 | To pH 5.5 | To pH 5.5 | To pH 5.5 | To pH 5.5 |
| 2nd addition of water | Q.S. | Q.S. | Q.S. | Q.S. | Q.S. |
| Phenoxyethanol | 1.00 | 1.00 | 1.00 | 1.00 | 1.00 |
| Total | 100.00 | 100.00 | 100.00 | 100.00 | 100.00 |

TABLE 9

Characterization of the lotion formulations.

| Formulation | Macroscopic appearance | Microscopic appearance | Apparent pH | Instability index |
|---|---|---|---|---|
| LO07 ACT | White, opaque, smooth application, high viscosity. | No drug or excipient particulates observed | 5.41 | 0.194 |
| LO08 ACT | White, opaque, smooth application, high viscosity | No drug or excipient particulates observed | 4.75 | 0.102 |
| LO1 ACT | White, opaque, smooth application, high viscosity | No drug or excipient particulates observed | 5.21 | 0.108 |
| LO11 ACT | White, opaque, smooth application, high viscosity | No drug or excipient particulates observed | 5.51 | 0.334 |
| LO13 ACT | White, opaque, smooth application, high viscosity | No drug or excipient particulates observed | 5.57 | 0.333 |

Example 6: Development of Foam Formulations

Foam formulations (i.e., foamable formulations) for ruxolitinib phosphate were also investigated utilizing trolamine to increase the pH. The foam formulations were manufactured similarly to cream and lotion formulations, with propellants subsequently added using a Pamasol Aerosol Filler. The compositions are presented in Table 10, and characterization of these formulations are presented in Table 11.

The following generic manufacturing method was used for the preparation of foam formulations:

(i) The foam premixes were manufactured as per the methods used for the manufacture of creams and lotions.

(ii) Foam premixes was added to canisters and valves will be crimped on.

(iii) Propellant was added to the canisters from Step (ii) using the Pamasol.

(iv) The completed foams were left to mix on a roller mixer overnight.

TABLE 10

Compositions (% w/w) of the foam formulations.

| | Foam formulations | | | | | |
|---|---|---|---|---|---|---|
| Excipients | Foam 09 LO07 | Foam 17 SSCR30 | Foam 18 SSCR28 | Foam 19 SSCR28 | Foam 20 SSCR29 | Foam 21 SSCR29 |
| Ruxolitinib phosphate (free base) | 1.22 (0.92) | 1.16 (0.88) | 1.22 (0.92) | 1.16 (0.88) | 1.16 (0.88) | 1.16 (0.88) |
| Water | 27.00 | 29.60 | 27.00 | 24.00 | 33.60 | 33.60 |
| PEG 400 | 10.80 | — | 10.80 | 9.60 | — | — |
| Glycerol | 18.00 | 16.00 | 18.00 | 16.00 | 12.00 | 12.00 |
| Propylene glycol | 9.00 | — | 9.00 | 8.00 | | |
| Transcutol P | — | 14.40 | — | — | 12.00 | 12.00 |
| Di sodium EDTA | 0.045 | 0.0400 | 0.045 | 0.040 | 0.040 | 0.040 |
| Polysorbate 80 (Tween 80) | 2.70 | — | 2.70 | 2.40 | 2.40 | 2.40 |
| Brij S2 | 1.96 | — | 1.67 | 3.20 | — | — |
| Brij S721 | 2.54 | — | — | — | — | — |
| Kolliphor CSA 50 | — | 4.00 | — | — | 4.00 | 4.00 |
| Kolliphor CS20 | — | 4.80 | — | 4.00 | 4.80 | 4.80 |
| Kollicream 3C | — | 2.00 | — | — | 2.00 | 2.00 |
| PEG 4000 | — | — | 14.18 | 5.21 | — | — |
| Cetyl alcohol | 2.70 | — | — | — | — | — |
| Stearyl alcohol | — | — | 1.80 | — | — | — |
| Light Mineral Oil | 3.15 | 5.20 | — | 3.20 | 5.20 | 5.20 |
| White Soft Paraffin | 1.35 | — | — | — | — | — |
| GTCC | 6.30 | — | — | — | — | — |
| Xanthan gum | — | — | 0.36 | 0.32 | — | — |
| Phosphoric acid solution | To pH | to pH 5.5 | to pH 5.5 | to pH 5.5 | to pH 5.5 | to pH 5.5 |
| Trolamine | 5.5 | | | | | |
| 2nd addition of water | to 90% | to 80% | to 80% | to 80% | to 80% | to 80% |
| Phenoxyethanol | 0.90 | 0.80 | 0.80 | 0.80 | 0.80 | 0.80 |
| Sub-total | 90.00 | 80.00 | 90.00 | 80.00 | 80.00 | 80.00 |
| HFA-134 | — | 20.00 | 10.00 | 20.00 | 20.00 | — |
| DME | 10.00 | — | — | — | — | — |
| HFO-1234ze | — | — | — | — | — | 20.00 |
| Total | 100.00 | 100.00 | 100.00 | 100.00 | 100.00 | 100.00 |

TABLE 11

Characterization of the foam formulations
selected for short term stability testing.

| Formu-lation | Appearance in the canister | Phase separation in the canister | Ease of actua-tion | Appear-ance of foam | Collapse time |
|---|---|---|---|---|---|
| Foam 09 | Faint grey, opaque, low viscosity | N | Easy | White, small bubbles | >24 h |
| Foam 17 | White, opaque, low viscosity | | | | |
| Foam 18 | Faint grey, opaque, low viscosity | | | | |
| Foam 19 | Faint grey, opaque, low viscosity | | | | |
| Foam 20 | Faint grey, opaque, low viscosity | | | | |

Example 7: Development of Spray (for Pump Spray) Formulations

A selection of pump spray formulations for ruxolitinib phosphate were investigated. Pump spray formulations are simple solutions, typically with a high level of volatile excipients (such as ethanol), that will evaporate upon application to the skin. There is no propellant included, so the formulation is actuated by a manual pump, rather than opening a valve as with propellant sprays. The compositions are presented in Table 12.

The following generic manufacturing method will be used for the preparation of pump sprays:

(i) BHT were added to ethanol and stirred by magnetic stirrer bar for ca. 15 mins at 500 RPM, until visually dissolved.

(ii) Poloxamer or gantrez were added to the vessel from Step (i) and will be stirred for ca. 30 mins at 500 RPM, until visually dissolved.

(iii) The remaining excipients were added to the vessel from Step (iii) and the solution stirred for ca. 10 mins at 500 RPM, until visually homogenous.

(iv) Ruxolitinib phosphate was added to the vessel from Step (iii) and stirred for ca. 1 hr at 500 RPM, until visually dissolved, and the solution pH adjusted.

TABLE 12

| | Pump spray formulations | | | | |
|---|---|---|---|---|---|
| Excipient | Sol10 | Sol12 | Sol13 | Sol17 | Sol26 |
| Water | 19.00 | 10.00 | 18.00 | 15.00 | 48.00 |
| PEG 400 | — | — | 4.00 | — | — |
| Glycerol | 9.00 | 9.00 | 9.00 | 5.00 | — |
| Propylene glycol | — | — | 10.00 | — | — |
| Transcutol P | 13.00 | 13.00 | — | 11.00 | — |
| Phenoxyethanol | 1.00 | 1.00 | 1.00 | 1.00 | — |
| Disodium EDTA | — | — | — | — | — |
| BHT | — | 0.10 | 0.10 | 0.10 | — |
| Ethanol | 50.00 | 50.00 | 50.00 | 55.00 | 50.00 |
| Eudragit E 100 | — | — | — | — | — |
| Poloxamer 407 | 1.00 | — | 1.00 | — | — |
| Gantrez ES-435 | — | 10.00 | — | 10.00 | — |
| Phosphoric acid solution | pH 5.5 | pH 5.5 | pH 5.5 | pH 5.5 | pH 5.5 |
| Trolamine | | | | | |
| 2nd addition of water | Q.S. | Q.S. | Q.S. | Q.S. | Q.S. |
| Total | 100.00 | 100.00 | 100.00 | 100.00 | 100.00 |
| Saturated solubility (% w/w) | ≥3.79 | 4.78 | ≥3.79 | >3.79 | ≥3.79 |

Compositions (% w/w) of the pump spray formulations and the saturated solubility (% w/w) of ruxolitinib phosphate (presented as the freebase) in the systems.

Example 8: Synergism of Glycerol-Transcutol P

The impact of Transcutol P on the solubility of ruxolitinib phosphate in the solvent systems was observed to be far greater than expected based on its solubility in the excipient alone (11.3 mg/mL). SSCR23 was initially developed as a system with 20% w/w glycerol, and 15% Transcutol P and ruxolitinib phosphate was soluble at ca. 1% w/w in this system. When the level of Transcutol P was increased by 3% w/w (to 18% w/w in SSCR30), this resulted in an increase in solubility up to ca. 1.7% w/w, and when the Transcutol P was increased a further 2% w/w (to 20% w/w in SSCR26) the drug solubility increased substantially more than expected to 3.62% w/w, as provided in Table 13. It is suspected that this was caused by a synergistic solvent effect between glycerol and Transcutol P.

TABLE 13

| | Solvent systems demonstrating the synergism between glycerol and Transcutol P | | |
|---|---|---|---|
| Excipient | SSCR23 | SSCR30 | SSCR26 |
| Water | 31.00 | 33.00 | 31.00 |
| (total water following QS.) | (39.10) | (39.32) | (36.17) |
| Glycerol | 20.00 | 20.00 | 20.00 |
| Transcutol P | 15.00 | 18.00 | 20.00 |
| Phenoxyethanol | 1.00 | 1.00 | 1.00 |
| Di sodium EDTA | 0.05 | 0.05 | 0.05 |
| Phosphoric acid solution | to pH 5.5 | To pH 5.5 | To pH 5.5 |
| Trolamine | | | |
| 2nd addition of water | Q.S. | Q.S. | Q.S. |
| Total | 76.59 | 80.00 | 80.00 |
| Saturated solubility of Ruxolitinib phosphate | 1.095 | 1.72 | 3.62 |

Compositions (% w/w) of the solvent systems demonstrating the synergism between glycerol and Transcutol P, and the saturated solubility (% w/w) of ruxolitinib phosphate in the systems.

Example 9: Synergism Ethanol-Water Formulations

As provided in Table 14, unexpectedly high solubility of ruxolitinib phosphate (≥3.79% w/w) was observed in the pump spray formulations, considering the high level of ethanol (>50% w/w) in the systems and comparatively lower solubility of ruxolitinib phosphate in this excipient alone (ca. 0.76% w/w). The solubility of the API in this system was >3.79% w/w, indicating that there may be a synergistic solvent effect between water and ethanol causing the high solubility of ruxolitinib phosphate.

TABLE 14

| | Pump spray formulations demonstrating thepotential synergy between ethanol and water | | |
|---|---|---|---|
| Excipient | Sol 19 | Sol 25 | So l26 |
| Water | 19.00 | 19.00 | 48.00 |
| Glycerol | 3.00 | 3.00 | — |
| Transcutol P | 3.00 | 3.00 | — |
| Phenoxyethanol | 1.00 | 1.00 | — |
| BHT | 0.10 | 0.10 | — |
| Ethanol | 70.00 | 70.00 | 50.00 |
| Poloxamer 407 | 1.00 | 1.00 | — |
| Phosphoric acid solution | pH 5.5 | pH 5.5 (NaOH) | — |
| Trolamine (or NaOH) | | | |
| 2nd addition of water | Q.S. | Q.S. | — |
| Total | 100.00 | 100.00 | 100.00 |
| Saturated solubility (% w/w) | 23.79 | 23.79 | 23.79 |

Compositions (% w/w) of the pump spray formulations demonstrating the synergism between ethanol and water, and the saturated solubility (% w/w) of ruxolitinib phosphate in the systems.

Example 10: Short Term Stability Testing

The formulations selected for short-term stability testing have been detailed in Tables 15-20. These formulations were manufactured on a 250 g scale, and the following characterization was performed at each timepoint:

Ruxolitinib phosphate assay and purity

Macroscopic appearance

Microscopic appearance and droplet sizing, where appropriate

Apparent pH

Texture analysis, only at t=0, 1 month and 3 months at 25° C.

Rheology, only at t=0, 1 month and 3 months at 25° C.
Accelerated physical stability, only at t=0

Given the nature of the formulations for topical administration, the apparent pH of the formulations for short term stability are presented in Table 20. The other characterization data (e.g., ruxolitinib phosphate assay and purity, macroscopic appearance, microscopic appearance and droplet sizing, where appropriate, texture analysis, rheology, and accelerated physical stability) is not presented herein.

TABLE 15

| | | | | Compositions (% w/w) of the cream formulations selected for short-term stability testing. | | | | | |
|---|---|---|---|---|---|---|---|---|---|
| Excipients | CR01a ACT | CR03a ACT | CR06 ACT | CR07 ACT | CR10 ACT | CRB ACT | CRM ACT | CR15 ACT | CR16 ACT |
| Ruxolitinib phosphate (free base) | 0.531 (0.402) | 0.531 (0.402) | 1.195 (0.905) | 0.531 (0.402) | 1.204 (0.912) | 1.321 (1.000) | 1.321 (1.000) | 0.531 (0.402) | 1.195 (0.905) |
| Water | 29.51 | 29.51 | 42.25 | 29.51 | 30.25 | 37.13 | 37.13 | 29.51 | 42.25 |
| PEG 400 | 8.00 | 8.00 | — | 8.00 | 12.00 | — | — | 8.00 | — |
| Glycerol | 20.00 | 20.00 | 15.00 | 20.00 | 20.00 | 20.00 | 20.00 | 20.00 | 15.00 |
| Propylene glycol | 10.00 | 10.00 | — | 10.00 | 10.00 | — | — | 10.00 | — |
| Transcutol P | — | — | 15.00 | — | — | 18.00 | 18.00 | — | 15.00 |
| Di sodium EDTA | 0.05 | 0.05 | 0.05 | 0.05 | 0.05 | 0.05 | 0.05 | 0.05 | 0.05 |
| Polysorbate 80 | — | — | 3.00 | — | 3.00 | — | — | — | 3.00 |
| Kolliwax GMS II | 3.50 | 1.80 | — | — | — | — | 1.49 | — | 3.00 |
| Brij S2 | — | — | 1.37 | 3.61 | — | 2.00 | — | — | — |
| Brij S721 | — | — | — | 1.39 | — | 3.00 | — | — | — |
| Cetomacrogol 1000 | — | 3.20 | 3.63 | — | 1.80 | — | 3.51 | 1.80 | — |
| Polawax NF | — | 6.00 | — | 6.50 | — | 6.50 | — | — | — |
| Cetyl alcohol | 3.50 | — | 3.00 | — | — | — | 3.00 | — | 3.00 |
| Stearyl alcohol | 1.76 | — | 2.00 | — | — | — | 2.00 | — | 1.75 |
| Cetostearyl alcohol | — | 3.00 | — | — | 8.00 | — | — | 7.61 | — |
| Light Mineral Oil | 4.50 | 5.50 | 3.00 | 5.00 | 4.00 | 2.50 | 8.00 | 8.00 | 2.70 |
| White Soft Paraffin | 7.00 | — | — | — | 2.00 | — | — | 2.00 | 5.50 |
| Castor Oil | — | — | — | 3.00 | — | — | — | — | — |
| Kolliphor HCO | — | — | — | — | — | — | 2.00 | — | — |
| GTCC | 5.50 | 7.91 | 7.00 | 8.91 | 4.20 | 6.00 | — | 9.00 | 3.65 |
| ST-Cyclomethicone 5-NF | — | 1.00 | — | — | — | — | — | — | — |
| Xanthan gum | 0.40 | — | — | — | — | — | — | — | 0.40 |
| Phosphoric acid solution | To pH | To pH | To pH | To pH | To pH | To pH | To pH | To pH | To pH |
| Trolamine | 5.5 | 5.5 | 5.5 | 5.5 | 5.5 | 5.5 | 5.5 | 5.5 | 5.5 |
| 2nd addition of water | Q.S. | Q.S. | Q.S. | Q.S. | Q.S. | Q.S. | Q.S. | Q.S. | Q.S. |
| Phenoxy ethanol | 1.00 | 1.00 | 1.00 | 1.00 | 1.00 | 1.00 | 1.00 | 1.00 | 1.00 |
| Total | 100.00 | 100.00 | 100.00 | 100.00 | 100.00 | 100.00 | 100.00 | 100.00 | 100.00 |

TABLE 16

Compositions (% w/w) of the lotion
formulations selected for short-term stability testing.

| Excipients | LO07 ACT | LO10 ACT | LO11 ACT | LO14 ACT | LO15 ACT |
|---|---|---|---|---|---|
| Ruxolitinib Phosphate (free base) | 1.204 (0.912) | 1.204 (0.912) | 1.204 (0.912) | 0.531 (0.402) | 1.195 (0.905) |
| Water | 30.25 | 30.05 | 30.25 | 29.51 | 42.25 |
| PEG 400 | 12.00 | 12.00 | 12.00 | 8.00 | — |
| Glycerol | 20.00 | 20.00 | 20.00 | 20.00 | 15.00 |
| Propylene glycol | 10.00 | 10.00 | 10.00 | 10.00 | — |
| Transcutol P | — | — | — | — | 15.00 |
| Disodium EDTA | 0.05 | 0.05 | 0.05 | 0.05 | 0.05 |
| Polysorbate 80 | 3.00 | 3.00 | 3.00 | — | 3.00 |
| Brij S2 | 2.18 | 2.00 | — | — | 2.18 |
| Brij S721 | 2.82 | 3.00 | — | — | 2.82 |
| Kolliwax GMS II | — | — | — | 0.36 | — |
| Cetomacrogol 1000 | — | — | 1.80 | 4.64 | — |
| Cetostearyl alcohol | — | 3.00 | 5.00 | — | — |
| Cetyl alcohol | 3.00 | — | — | — | 5.00 |
| Polawax NF | — | — | — | 8.00 | — |
| Mineral oil | — | — | — | — | 3.50 |
| Light Mineral Oil | 3.50 | 4.50 | 4.00 | — | — |
| White Soft Paraffin | 1.50 | — | 2.00 | — | 1.50 |
| Isopropyl myristate | — | 6.00 | — | 3.41 | — |
| GTCC | 7.00 | — | 7.20 | 10.00 | 5.00 |
| Kolliphor OD | — | — | — | 2.00 | — |
| ST-Cyclomethicone 5-NF | — | 1.50 | — | — | — |
| Xanthan gum | — | 0.20 | — | — | — |
| Phosphoric acid solution Trolamine | To pH 5.5 | To pH 5.5 | To pH 5.5 | To pH 5.5 | To pH 5.5 |
| 2nd addition of water | Q.S. | Q.S. | Q.S. | Q.S. | Q.S. |
| Phenoxyethanol | 1.00 | 1.00 | 1.00 | 1.00 | 1.00 |
| Total | 100.00 | 100.00 | 100.00 | 100.00 | 100.00 |

TABLE 17

Compositions (% w/w) of the foam formulations
selected for short-term stability testing.

| Excipients | Foam 09 | Foam 17 | Foam 18 | Foam 19 | Foam 20 | Foam 21 |
|---|---|---|---|---|---|---|
| Ruxolitinib phosphate (free base) | 1.08 (0.82) | 1.06 (0.80) | 1.08 (0.82) | 0.96 (0.73) | 0.96 (0.73) | 0.96 (0.73) |
| Water | 27.22 | 29.70 | 27.22 | 24.20 | 33.80 | 33.80 |
| PEG 400 | 10.80 | — | 10.80 | 9.60 | — | — |
| Glycerol | 18.00 | 16.00 | 18.00 | 16.00 | 12.00 | 12.00 |
| Propylene glycol | 9.00 | — | 9.00 | 8.00 | — | — |
| Transcutol P | — | 14.40 | — | — | 12.00 | 12.00 |
| Di sodium EDTA | 0.045 | 0.0400 | 0.045 | 0.040 | 0.040 | 0.040 |
| Polysorbate 80 | 2.70 | — | 2.70 | 2.40 | 2.40 | 2.40 |
| Brij S2 | 1.96 | — | 1.67 | 3.20 | — | — |
| Brij S721 | 2.54 | — | — | — | — | — |
| Kolliphor CSA 50 | — | 4.00 | — | — | 4.00 | 4.00 |
| Kolliphor CS20 | — | 4.80 | — | 4.00 | 4.80 | 4.80 |
| Kollicream 3C | — | 2.00 | — | — | 2.00 | 2.00 |
| PEG 4000 | — | — | 14.18 | 5.21 | — | — |
| Cetyl alcohol | 2.70 | — | — | — | — | — |
| Stearyl alcohol | — | — | 1.80 | — | — | — |
| Light Mineral Oil | 3.15 | 5.20 | — | 3.20 | 5.20 | 5.20 |
| White Soft Paraffin | 1.35 | — | — | — | — | — |
| GTCC | 6.30 | — | — | — | — | — |
| Xanthan gum | — | — | 0.36 | 0.32 | — | — |
| Phosphoric acid solution Trolamine | To pH 5.5 | to pH 5.5 | to pH 5.5 | to pH 5.5 | to pH 5.5 | to pH 5.5 |
| 2nd addition of water | to 90% | to 80% | to 80% | to 80% | to 80% | to 80% |

TABLE 17-continued

Compositions (% w/w) of the foam formulations
selected for short-term stability testing.

| Excipients | Foam 09 | Foam 17 | Foam 18 | Foam 19 | Foam 20 | Foam 21 |
|---|---|---|---|---|---|---|
| Phenoxyethanol | 0.90 | 0.80 | 0.80 | 0.80 | 0.80 | 0.80 |
| Sub-total | 90.00 | 80.00 | 80.00 | 80.00 | 80.00 | 80.00 |
| HFA-134 | — | 20.00 | 20.00 | 20.00 | 20.00 | — |
| DME | 10.00 | — | — | — | — | — |
| HFO-1234ze | — | — | — | — | — | 20.00 |
| Total | 100.00 | 100.00 | 100.00 | 100.00 | 100.00 | 100.00 |

TABLE 18

Compositions (% w/w) of the spray formulations
selected for short-term stability testing.

| Excipient | Sol 13 | Sol 17 | Spray 09 | Spray 15 | Spray 23 | Spray 28 |
|---|---|---|---|---|---|---|
| Ruxolitinib phosphate | 1.98 | 1.98 | 0.0404 | 0.0404 | 0.1400 | 0.0404 |
| (free base) | (1.50) | (1.50) | (0.306) | (0.306) | (0.1061) | (0.306) |
| Water | 20.00 | 13.00 | — | — | — | — |
| PEG 400 | 4.00 | — | — | — | — | — |
| Glycerol | 9.00 | 5.00 | — | — | — | — |
| Propylene glycol | 10.00 | — | 1.00 | — | 1.00 | — |
| Transcutol P | — | 11.00 | | 1.00 | — | 1.00 |
| Phenoxy-ethanol | 1.00 | 1.00 | — | — | — | — |
| BHT | 0.10 | 0.10 | — | — | — | — |
| Ethanol | 50.00 | 55.00 | 27.96 | 27.96 | 17.86 | 27.96 |
| EudragitE 100 | — | — | 1.00 | 1.00 | — | 1.00 |
| Eudragit RL PO | — | — | — | — | 1.00 | — |
| Poloxamer 407 | 1.00 | — | — | — | — | — |
| Gantrez ES-435 | — | 10.00 | — | — | — | — |
| Phosphoric acid solution | pH 5.5 | pH 5.5 | — | — | — | — |
| Trolamine | | | — | — | — | — |
| 2nd addition of water | Q.S. | Q.S. | — | — | — | — |
| HFA-134a | — | — | 70.00 | 70.00 | 80.00 | |
| HFO-1234ze | — | — | — | — | — | 70.00 |
| Total | 100.00 | 100.00 | 100.00 | 100.00 | 100.00 | 100.00 |

TABLE 19

Apparent pH of the developed formulations at t=0
and at the subsequent timepoints.

| | | Apparent pH | | | | | |
|---|---|---|---|---|---|---|---|
| | | t=2 weeks | | t=4 weeks | | t=12 weeks | |
| Formulation | t=0 | 25 °C./60% RH | 40 °C./75% RH | 25 °C./60% RH | 40 °C./75% RH | 25 °C./60% RH | 40 °C./75% RH |
| Sponsor's ACT* | 2.99 | 2.89 | 3.00 | 3.01 | 2.98 | 3.01 | 2.93 |
| Sponsor's PBO* | 5.32 | 5.30 | 5.40 | 5.29 | 5.22 | 5.22 | 4.92 |
| CROla ACT | 5.54 | 5.40 | 5.53 | 5.40 | 5.38 | 5.37 | 5.22 |
| CROlaPBO | 5.54 | 5.46 | 5.57 | 5.40 | 5.30 | 5.31 | 5.18 |

TABLE 19-continued

Apparent pH of the developed formulations at t=0
and at the subsequent timepoints.

| | | Apparent pH | | | | | |
|---|---|---|---|---|---|---|---|
| | | t=2 weeks | | t=4 weeks | | t=12 weeks | |
| Formulation | t=0 | 25 °C./60% RH | 40 °C./75% RH | 25 °C./60% RH | 40 °C./75% RH | 25 °C./60% RH | 40 °C./75% RH |
| CR03a ACT | 5.40 | 5.24 | 5.26 | 5.26 | 5.27 | 5.19 | 5.24 |
| CR03aPBO | 5.59 | 5.52 | 5.54 | 5.27 | 5.23 | 5.40 | 5.28 |
| CRO6 ACT | 5.53 | 5.49 | 5.50 | 5.43 | 5.49 | 5.37 | 5.24 |
| CR06 PBO | 5.40 | 5.34 | 5.38 | 5.06 | 5.19 | 5.08 | 4.84 |
| CRO7 ACT | 5.79 | 5.46 | 5.34 | 5.41 | 5.35 | 5.11 | 5.26 |
| CR07 PBO | 5.47 | 5.23 | 5.26 | 5.30 | 5.22 | 5.23 | 5.18 |
| CRIO ACT | 5.50 | 5.36 | 5.47 | 5.49 | 5.35 | 5.32 | 5.16 |
| CR10PBO | 5.49 | 5.45 | 5.50 | 5.32 | 5.18 | 5.36 | 5.14 |
| CRB ACT | 5.43 | 5.45 | 5.50 | 5.45 | 5.30 | 5.40 | 5.19 |
| CRB PBO | 5.32 | 5.30 | 5.21 | 5.07 | 5.00 | 5.11 | 4.91 |
| CR14 ACT | 5.48 | 5.51 | 5.59 | 5.47 | 5.46 | 5.41 | 5.37 |
| CR14 PBO | 5.53 | 5.53 | 5.57 | 5.39 | 5.34 | 5.37 | 5.21 |
| CR15 ACT | 5.47 | 5.35 | 5.30 | 5.29 | 5.23 | 5.14 | 5.07 |
| CR15 PBO | 5.54 | 5.52 | 5.58 | 5.31 | 5.33 | 5.23 | 5.18 |
| CR16 ACT | 5.49 | 5.54 | 5.52 | 5.47 | 5.45 | 5.38 | 5.29 |
| CR16PBO | 5.44 | 5.45 | 5.37 | 5.29 | 5.21 | 5.24 | 4.99 |
| LO07 ACT | 5.54 | 5.46 | 5.39 | 5.52 | 5.38 | 5.35 | 5.12 |
| LO07 PBO | 5.40 | 5.59 | 5.36 | 5.41 | 5.61 | 5.29 | 5.14 |
| LOW ACT | 5.50 | 5.37 | 5.33 | 5.47 | 5.26 | 5.33 | 5.02 |
| LO10PBO | 5.68 | 5.43 | 5.43 | 5.40 | 5.52 | 5.24 | 5.12 |
| LOU ACT | 5.50 | 5.63 | 5.32 | 5.49 | 5.40 | 5.33 | 5.13 |
| LOU PBO | 5.65 | 5.62 | 5.41 | 5.37 | 5.39 | 5.30 | 5.09 |
| LOI4 ACT | 5.12 | 5.14 | 5.13 | 5.25 | 5.14 | 5.14 | 5.06 |
| LOI4 PBO | 5.62 | 5.46 | 5.37 | 5.31 | 5.39 | 5.31 | 5.26 |
| LOI5 ACT | 5.49 | 5.51 | 5.54 | 5.53 | 5.42 | 5.46 | 5.15 |
| LOI5 PBO | 5.23 | 5.31 | 5.26 | 5.03 | 5.07 | 5.14 | 4.89 |

TABLE 20

Apparent pH of the developed formulations at t=0
and at the subsequent timepoints.

| | | Apparent pH | | | | | |
|---|---|---|---|---|---|---|---|
| | | t=2 weeks | | t=4 weeks | | t=12 weeks | |
| Formulation | t=0 | 25 °C./60%RH | 40 °C./75% RH | 25 °C./60% RH | 40 °C./75%RH | 25 °C./60%RH | 40 °C./75% RH |
| Foam 09 ACT | 5.63 | 5.79 | 5.74 | 5.62 | 5.72 | 5.50 | 5.52 |
| Foam 09 PBO | 5.69 | 5.35 | 6.05 | 5.81 | 5.89 | 5.44 | 5.30 |
| Foam 17 ACT | 5.60 | 5.51 | 5.53 | 5.38 | 5.33 | 5.06 | 5.14 |
| Foam 17 PBO | 5.39 | 5.40 | 5.71 | 5.65 | 5.91 | 4.26 | 4.93 |
| Foam 18 ACT | 5.68 | 5.81 | 5.54 | 5.59 | 5.65 | 5.42 | 5.18 |
| Foam 18 PBO | 5.68 | 5.63 | 5.73 | 5.78 | 5.85 | 5.29 | 5.44 |
| Foam 19 ACT | 5.68 | 5.55 | 5.56 | 5.91 | 5.67 | 5.21 | 5.20 |
| Foam 19 PBO | 5.86 | 5.86 | 5.80 | 6.11 | 6.13 | 5.03 | 5.34 |
| Foam 20 ACT | 5.79 | 5.54 | 5.55 | 5.59 | 5.55 | 4.98 | 5.21 |
| Foam 20 PBO | 6.08 | 5.79 | 5.77 | 6.10 | 6.53 | 4.15 | 5.51 |
| Foam 21 ACT | 5.84 | 5.38 | 5.54 | 5.59 | 5.63 | 4.14 | 4.81 |
| Foam 21 PBO | 5.77 | 5.50 | 5.87 | 5.82 | 6.53 | 4.79 | 5.29 |
| Sol 13 ACT | 5.53 | 5.53 | 5.44 | 5.47 | 5.51 | 5.52 | 5.58 |
| Sol 13 PBO | 5.40 | 5.50 | 5.34 | 5.38 | 5.47 | 5.50 | 5.51 |
| Sol 17 ACT | 5.06 | 6.02 | 5.79 | 5.91 | 5.75 | 5.97 | 5.75 |
| Sol 17 PBO | 5.17 | 5.13 | 4.93 | 5.15 | 4.95 | 4.98 | 4.90 |

Example 11: Characterization of Formulations

Tables 21 and 22 show the characteristics of cream and lotion formulations based on the short-term stability testing, the in vitro permeation and penetration testing and the RHE irritancy study results.

In Tables 21 and 22, rankings were on a scale of 1-3, where 1 was the best, 2 was average, and 3 was the worst. In Table 22, rankings from performance testing are in order of their relative performance where the lowest number is the best.

TABLE 21

Characteristics of the Formulations.

| Parameter | Criteria |
|---|---|
| Ruxolitinib phosphate purity following t = 12 weeks at 40° C. | 1 Change of <0.5% area from t = 0<br>2 Change of 0.5-1.0% area from t = 0<br>3 Change of >1.0% area from t = 0 |
| Macroscopic appearance* | 1 No notable change from t = 0<br>2 Increase in viscosity from t = 0, or change in smoothness<br>3 Phase separation observed at 25° C. |

TABLE 21-continued

Characteristics of the Formulations.

| Parameter | Criteria |
|---|---|
| Presence of API particulates | 1 No API particulates observed<br>2 API particulates observed |
| Apparent pH following t = 12 weeks at 40° C. | 1 Change of ≤1 pH unit from t = 0<br>2 Change of >1 pH unit from t = 0 |
| Rheological profile over t = 12 weeks at 25° C.^ | 1 No notable change<br>2 Notable change in 1 parameter<br>3 Notable change in >1 parameter |
| Instability index (active formulation) | 1 <0.2<br>2 0.2-0.5<br>3 >0.5 |
| IVPT    Delivery to the epidermis<br>Delivery to the dermis<br>Delivery to the receptor solution | In terms of rank order from the IVPT study, where 1 delivered the most API, and 10 the least |
| RHE irritancy testing (active formulation) | 1 Non-irritant (cell viability of >60%)<br>2 Inconclusive (cell viability 40-60%)<br>3 Irritant (cell viability of <40%) |

TABLE 22

Characteristics of cream and lotion formulations.

| Parameter | | CRO1a | CRO3a | CR06 | CR07 | CR10 | CR13 | CR14 | CR15 | CR16 | LO07 | LO10 | LO11 | LO14 | LO15 |
|---|---|---|---|---|---|---|---|---|---|---|---|---|---|---|---|
| Drug loading (% w/w) | | 0.40 | 0.40 | 0.90 | 0.40 | 0.91 | 1.0 | 1.0 | 0.40 | 0.90 | 0.91 | 0.91 | 0.91 | 0.40 | 0.90 |
| Ruxolitinib phosphate purity following t=12 weeks at 40 °C | | 1 | 1 | 1 | 1 | 1 | 1 | 1 | 1 | 1 | 1 | 1 | 1 | 1 | 1 |
| Macroscopic appearance | | 2 | 1 | 3 | 1 | 1 | 1 | 2 | 1 | 2 | 1 | 1 | 1 | 1 | 1 |
| Presence of API particulates | | 1 | 1 | 1 | 1 | 1 | 1 | 1 | 1 | 1 | 1 | 1 | 1 | 1 | 1 |
| Apparent pH following t=12 weeks at 40 °C | | 1 | 1 | 1 | 1 | 1 | 1 | 1 | 1 | 1 | 1 | 1 | 1 | 1 | 1 |
| Rheological profile following t=12 weeks at 40 °C | | 3 | 1 | 2 | 1 | 1 | 2 | 2 | 1 | 1 | 1 | 1 | 1 | 1 | 1 |
| Instability index (active formulation) | | 1 | 1 | 3 | 1 | 1 | 1 | 1 | 1 | 1 | 1 | 1 | 1 | 2 | 2 |
| IV PT | Delivery to the epidermis | 9 | — | — | — | 8 | 6 | 2 | — | 1 | 5 | 4 | 7 | 10 3 | |
| | Delivery to the dermis | 10 | — | — | — | 2 | 9 | 7 | — | 4 | 5 | 8 | 6 | 3 1 | |
| | Delivery to the receptor solution | 10 | — | — | — | 9 | 8 | 5 | — | 2 | 3 | 1 | 4 | 6 7 | |
| RHE irritancy testing | | 3 | — | — | — | — | — | 3 | — | — | — | 3 | 3 | — | 3 |

Example 12: Additional Comparative Examples

In Table 23, the following comparative examples were compared with the example cream formulations in in vitro permeation and penetration (IVPT) testing (CR01a, CR10 ACT, CR13 ACT, CR15 ACT, AND CR16 ACT) and lotion formulations (LO07 ACT, LO10 ACT, LO11 ACT, LO14 ACT, and LO15 ACT). Human abdominal skin from elective surgery was used of a thickness of 400 micrometers using a receptor solution of PBS (pH 7.4) plus 0.01% Brij at a dose amount of 10 mg/cm$^2$ in a low flow cell (6 microL/min). Extraction was made for the dermis and epidermis.

Figure 2:
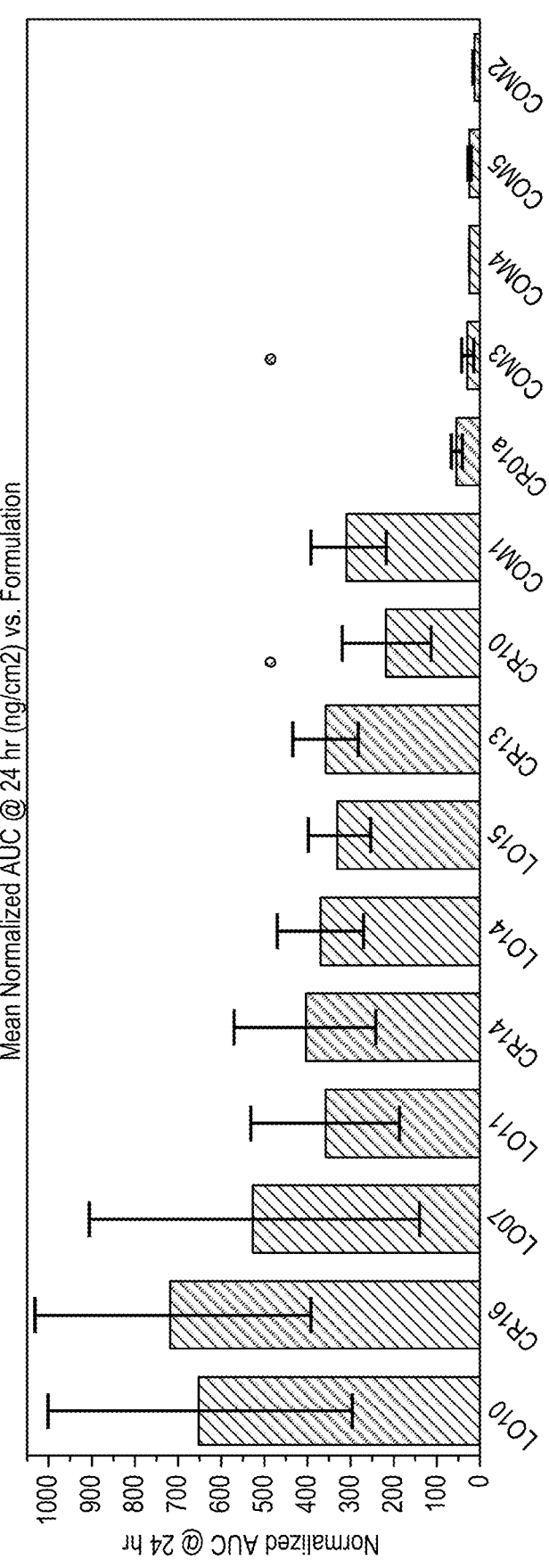
FIG. 2 illustrates the amount of ruxolitinib which permeated across the skin into the receptor solution over 24 hours.

The amount of ruxolitinib which permeated across the epidermis and dermis after 24 hours, following the application of test formulations in combined with data normalized to the average performance of bridge formulation CR01a is shown in the FIG. 1. The amount of ruxolitinib which permeated across the skin into the receptor solution over 24 hours, following the application of test formulations in combined with data normalized to the average performance of bridge formulation CR01a is shown in the FIG. 2.

Surprising, it was found that formulations being pH adjusted with trolamine were able to deliver higher amounts of ruxolitinib to the dermis (e.g., CR16) as compared to a formulation (COM1) without trolamine, even though the trolamine pH adjusted formulations were of substantially lower ruxolitinib strengths.

Example 13: Product Transformation: Apparent pH

A. Product Transformation

Product transformation of the lead formulations from formulation development was also investigated. Product transformation, or vehicle metamorphosis, describes the changes that occur to a formulation between storage in the primary packaging and dose delivery. This will typically comprise sheer of the formulation caused by dispensing and applying the product; evaporation of volatile excipients; and penetration of excipients and the API into the tissue. Each of these can impact the Q3 microstructure, efficacy, organoleptic properties, and safety profile of the formulation and therefore represents a critical quality attribute (CQA) for the development of topical products. As such, understanding product transformation of topical products is used during the early stages of development and this has been recognized by regulatory agencies.

Method development was performed under the previous studies confirming the transformation parameters and the testing methodology. PermeaPad membranes were selected as the transformation media in this study because they are biomimetic and provide the opportunity for absorption of excipients into their lipid layer, as the Stratum Corneum of the skin would, without the challenging practical considerations of using ex vivo skin (e.g., sourcing the amount of tissue required and the vaccinations required to handle it). The investigation performed under this study, using the formulations selected for short term stability testing assessed the impact of absorption of API and excipients into the skin

TABLE 23

Additional comparative examples.

| | Comparative formulations | | | | |
|---|---|---|---|---|---|
| Excipients | COM1 No trolamine or pH adjustment (1.5% w/w) | COM2 No trolamine or pH adjustment (0.09% w/w) | COM3 No trolamine, pH 4 (0.09% w/w) | COM4 No trolamine, pH 5.5 (0.09% w/w) | COM5 No trolamine, pH 7 (0.09% w/w) |
| Ruxolitinib phosphate | 1.96 | 0.119 | 0.119 | 0.119 | 0.119 |
| (free base) | (1.48) | (0.901) | (0.901) | (0.901) | (0.901) |
| Water | 48.95 | 50.78 | 39.11 | 39.11 | 39.11 |
| PEG 200 | 7.0 | 7.0 | 7.0 | 7.0 | 7.0 |
| Propylene Glycol | 15.0 | 15.0 | 15.0 | 15.0 | 15.0 |
| Methyl paraben | 0.10 | 0.10 | 0.10 | 0.10 | 0.10 |
| Propyl paraben | 0.05 | 0.05 | 0.05 | 0.05 | 0.05 |
| Phenoxyethanol | 0.50 | 0.50 | 0.50 | 0.50 | 0.50 |
| EDTA disodium | 0.50 | 0.50 | 0.50 | 0.50 | 0.50 |
| Glyceryl monostearate | 0.05 | 0.05 | 0.05 | 0.05 | 0.05 |
| Cetyl alcohol | 3.00 | 3.00 | 3.00 | 3.00 | 3.00 |
| Stearyl alcohol | 3.00 | 3.00 | 3.00 | 3.00 | 3.00 |
| Cetostearyl alcohol | 1.75 | 1.75 | 1.75 | 1.75 | 1.75 |
| Light Mineral Oil | 4.00 | 4.00 | 4.00 | 4.00 | 4.00 |
| White Soft Paraffin | 7.00 | 7.00 | 7.00 | 7.00 | 7.00 |
| Medium chain triglyceride | 5.00 | 5.00 | 5.00 | 5.00 | 5.00 |
| Dimethicone 350 | 1.00 | 1.00 | 1.00 | 1.00 | 1.00 |
| Polysorbate 20 | 1.25 | 1.25 | 1.25 | 1.25 | 1.25 |
| Xanthan gum | 0.40 | 0.40 | 0.40 | 0.40 | 0.40 |
| Phosphoric acid solution NaOH | — | — | To pH 4.0 | To pH 5.5 | To pH 7.0 |
| 2$^{nd}$ addition Water | — | — | | | |
| Total | 100.00 | 100.00 | 100.00 | 100.00 | 100.00 |

(using PermeaPad membranes as a model), and heat (32° C.) causing the evaporation of volatile excipients on the following parameters:

Adhesivity by texture analysis

Macroscopic appearance

Microscopic appearance

Apparent pH

The results from adhesivity by texture analysis, macroscopic appearance, and microscopic appearance are not provided herein.

B. Apparent pH

The apparent pH results are included herein in view of the topical administration of the formulation to the dermis. The apparent pH of the formulations following product transformation was assessed, using the t=0 from short term stability testing as the pre-transformation data for comparison. The data is presented in Table 24. The apparent pH of the spray formulations was not assessed following transformation as only a solid film remained.

Although minor variation was observed, as expected, considering the low levels of water that remain in the formulations following product transformation, and the highly viscous nature of the residual phases, there was no material change in the apparent pH of any of the formulations following product transformation.

TABLE 24

Apparent pH of the developed formulations at
t = 0 and following product transformation.

| | Apparent pH | | | |
|---|---|---|---|---|
| | Active | | Placebo | |
| Formulation | t = 0 | Post transformation | t = 0 | Post transformation |
| CR01a | 5.54 | 5.67 | 5.54 | 5.27 |
| CR03a | 5.40 | 5.49 | 5.59 | 5.22 |

TABLE 24-continued

Apparent pH of the developed formulations at
t = 0 and following product transformation.

| | Apparent pH | | | |
|---|---|---|---|---|
| | Active | | Placebo | |
| Formulation | t = 0 | Post transformation | t = 0 | Post transformation |
| CR06 | 5.53 | 5.82 | 5.40 | 5.74 |
| CR07 | 5.79 | 5.74 | 5.47 | 4.03 |
| CR10 | 5.50 | 5.84 | 5.49 | 6.36 |
| CR13 | 5.43 | 5.42 | 5.32 | 5.78 |
| CR14 | 5.48 | 5.64 | 5.53 | 6.03 |
| CR15 | 5.47 | 5.49 | 5.54 | 6.23 |
| CR16 | 5.49 | 5.24 | 5.44 | 5.65 |
| LO07 | 5.54 | 5.89 | 5.40 | 6.20 |
| LO10 | 5.50 | 5.80 | 5.68 | 6.09 |
| LO11 | 5.50 | 5.81 | 5.65 | 6.00 |
| LO14 | 5.12 | 5.62 | 5.62 | 5.62 |
| LO15 | 5.49 | 5.42 | 5.23 | 5.64 |
| Foam 09 | 5.63 | 6.06 | 5.69 | 6.10 |
| Foam 17 | 5.60 | 5.59 | 5.39 | 5.65 |
| Foam 18 | 5.68 | 5.73 | 5.68 | 5.93 |
| Foam 19 | 5.68 | 5.76 | 5.86 | 6.09 |
| Foam 20 | 5.79 | 5.63 | 6.08 | 6.02 |
| Foam 21 | 5.84 | 5.60 | 5.77 | 5.72 |

Example 14. Ruxolitinib Phosphate with
Alternative Bases

Part 1: Identifying Alternative Bases: Several alternative bases (i.e., alternative organic amine pH adjusting agents), with similar structures to trolamine, also were identified to run additional testing to determine whether the alternative bases have a comparable impact on ruxolitinib phosphate solubility and system apparent pH as trolamine; the alternative bases (including trolamine) are presented in Table 25.

TABLE 25

Potential alternative bases to trolamine.

| Trolamine (FDA IID listed) | Tris (FDA IID listed) | Ethanolamine (FDA IID listed, oral) |
|---|---|---|

| Diethanolamine (FDA IID listed) | Ammonia (FDA IID listed) | Diisopropanolamine (FDA IID listed) |
|---|---|---|

| 1-Amino-2-propanol (Not FDA IID listed) | 2-Amino-2-ethyl-1,3-propanediol (Not FDA IID listed) | 2-Amino-2-methyl-1-propanol (Not FDA IID listed) |
|---|---|---|

TABLE 25-continued

| Potential alternative bases to trolamine. | | |
|---|---|---|
| Diisopropylamine (Not FDA IID listed) | Imidazole (Not FDA IID listed) | Pyridine (Not FDA IID listed) |

The saturated solubility of ruxolitinib phosphate was assessed in the solvent systems detailed in Table 26, with each of the bases detailed in Table 25, and based on the following procedure:

(i) Ruxolitinib phosphate (ca. 25 mg) was weighed into individual suitably sized glass vials.

(ii) Each of the solvent systems (ca. 475 mg) was added to the individual glass vials from Step (i).

(iii) The drug and solvent systems were stirred for ca. 24 hr once saturation has been achieved in a pre-calibrated water bath at 20° C. During the 24 hr of stirring the solutions were visually inspected as required to observe if the drug has dissolved in the solvent systems.

(iv) If the drug was observed to dissolve (i.e. the system is unsaturated) additional drug will be added, and the 24 hr stir/observation period was restarted with each drug addition.

(v) For saturated systems, any undissolved drug was removed from the saturated solution via centrifugation. As much saturated solution as possible was transferred to an appropriate centrifuge tube and centrifuged at 20° C. for 10 min at ca. 16,000 g.

(vi) If after the first 10 min the solution was still visually saturated, the solution was transferred (taking care to avoid disturbing any API pellet present) to a fresh centrifuge tube and repeat the centrifugation. If a visually clear solution cannot be obtained, it may be necessary to repeat centrifugation using centrifuge filters.

(vii) Once a visually clear supernatant was obtained, the pH was measured and recorded.

(viii) A sample of the saturated supernatant was examined using light microscopy with a magnification of 200-1000×. If drug particles are present, the sample was centrifuged further until the supernatant is free from drug crystals.

(ix) An appropriate dilution/extraction of the supernatant was made to achieve a concentration of drug in sample diluent that is above the LOQ of a HPLC method, prior to analysis.

(x) The saturated solubility was calculated based on the concentration of drug observed in the analytical method and dilution procedure performed in Step (x).

TABLE 26

Compositions (% w/w) of the example solvent systems to be assessed in the identification of alternative bases* to Trolamine.

| Excipient | SSNA01 | SSAG01 | SSCR01 |
|---|---|---|---|
| Purified water | — | 34.95 | 42.45 |
| Polyethylene Glycol 200 | 53.50 | 28.45 | — |
| Glycerol | — | — | 15.00 |
| Hexylene glycol | 9.90 | — | — |
| Propylene Glycol | 18.00 | 15.00 | — |
| Transcutol P | 15.00 | 18.00 | 15.00 |
| Butylhydroxytoluene | 0.10 | 0.10 | — |
| Phenoxyethanol | — | — | 1.00 |
| Disodium EDTA | — | — | 0.05 |
| Polysorbate 80 | — | — | 3.00 |
| Base* | 3.50 | 3.50 | 3.50 |
| Total | 100.00 | 100.00 | 80.00 |

*Bases detailed in Table 25 were assessed.

In Table 27, a summary of the solvent systems listed above (i.e., SSNA01, SSAG01, and SSCR01) is provided for the alternative bases investigated including trolamine.

TABLE 27

| | Summary of the alternative bases data in the different solvent systems. | | | | | | | | |
|---|---|---|---|---|---|---|---|---|---|
| | SSNA01 | | | SSAG01 | | | SSCR01 | | |
| Base | Ruxolitinib solubility (% w/w) | Vehicle pH | Supernatant pH | Ruxolitinib solubility (% w/w) | Vehicle pH | Supernatant pH | Ruxolitinib solubility (% w/w) | Vehicle pH | Supernatant pH |
| Trolamine | 6.84 | 9.11 | 4.35 | 8.22 | 10.31 | 4.27 | 1.63 | 9.63 | 3.43 |
| Tris | | Incompatible | | | Incompatible | | 1.68 | 10.08 | 3.45 |
| Ethanolamine | 15.18 | 10.27 | 6.65 | 16.39 | 12.25 | 6.55 | 0.90 | 11.52 | 5.33 |
| Diethanolamine | 8.19 | 10.30 | 5.66 | | Incompatible | | 1.66 | 10.88 | 3.54 |
| Ammonia (25%) | 8.20 | 10.76 | 5.61 | | Incompatible | | 1.31 | 11.36 | 3.91 |
| Diisopropanolamine | 8.52 | 9.89 | 6.51 | 8.82 | 11.31 | 4.29 | 1.62 | 10.63 | 3.49 |
| 2-Amino-2-ethyl-1,3-propanediol | 8.96 | 10.27 | 4.99 | | Incompatible | | 1.84 | 10.38 | 3.29 |
| 2-Amino-2-methyl-l-propanol | 7.77 | 10.45 | 4.98 | 11.77 | 12.17 | 4.34 | 1.74 | 11.44 | 3.61 |

TABLE 27-continued

| | Summary of the alternative bases data in the different solvent systems. | | | | | | | | |
|---|---|---|---|---|---|---|---|---|---|
| | SSNA01 | | | SSAG01 | | | SSCR01 | | |
| Base | Ruxolitinib solubility (% w/w) | Vehicle pH | Supernatant pH | Ruxolitinib solubility (% w/w) | Vehicle pH | Supernatant pH | Ruxolitinib solubility (% w/w) | Vehicle pH | Supernatant pH |
| Diisopropylamine | 11.04 | 10.62 | 4.80 | 11.20 | 12.57 | 4.53 | Incompatible | | |
| Imidazole | 15.56 | 9.50 | 5.00 | 12.88 | 9.77 | 4.32 | 1.31 | 9.17 | 4.81 |
| Pyridine | 4.40 | 9.19 | 4.27 | 9.88 | 8.67 | 4.21 | 2.14 | 7.20 | 3.69 |

FDA IID Listed Bases:

For the SSNA01 solvent system in Table 27, Tris was found to be incompatible due to the absence of water in this solvent system. All other bases resulted in a greater solubility (by >2% w/w) of ruxolitinib phosphate than trolamine (6.84% w/w), with ethanolamine resulting in an especially high drug solubility of over double (15.18% w/w). Further, the bases maintained the apparent pH of SSNA01 following API addition similarly to trolamine (ca. 9-11) considering the variability associated with the measurement of apparent pH in non-aqueous systems (USP <791>).

For the SSAG01 solvent system, as with SSNA01, as provided in Table 27, tris was not compatible with this solvent system due to the low water content (ca. 34% w/w). Diethanolamine and ammonia (25%) were also incompatible with SSAG01 resulting in precipitation of BHT. Diisopropylamine resulted in a comparable ruxolitinib phosphate solubility to trolamine (ca. 8% w/w), however similarly to SSNA01, ethanolamine, resulted in a much greater solubility of the API (16.39% w/w). The ethanolamine system had a greater apparent pH (6.55) than the trolamine (4.27) and diisopropanolamine (4.29) systems, despite the greater amount of ruxolitinib phosphate dissolved in the ethanolamine system.

For the SSCR01 solvent system, as provided in Table 27, all bases were found to be compatible with SSCR01. Conversely to that observed with SSNA01 and SSAG01, ethanolamine resulted in the lowest API solubility in SSCR01 (0.9% w/w), with the remaining bases resulting in comparable ruxolitinib phosphate solubility to trolamine (ca. 1.6% w/w). However, as with SSAG01, ethanolamine in SSCR01 resulted in a ca. 2 unit higher apparent pH following drug addition (5.33) than the remaining bases. This is potentially due to the lower level of ruxolitinib phosphate dissolved in solution.

Overall, ruxolitinib phosphate solubility and the final system pH was generally consistent when the different bases were assessed within each solvent system, with the exception to this being ethanolamine. However, these trends were not consistent between the different solvent systems (e.g., SSCR01). Due to the acidic nature of ruxolitinib phosphate, it was expected that when API solubility was higher, the apparent pH of the final solution would be lower with the drug, as previously observed, overriding the base. However, in SSNA01 and SSAG01, this was not the case, as when API solubility was higher, so was the apparent pH of the final solution. This was especially notable when ethanolamine was included, where very high ruxolitinib phosphate solubility was observed (ca. 16% w/w) in SSNA01 and SSAG01, along with higher apparent pH (ca. 6.6), although the increase in apparent pH was not proportional to the increase in API solubility. As such, in SSNA01 and SSAG01 ethanolamine resulted in systems with more skin tolerable apparent pH than the other bases, with very high drug loadings. Interestingly, this was not the case in SSCR01, where a decrease in API solubility was observed in the presence of ethanolamine, despite this solvent system being a combination of SSAG01 and SSNA01, which are substantially different from each other.

Non-FDA IID Listed Bases:

For SSNA01, as provided in Table 27, with the exception of pyridine, all the compounds assessed resulted in a greater ruxolitinib phosphate solubility in SSNA01 than compared to trolamine (6.84% w/w), with the highest solubility observed when imidazole was used (15.56% w/w). Although pyridine resulted in the lowest API solubility (4.30% w/w) in SSNA01, and imidazole the greatest (15.65% w/w), these systems had comparable apparent pH the other bases that were assessed (pH 4-5).

For SSAG01, as provided in Table 27, 2-amino-2-ethyl-1,3-propanediol was found to be incompatible with this solvent system, resulting in precipitation of BHT. All other bases resulted in a greater ruxolitinib phosphate solubility (by 1.5-4.5% w/w) than then trolamine was included (8.22% w/w), and as with SSNA01, imidazole resulted in the greatest ruxolitinib phosphate solubility (12.88% w/w). Similarly, to SSNA01, the apparent pH of the solvent systems with each of the bases following API addition was comparable (ca. 4.2-4.5), despite the differences in drug solubility.

For SSCR01, as provided in Table 27, diisopropylamine was found to be incompatible with SSCR01, likely due to the high level of water in this system (42.45% w/w). Conversely to what was observed for SSNA01, pyridine resulted in the greatest solubility of ruxolitinib phosphate in SSCR01 (2.14% w/w), with imidazole resulting in the lowest API solubility (1.31% w/w). The remaining bases resulted in comparable API solubility to trolamine (ca. 1.3-1.8% w/w). Imidazole resulted in the highest apparent pH following API addition (4.81), with the remaining bases (including pyridine) resulting in a comparable apparent pH following API addition to trolamine (ca. 3.4-3.7).

Similarly, to the FDA IID listed bases, generally consistent ruxolitinib phosphate solubility and apparent pH was observed between bases within each solvent system assessed, with some interesting findings when imidazole and pyridine were assessed. Again, however these trends were not consistent between the different solvent systems (e.g., SSCR01). In SSNA01 (the anhydrous solvent system), imidazole resulted in a very high API solubility (ca. 16% w/w), and pyridine a low API solubility (ca. 4% w/w, compared to trolamine (ca. 7% w/w), with very little change in the apparent pH of the systems (ca. 4-5). As the level of water increased in the solvent system to 34.95% w/w in SSAG01, this difference in solubility reduced (ca. 13% w/w for imidazole, ca. 10% w/w for pyridine), however there was still no substantial difference in apparent pH (ca. 4). In the highest water system (SSCR01, 42.45% w/w), surprisingly imidazole resulted in the lowest API solubility (1.31% w/w), and pyridine the highest (2.14% w/w), and in this system there was a slight difference in apparent pH (4.81 for imidazole, 3.69 for pyridine). When comparing with the FDA IID listed bases, the inverse trend between API solubility and apparent pH was observed for ethanolamine.

Part 2: Identifying an Upper Limit for Trolamine: The current FDA IID limit for the topical application of trolamine is 11% w/w. This was investigated in a mixture design (DoE) which examines the point at which the level of Trolamine either stops having a positive effect on ruxolitinib phosphate solubility, or the point at which the apparent pH of the system becomes too high to be tolerated by the skin. This was performed in up to 3 solvent systems, and the upper limit of trolamine identified will be set in the mixture design (DoE).

The saturated solubility of ruxolitinib phosphate was assessed in the solvent systems detailed in Table 28. This data, and the apparent pH of the supernatant was used to support the upper limit of trolamine for investigation in the mixture design (DoE).

TABLE 29-continued

Data for SSNA compositions.

| Trolamine (% w/w) | First set up | | | Second set up | | |
|---|---|---|---|---|---|---|
| | Solubility (% w/w) | Vehicle pH | Final pH | Solubility (% w/w) | Vehicle pH | Final pH |
| 7.50 | 14.57 | 9.65 | 4.90 | 6.18* | 10.21 | 8.92 |
| 11.00 | 16.08 | 9.40 | 8.42 | 6.57* | 10.21 | 9.04 |
| 14.00 | 11.93 | 9.81 | 8.90 | 6.57* | 10.45 | 9.21 |
| 17.00 | 11.14 | 9.91 | 9.01 | 6.28* | 10.47 | 9.21 |
| 20.00 | 15.50 | 9.94 | 9.00 | 9.42* | 10.51 | 9.25 |

(-) Not assessed
(*) Immiscibility observed

As provided in Table 30 below, for SSAG, immiscibility was observed at levels of trolamine ≥11% w/w, and as such this experiment was not repeated.

TABLE 28

Compositions (% w/w) of the example solvent systems to be assessed in the identification of alternative bases to Trolamine.

| Excipient | SSN A02 | SSN A03 | SSN A04 | SSN A05 | SSA G02 | SSA G03 | SSA G04 | SSA G05 | SSC RO2 | SSC R03 | SSC RO4 | SSC RO4 |
|---|---|---|---|---|---|---|---|---|---|---|---|---|
| Purified water | | | | | 27.45 | 24.45 | 21.45 | 18.45 | 34.95 | 31.95 | 28.95 | 25.95 |
| Polyethylene Glycol 200 | 46.00 | 43.00 | 40.00 | 37.00 | 28.45 | 28.45 | 28.45 | 28.45 | — | — | — | — |
| Glycerol | — | — | — | — | — | — | — | — | 15.00 | 15.00 | 15.00 | 15.00 |
| Hexylene glycol | 9.90 | 9.90 | 9.90 | 9.90 | — | — | — | — | — | — | — | — |
| Propylene Glycol | 18.00 | 18.00 | 18.00 | 18.00 | 15.00 | 15.00 | 15.00 | 15.00 | — | — | — | — |
| Transcutol P | 15.00 | 15.00 | 15.00 | 15.00 | 18.00 | 18.00 | 18.00 | 18.00 | 15.00 | 15.00 | 15.00 | 15.00 |
| BHT | 0.10 | 0.10 | 0.10 | 0.10 | 0.10 | 0.10 | 0.10 | 0.10 | — | — | — | — |
| Phenoxyethanol | — | — | — | — | — | — | — | — | 1.00 | 1.00 | 1.00 | 1.00 |
| Disodium EDTA | — | — | — | — | — | — | — | — | 0.05 | 0.05 | 0.05 | 0.05 |
| Polysorbate 80 | — | — | — | — | — | — | — | — | 3.00 | 3.00 | 3.00 | 3.00 |
| Base | 11.00 | 14.00 | 17.00 | 20.00 | 11.00 | 14.00 | 17.00 | 20.00 | 11.00 | 14.00 | 17.00 | 20.00 |
| Total | 100.00 | 100.00 | 100.00 | 100.00 | 100.00 | 100.00 | 100.00 | 100.00 | 80.00 | 80.00 | 80.00 | 80.00 |

As provided in Table 29 below, for SSNA, variable ruxolitinib phosphate solubility was observed between 11 w/w % and 20% w/w trolamine, and as such the experiment was repeated. Very subtle immiscibility was observed at levels of trolamine ≥7.5% w/w, which was also likely to be present in the 1$^{st}$ set up. When no immiscibility was observed, good repeatability in the solubility of ruxolitinib phosphate was observed.

TABLE 29

Data for SSNA compositions.

| Trolamine (% w/w) | First set up | | | Second set up | | |
|---|---|---|---|---|---|---|
| | Solubility (% w/w) | Vehicle pH | Final pH | Solubility (% w/w) | Vehicle pH | Final pH |
| 0.00 | — | — | — | 1.66 | 8.92 | 3.77 |
| 3.50 | 6.84 | 9.11 | 4.35 | 6.88 | 9.75 | 5.30 |
| 5.50 | — | — | — | 6.91 | 10.10 | 8.53 |

TABLE 30

Data for SSAG compositions.

| Trolamine (% w/w) | First set up | | |
|---|---|---|---|
| | Solubility (% w/w) | Vehicle pH | Final pH |
| 3.50 | 8.22 | 10.31 | 4.27 |
| 7.50 | 14.53 | 10.38 | 4.00 |
| 11.00 | 18.13* | 10.73 | 6.33 |
| 14.00 | 19.26* | 10.77 | 7.34 |
| 17.00 | >20.00* | 10.67 | 7.76 |
| 20.00 | >20.00* | 10.78 | 8.15 |

(-) Not assessed
*Immiscibility observed

As provided in Table 31 below, for SSCR, variable ruxolitinib phosphate solubility was observed between 3.5 w/w % and 20% w/w trolamine, and as such the experiment was repeated. Very subtle immiscibility was observed at levels of trolamine ≥14% w/w, which was also likely to be present in the 1$^{st}$ set up. Variability between set ups was still observed, even when immiscibility was not observed, this was potentially due to intra-batch variability in the solubility of ruxolitinib phosphate.

TABLE 31

| | First set up | | | Second set up | | |
|---|---|---|---|---|---|---|
| Trolamine (% w/w) | Solubility (% w/w) | Vehicle pH | Final pH | Solubility (% w/w) | Vehicle pH | Final pH |
| 0.00 | — | — | — | 2.37 | 5.80 | 2.81 |
| 3.50 | 1.62 | 9.63 | 3.43 | 0.98 | 9.75 | 7.49 |
| 5.50 | — | — | — | 1.15 | 9.96 | 8.08 |
| 7.50 | 0.89 | 9.98 | 5.15 | 1.41 | 10.10 | 8.33 |
| 9.25 | — | — | — | 1.65 | 10.18 | 8.46 |
| 11.00 | 0.99 | 10.15 | 6.63 | 1.89 | 10.24 | 8.55 |
| 14.00 | 1.11 | 10.25 | 7.33 | 3.50* | 10.35 | 8.69 |
| 17.00 | 1.05 | 10.32 | 7.77 | 3.47* | 10.44 | 8.41 |
| 20.00 | 1.59 | 10.39 | 8.01 | _* | 10.53 | — |

Data for SSCR compositions.

(-) Not assessed
(*) Immiscibility observed

Generally, immiscibility was observed in the solvent systems at the following levels of trolamine: SSNA—≥7.5% w/w; SSAG—≥11% w/w; and SSCR—≥15% w/w. As such, it is not feasible to include trolamine at these levels or higher without concerns regarding the long term physical stability of the formulations. The apparent pH of the solvent systems was observed to be >pH 8 at the following levels of trolamine, where pH 8 is the recommended upper limit for topical application: SSNA—≥5.5% w/w; SSAG—could not be determined due to immiscibility; and SSCR—≥5.5% w/w. Considering these findings, the upper limit for trolamine will be set at 5.0% w/w for the mixture design DoE, to ensure relevance for topical application, and to minimise the risk of immiscibility being observed that may reduce the reliability of the results generated.

Part 3: Mixture Design (DoE): To understand the relationship between trolamine, ruxolitinib phosphate solubility, and system apparent pH, additional testing was performed as a mixture design (DoE). For example, a solvent system that could be included in any of the main topical dosage forms may be utilized, and the levels of the excipients, other than trolamine, will be varied between 0% and up to their FDA IID limit for topical application as per Table 33.

The saturated solubility of ruxolitinib phosphate was assessed in the runs detailed in Table 32 and the apparent pH of each run was measured before and after ruxolitinib phosphate addition. Following statistical analysis of the results, a selection saturated solubility experiments was performed to confirm the accuracy of the predictions made by the model.

TABLE 32

Excipient ranges over which the mixture
design (DoE) will be performed.

| Excipient | Lower limit (% w/w) | Lipper limit (% w/w) |
|---|---|---|
| Water | 0.00 | 100.00 |
| Glycerol | 0.00 | 20.00 |
| Transcutol P | 0.00 | 50.00 |
| PEG 400 | 0.00 | 99.00 |
| Trolamine | 0.00 | 11.00 |

TABLE 33

Compositions (% w/w) of the
runs assessed in the mixture design (DoE).

| | | | | Composition (% w/w) | | | |
|---|---|---|---|---|---|---|---|
| Run | | Water | Glycerol | Transcutol P | PEG 400 | Trolamine | Total |
| Block 1 | 1 | 28.61 | 10.39 | 50.00 | — | 11.00 | 100.00 |
| | 2 | 28.51 | 5.42 | 20.35 | 40.01 | 5.71 | 100.00 |
| | 3 | 63.05 | 20.00 | 5.00 | 11.95 | — | 100.00 |
| | 4 | 28.51 | 5.42 | 20.35 | 40.01 | 5.71 | 100.00 |
| | 5 | — | — | — | 89.00 | 11.00 | 100.00 |
| | 6 | 94.15 | 2.90 | — | — | 2.95 | 100.00 |
| | 7 | 22.67 | — | 43.93 | 33.40 | — | 100.00 |
| | 8 | 20.97 | 20.00 | 26.79 | 21.24 | 11.00 | 100.00 |
| | 9 | — | 20.00 | — | 76.05 | 3.95 | 100.00 |
| Block 2 | 10 | 60.76 | — | 19.59 | 8.65 | 11.00 | 100.00 |
| | 11 | 49.99 | 13.81 | 30.60 | — | 5.60 | 100.00 |
| | 12 | 34.18 | 10.30 | — | 44.52 | 11.00 | 100.00 |
| | 13 | 34.18 | 10.30 | — | 44.52 | 11.00 | 100.00 |
| | 14 | 10.69 | 20.00 | 5.72 | 52.59 | 11.00 | 100.00 |
| | 15 | 33.17 | — | — | 66.83 | — | 100.00 |
| | 16 | — | — | 50.00 | 44.02 | 5.98 | 100.00 |
| | 17 | — | 20.00 | 27.82 | 41.18 | 11.00 | 100.00 |
| | 18 | 49.99 | 13.81 | 30.60 | — | 5.60 | 100.00 |
| Block 3 | 19 | — | 8.69 | 27.89 | 63.42 | — | 100.00 |
| | 20 | 63.28 | — | — | 36.72 | — | 100.00 |
| | 21 | 50.00 | — | 50.00 | — | — | 100.00 |
| | 22 | 8.40 | 20.00 | 50.00 | 19.54 | 2.06 | 100.00 |
| | 23 | 39.57 | 9.39 | 16.11 | 29.91 | 5.02 | 100.00 |
| | 24 | 37.56 | — | 34.99 | 16.45 | 11.00 | 100.00 |
| | 25 | 39.57 | 9.39 | 16.11 | 29.91 | 5.02 | 100.00 |
| | 26 | 69.00 | 20.00 | — | — | 11.00 | 100.00 |
| | 27 | — | 8.69 | 27.89 | 63.42 | — | 100.00 |

In Table 34, the mixture of design DOE data is provided. From Table 34, there was a lack of fit observed upon the analysis of the ruxolitinib phosphate solubility (p-value <0.0001) and apparent pH (p-value <0.0458) from the mixture design DoE. Nevertheless, low variability was observed between replicate runs (1 and 5, 4 and 10, 17 and 18, 19 and 22, and 21 and 27): (1) In terms of ruxolitinib phosphate solubility, the greatest % CV between the replicates was 3.25; (2) In terms of apparent pH, the % CV between runs that had >30% water was <2.5, and in runs with <30% water, the variability was within ±1 pH unit, which is in line with expectations for low/non-aqueous systems as per USP <791>; and (3) This suggests that the lack of fit observed in the model was not as the result of variability in the solubility of ruxolitinib phosphate, as observed previously.

adjustment. The apparent pH of the phases will be monitored until the API was observed to visually dissolve.

(iv) The oil phases of the formulations will be prepared in separate amber Durans.

(v) For formulations containing a gelling agent, these will be dispersed in an appropriate liquid oil and will be stirred at 500 RPM until visually homogenous, then will be added to the vessel from Step (iv).

(vi) The oil phases will be placed into a water bath at 70° C. until melted (ca. 1 hr), or 90° C. for solid oil phases containing Kolliphor HCO. Additionally, the aqueous phases, liquid oil phases and homogeniser head will also be heated.

TABLE 34

| | | Composition (% w/w) | | | | | Ruxolitinib phosphate solubility | Final |
|---|---|---|---|---|---|---|---|---|
| Run | | Water | Glycerol | Transcutol P | PEG 400 | Trolamine | Total | (as freebase) | apparent pH |

<div>

Mixture of design DOE data.

| Run | | Water | Glycerol | Transcutol P | PEG 400 | Trolamine | Total | Ruxolitinib phosphate solubility (as freebase) | Final apparent pH |
|---|---|---|---|---|---|---|---|---|---|
| Block 1 | 1 | 29.17 | 8.22 | 50 | 12.61 | 0 | 100 | 3.528 | 3.57 |
| Block 1 | 2 | 0 | 0 | 42.54 | 55.47 | 1.99 | 100 | 1.65 | 6.75 |
| Block 1 | 3 | 53.69 | 20 | 13.77 | 7.54 | 5 | 100 | 0.75 | 7.89 |
| Block 1 | 4 | 33.81 | 4.4 | 0 | 59.16 | 2.63 | 100 | 6.254 | 4.65 |
| Block 1 | 5 | 29.17 | 8.22 | 50 | 12.61 | 0 | 100 | 3.422 | 3.12 |
| Block 1 | 6 | 47 | 0 | 48 | 0 | 5 | 100 | 10.886 | 4.61 |
| Block 1 | 7 | 42.66 | 0 | 16.58 | 40.76 | 0 | 100 | 2.132 | 3.92 |
| Block 1 | 8 | 4.06 | 20 | 30.02 | 45.92 | 0 | 100 | 2.348 | 3.24 |
| Block 1 | 9 | 0 | 7.15 | 0 | 92.85 | 0 | 100 | 1.162 | 4.1 |
| Block 1 | 10 | 33.81 | 4.4 | 0 | 59.16 | 2.63 | 100 | 6.159 | 4.51 |
| Block 2 | 11 | 62.7 | 2.5 | 0 | 34.8 | 0 | 100 | 1.499 | 4.2 |
| Block 2 | 12 | 28.02 | 20 | 50 | 0 | 1.98 | 100 | 5.844 | 3.82 |
| Block 2 | 13 | 77.95 | 4.23 | 0 | 12.82 | 5 | 100 | 0.054 | 7.24 |
| Block 2 | 14 | 13.47 | 20 | 1.24 | 61.35 | 3.94 | 100 | 9.156 | 4.22 |
| Block 2 | 15 | 0 | 0 | 7.13 | 87.87 | 5 | 100 | 1.765 | 8.46 |
| Block 2 | 16 | 19.87 | 0 | 23.4 | 56.73 | 0 | 100 | 3.315 | 3.54 |
| Block 2 | 17 | 67.28 | 8.06 | 22.48 | 0 | 2.18 | 100 | 0.765 | 3.62 |
| Block 2 | 18 | 67.28 | 8.06 | 22.48 | 0 | 2.18 | 100 | 0.801 | 3.72 |
| Block 3 | 19 | 6.1 | 12.71 | 43.24 | 32.95 | 5 | 100 | 7.944 | 6.4 |
| Block 3 | 20 | 51.06 | 0 | 28.38 | 18.56 | 2 | 100 | 3.048 | 3.79 |
| Block 3 | 21 | 31.14 | 9.96 | 24.44 | 32.22 | 2.24 | 100 | 5.878 | 4.11 |
| Block 3 | 22 | 6.1 | 12.71 | 43.24 | 32.95 | 5 | 100 | 7.977 | 7.23 |
| Block 3 | 23 | 100 | 0 | 0 | 0 | 0 | 100 | 1.267 | 3.95 |
| Block 3 | 24 | 21.05 | 0 | 0 | 78.95 | 0 | 100 | 2.898 | 3.54 |
| Block 3 | 25 | 27.42 | 20 | 6.11 | 41.47 | 5 | 100 | 10.154 | 4.22 |
| Block 3 | 26 | 70 | 20 | 0 | 10 | 0 | 100 | 1.233 | 5.67 |
| Block 3 | 27 | 31.14 | 9.96 | 24.44 | 32.22 | 2.24 | 100 | 6.016 | 4.17 |

</div>

Example 15: Ruxolitinib
Formulations/Compositions

The following topical formulations (or pharmaceutical compositions) in Tables 35 to 41 disclose topical formulations according to the present disclosure. The topical formulations are in a form chosen from creams, lotions, foams, pump sprays, aqueous gels, non-aqueous gels, and emulsified gels. The topical formulations in Tables 35 to 41 are prophetic.

Creams and Lotions

The following generic manufacturing methods are to be used for the preparation of cream and lotion formulations:

(i) The aqueous phases of the formulations will be prepared in amber Durans and stirred by magnetic stirrer bar at 400 RPM until visually homogenous.

(ii) For formulations containing EDTA and/or propyl gallate, these will be initially dissolved in a portion of the water and stirred at 400 RPM, then added to the vessel from Step (i).

(iii) Ruxolitinib phosphate will be added to the aqueous phases and stirred at 400 RPM for ca. 5 mins, before pH (vii) The three phases (aqueous, liquid oil and molten solid oil phase) will be combined, and homogenised using an IKA T25 Ultra Turrax for 2 mins at 10,000 RPM.

(viii) Following homogenisation, the formulations will be allowed to cool to room temperature whilst stirring using an IKA stirrer at 200 RPM.

(ix) Once the formulation had reached room temperature, phenoxyethanol will be added and the formulation hand stirred until incorporated.

(x) The apparent pH of the formulation will be checked, and any final pH adjustment, or Q.S. with water completed.

Foams

The following generic manufacturing method will be used for the preparation of foam formulations:

(i) The foam premixes will be manufactured as per the methods used for the manufacture of creams and lotions.

(ii) Foam premixes will be added to canisters and valves will be crimped on.

(iii) Propellant will be added to the canisters from Step (ii) using the Pamasol.

(iv) The completed foams will be left to mix on a roller mixer overnight.

Pump Sprays

The following generic manufacturing method will be used for the preparation of pump sprays:

(i) BHT will be added to ethanol and stirred by magnetic stirrer bar for ca. 15 mins at 500 RPM, until visually dissolved.

(ii) Poloxamer or gantrez will be added to the vessel from Step (i) and will be stirred for ca. 30 mins at 500 RPM, until visually dissolved.

(iii) The remaining excipients will be added to the vessel from Step (iii) and the solution stirred for ca. 10 mins at 500 RPM, until visually homogenous.

(iv) Ruxolitinib phosphate will be added to the vessel from Step (iii) and stirred for ca. 1 hr at 500 RPM, until visually dissolved, and the solution pH adjusted.

Aqueous Gels

The following generic manufacturing method will be used for the preparation of aqueous gels:

(i) The solvent systems will be prepared in amber Durans and stirred by magnetic stirrer bar at 400 RPM until visually homogenous.

(ii) For formulations containing EDTA, this will be initially dissolved in a portion of the water and stirred at 400 RPM, then added to the vessel from Step (i).

(ii) For formulations containing BHT, this will be initially dissolved in the Transcutol P and stirred at 400 RPM, then added to the vessel from Step (i).

(iii) Ruxolitinib phosphate will be added to the solvent systems and stirred at 400 RPM for ca. 5 mins before pH adjustment. The apparent pH of the solvent system will be monitored until the API was observed to fully dissolve, and the target apparent pH reached.

(iv) Following complete dissolution of the API, the gelling agent will be added to the solvent system from Step (iv) and stirred at 400 RPM until visually homogenous.

Non-Aqueous Gels

The following generic manufacturing method will be used for the preparation of non-aqueous gels:

(i) The solvent systems will be prepared in amber Durans and stirred by magnetic stirrer bar at 400 RPM until visually homogenous.

(ii) For formulations containing BHT, this will be initially dissolved in the Transcutol P and stirred at 400 RPM, then added to the vessel from Step (i).

(iii) Ruxolitinib phosphate will be added to the solvent systems and stirred at 400 RPM for ca. 5 mins before pH adjustment. The apparent pH of the solvent system will be monitored until the API was observed to fully dissolve, and the target apparent pH reached.

(iv) Following complete dissolution of the API, the gelling agent will be added to the solvent system from Step (iv) and stirred at 400 RPM until visually homogenous.

Emulsified Gels

The following generic manufacturing method will be used for the preparation of emulsified gels:

(i) The aqueous phases of the formulations will be prepared in amber Durans and stirred by magnetic stirrer bar at 400 RPM until visually homogenous.

(ii) For formulations containing EDTA, this will be initially dissolved in a portion of the water and stirred at 400 RPM, then added to the vessel from Step (i).

(iii) Ruxolitinib phosphate will be added to the aqueous phases and stirred at 400 RPM for ca. 5 mins, before pH adjustment. The apparent pH of the phases will be monitored until the API was observed to visually dissolve, and the target apparent pH reached.

(iv) The oil phases of the formulations will be prepared in separate amber Durans. The Sepineo P600 will be dispersed in the oil phases and stirred at 500 RPM until visually homogenous.

(v) The aqueous phase (from Step (iii)) and the oil phase (from Step (v)) will be combined and homogenised using an IKA T25 Ultra Turrax for 2 mins at 10,000 RPM.

(vi) Following homogenisation, the formulations will be allowed to cool to room temperature whilst stirring using an IKA stirrer at 200 RPM.

(vii) The apparent pH of the formulation will be checked, and any final pH adjustment, or Q. S. with water completed.

TABLE 35

Prophetic Cream Formulations

| | Cream formulations | | | | | |
|---|---|---|---|---|---|---|
| Excipients | CR01 PBO SSCR06 | CR02 PBO SSCR11 | CR03 ACT SSCR06 | CR04 ACT SSCR11 | CR06 ACT SSCR29 | CR07 ACT SSCR06 |
| Ruxolitinib phosphate (free base) | — | — | 1.45 (1.10) | 0.81 (0.61) | 1.45 (1.10) | 1.45 (1.10) |
| Water | 23.55 | 44.90 | 22.10 | 44.09 | 42.00 | 29.00 |
| PEG 400 | 8.00 | — | 8.00 | — | — | 8.00 |
| Glycerol | 20.00 | — | 20.00 | — | 15.00 | 20.00 |
| Propylene glycol | 10.00 | — | 10.00 | — | — | 10.00 |
| Transcutol P | — | 15.00 | — | 15.00 | 15.00 | — |
| Methyl paraben | — | 0.10 | — | 0.10 | — | — |
| Propyl paraben | — | 0.05 | — | 0.05 | — | — |
| Benzyl alcohol | 2.00 | — | 2.00 | — | — | — |
| Disodium EDTA | 0.05 | 0.05 | 0.05 | 0.05 | 0.05 | 0.05 |
| Polysorbate 80 | — | 3.00 | — | 3.00 | 3.00 | — |
| Glyceryl monostearate (Kolliwax GMSII) | 3.00 | 3.00 | 1.91 | — | — | — |
| Brij S2 | — | — | — | 2.00 | 1.37 | 3.61 |
| Brij S721 | — | — | — | 3.00 | — | 1.39 |

TABLE 35-continued

| Prophetic Cream Formulations | | | | | | |
|---|---|---|---|---|---|
| Span 80 | — | — | — | — | — | — |
| Cetomacrogol 1000 | — | — | 3.09 | — | 3.63 | — |
| Polawax NF | — | — | 6.00 | — | — | 6.50 |
| Cetyl alcohol | 3.00 | 3.00 | — | 4.00 | 3.00 | — |
| Stearyl alcohol | 1.75 | 1.75 | — | 2.00 | 2.00 | — |
| Cetostearyl alcohol | — | — | 2.00 | — | — | — |
| Light Mineral Oil | 4.00 | 4.00 | 5.00 | — | 3.00 | 5.00 |
| White Soft Paraffin | 7.00 | 7.00 | — | — | — | — |
| Castor oil | — | — | — | — | — | 3.00 |
| Hydrogenated castor oil (Kolliphor HCO) | — | — | — | — | — | — |
| Isopropyl myristate | — | — | — | 5.00 | — | — |
| GTCC | 5.00 | 5.00 | 7.40 | 10.40 | 7.00 | 8.91 |
| ST-Cyclomethicone 5-NF | — | — | 1.00 | — | — | — |
| Kolliphor OD | — | — | — | — | — | — |
| Dimethicone 350 | 1.00 | 1.00 | — | — | — | — |
| Polysorbate 20 | 1.25 | 1.25 | — | — | — | — |
| Xanthan gum | 0.40 | 0.40 | — | — | — | — |
| Phosphoric acid solution | To pH 5.5* | To pH 5.5* | To pH 5.5* | To pH 5.5* | To pH 5.5* | To pH 5.5* |
| Trolamine | | | | | | |
| 2nd addition of water | Q.S. | Q.S. | Q.S. | Q.S. | Q.S. | Q.S. |
| Phenoxyethanol | — | 0.50 | — | 0.50 | 1.00 | 1.00 |
| Total | 100.00 | 100.00 | 100.00 | 100.00 | 100.00 | 100.00 |

| Cream formulations | | | | | | |
|---|---|---|---|---|---|
| Excipients | CR09 ACT SSCR28 | CR10 ACT SSCR28 | CR13 ACT SSCR30 | CR14 ACT SSCR30 | CR15 ACT SSCR06 | CR16 ACT SSCR29 |
| Ruxolitinib phosphate (free base) | 1.36 (1.03) | 1.36 (1.03) | 1.45 (1.10) | 1.45 (1.10) | 1.45 (1.10) | 1.45 (1.10) |
| Water | 30.00 | 30.00 | 37.00 | 37.00 | 26.00 | 42.00 |
| PEG 400 | 12.00 | 12.00 | — | — | 8.00 | — |
| Glycerol | 20.00 | 20.00 | 20.00 | 20.00 | 20.00 | 15.00 |
| Propylene glycol | 10.00 | 10.00 | — | — | 10.00 | — |
| Transcutol P | — | — | 18.00 | 18.00 | — | 15.00 |
| Methyl paraben | — | — | — | — | — | — |
| Propyl paraben | — | — | — | — | — | — |
| Benzyl alcohol | — | — | — | — | — | — |
| Disodium EDTA | 0.05 | 0.05 | 0.05 | 0.05 | 0.05 | 0.05 |
| Polysorbate 80 | 3.00 | 3.00 | — | — | — | 3.00 |
| Glyceryl monostearate (Kolliwax GMSII) | — | — | — | 1.49 | — | 3.00 |
| Brij S2 | 1.39 | — | 2.00 | — | — | — |
| Brij S721 | 2.61 | — | 3.00 | — | — | — |
| Span 80 | — | — | — | — | — | — |
| Cetomacrogol 1000 | — | 1.80 | — | 3.51 | 1.80 | — |
| Polawax NF | — | — | 6.50 | — | — | — |
| Cetyl alcohol | — | — | — | 3.00 | — | 3.00 |
| Stearyl alcohol | — | — | — | 2.00 | — | 1.75 |
| Cetostearyl alcohol | 4.10 | 8.00 | — | — | 7.61 | — |
| Light Mineral Oil | 3.00 | 4.00 | 2.50 | 8.00 | 8.00 | 2.70 |
| White Soft Paraffin | — | 2.00 | — | — | 2.00 | 5.50 |
| Castor oil | — | — | — | — | — | — |
| Hydrogenated castor oil (Kolliphor HCO) | 2.00 | — | — | 2.00 | — | — |
| Isopropyl myristate | — | — | — | — | — | — |
| GTCC | 5.00 | 4.20 | 6.00 | — | 9.00 | 3.65 |
| ST-Cyclomethicone 5-NF | 1.50 | — | — | — | — | — |

TABLE 35-continued

| Prophetic Cream Formulations | | | | | | |
|---|---|---|---|---|---|---|
| Kolliphor OD | — | — | — | — | — | — |
| Dimethicone 350 | — | — | — | — | — | — |
| Polysorbate 20 | — | — | — | — | — | — |
| Xanthan gum | 0.40 | — | — | — | — | 0.40 |
| Phosphoric acid solution | To pH5.5* | To pH5.5* | To pH5.5* | To pH5.5* | To pH5.5* | To pH5.5* |
| Trolamine 2nd addition of water | Q.S. | Q.S. | Q.S. | Q.S. | Q.S. | Q.S. |
| Phenoxyethanol | 1.00 | 1.00 | 1.00 | 1.00 | 1.00 | 1.00 |
| Total | 100.00 | 100.00 | 100.00 | 100.00 | 100.00 | 100.00 |

TABLE 36

| Prophetic Lotion Formulations | | | | | | |
|---|---|---|---|---|---|---|
| | Lotion formulations | | | | | |
| Excipients | LO01 (CR02) SSCR11 | LO02 ACT SSCR29 | LO03 ACT SSCR29 | LO04 ACT SSCR29 | LO05 ACT SSCR29 | LO06 ACT SSCR28 |
| Ruxolitinib phosphate (free base) | — | 1.30 (0.98) | 1.30 (0.98) | 1.30 (0.98) | 1.30 (0.98) | 1.36 (1.03) |
| Water | 44.90 | 39.00 | 39.00 | 39.00 | 39.00 | 27.00 |
| PEG 400 | — | — | — | — | — | 12.00 |
| Glycerol | — | 15.00 | 15.00 | 15.00 | 15.00 | 20.00 |
| Propylene glycol | — | — | — | — | — | 10.00 |
| Transcutol P | 15.00 | 15.00 | 15.00 | 15.00 | 15.00 | — |
| Methyl paraben | 0.10 | — | — | — | — | — |
| Propyl paraben | 0.05 | — | — | — | — | — |
| Disodium EDTA | 0.05 | 0.05 | 0.05 | 0.05 | 0.05 | 0.05 |
| Polysorbate 80 (Tween 80) | 3.00 | 3.00 | 3.00 | 3.00 | 3.00 | 3.00 |
| Brij S2 | — | 2.18 | — | — | — | — |
| Brij S721 | — | 2.82 | — | — | — | — |
| Span 80 | — | — | — | 4.00 | — | — |
| Glyceryl mono-stearate (GMS II) | 3.00 | — | — | — | 1.20 | — |
| Cetomacrogol 1000 | — | — | — | — | — | 1.80 |
| Arlacel 165 (Glyceryl Stearate (and) PEG-100 Stearate) | — | — | 5.00 | — | 3.80 | — |
| Cetostearyl alcohol | — | — | 2.00 | 3.00 | — | 6.20 |
| Cetyl alcohol | 3.00 | 3.00 | — | — | — | — |
| Stearyl alcohol | 1.75 | — | — | — | — | — |
| Polawax NF | — | — | — | — | 2.00 | — |
| Light Mineral Oil | 4.00 | 3.50 | 3.00 | — | 3.00 | 4.00 |
| White Soft Paraffin | 7.00 | 1.50 | — | — | — | 2.00 |
| Isopropyl myristate | — | — | 3.00 | 4.00 | 4.80 | — |
| Medium chain triglyceride (Crodamol GTCC) | 5.00 | 7.00 | 7.00 | 9.00 | 5.00 | 6.00 |
| ST-Cyclomethicone 5-NF | — | — | — | — | — | — |
| Dimethicone 350 | 1.00 | — | — | — | — | — |
| Polysorbate 20 | 1.25 | — | — | — | — | — |
| Xanthan gum | 0.40 | — | — | — | 0.20 | — |
| Kolliphor OD | — | — | — | — | — | — |
| Phosphoric acid solution Trolamine | To pH 5.5* | To pH 5.5* | To pH 5.5* | To pH 5.5* | To pH 5.5* | To pH 5.5* |
| 2nd addition of water | Q.S. | Q.S. | Q.S. | Q.S. | Q.S. | Q.S. |
| Phenoxyethanol | 0.50 | 1.00 | 1.00 | 1.00 | 1.00 | 1.00 |
| Total | 100.00 | 100.00 | 100.00 | 100.00 | 100.00 | 100.00 |

TABLE 36-continued

Prophetic Lotion Formulations

| | Lotion formulations | | | | |
|---|---|---|---|---|---|
| Excipients | LO07 ACT SSCR28 | LO10 ACT SSCR28 | LO11 ACT SSCR28 | LO14 ACT SCR06 | LO15 ACT SSCR29 |
| Ruxolitinib phosphate (free base) | 1.36 (1.03) | 1.36 (1.03) | 1.21 (0.92) | 1.45 (1.10) | 1.45 (1.10) |
| Water | 30.00 | 27.00 | 30.00 | 29.00 | 42.00 |
| PEG 400 | 12.00 | 12.00 | 12.00 | 8.00 | — |
| Glycerol | 20.00 | 20.00 | 20.00 | 20.00 | 15.00 |
| Propylene glycol | 10.00 | 10.00 | 10.00 | 10.00 | — |
| Transcutol P | — | — | — | — | 15.00 |
| Methyl paraben | — | — | — | — | — |
| Propyl paraben | — | — | — | — | — |
| Disodium EDTA | 0.05 | 0.05 | 0.05 | 0.05 | 0.05 |
| Polysorbate 80 (Tween 80) | 3.00 | 3.00 | 3.00 | — | 3.00 |
| Brij S2 | 2.18 | 2.00 | — | — | 2.18 |
| Brij S721 | 2.82 | 3.00 | — | — | 2.82 |
| Span 80 | — | — | — | — | — |
| Glyceryl mono-stearate (GMS II) | — | — | — | 0.36 | — |
| Cetomacrogol 1000 | — | — | 1.80 | 4.64 | — |
| Arlacel 165 (Glyceryl Stearate (and) PEG-100 Stearate) | — | — | — | — | — |
| Cetostearyl alcohol | — | 3.00 | 5.00 | — | — |
| Cetyl alcohol | 3.00 | — | — | — | 5.00 |
| Stearyl alcohol | — | — | — | — | — |
| Polawax NF | — | — | — | 8.00 | — |
| Light Mineral Oil | 3.50 | 4.50 | 4.00 | — | 3.50 |
| White Soft Paraffin | 1.50 | — | 2.00 | — | 1.50 |
| Isopropyl myristate | — | 6.00 | — | 3.41 | — |
| Medium chain triglyceride (Crodamol GTCC) | 7.00 | — | 7.20 | 10.00 | 5.00 |
| ST-Cyclomethicone 5-NF | — | 1.50 | — | — | — |
| Dimethicone 350 | — | — | — | — | — |
| Polysorbate 20 | — | — | — | — | — |
| Xanthan gum | — | 0.20 | — | — | — |
| Kolliphor OD | — | — | — | 2.00 | — |
| Phosphoric acid solution | To pH5.5* | To pH5.5* | To pH5.5* | To pH5.5* | To pH5.5* |
| Trolamine | | | | | |
| 2nd addition of water | Q.S. | Q.S. | Q.S. | Q.S. | Q.S. |
| Phenoxyethanol | 1.00 | 1.00 | 1.00 | 1.00 | 1.00 |
| Total | 100.00 | 100.00 | 100.00 | 100.00 | 100.00 |

*The pH can be prepared over a pH range from 2.0 to 8.0.

TABLE 37

Prophetic Foam Formulations

| | Foam formulations | | | | | | | |
|---|---|---|---|---|---|---|---|---|
| Excipients | Foam 06 LO07 ACT | Foam 07 LO07 ACT | Foam 09 LO07 ACT | Foam 17 Foam premix 2 | Foam 18 Foam premix 1 | Foam 19 Foam premix 3 | Foam 20 Foam premix 4 | Foam 21 SSCR29 |
| Ruxolitinib phosphate (free base) | 1.08 (0.82) | 0.95 (0.72) | 1.22 (0.92) | 1.16 (0.88) | 1.22 (0.92) | 1.16 (0.88) | 1.16 (0.88) | 1.16 (0.88) |
| Ruxolitinib phosphate | 1.08 | 0.95 | 1.22 | 1.16 | 1.22 | 1.16 | 1.16 | 1.16 |
| Water | 24.00 | 21.00 | 27.00 | 29.60 | 27.00 | 24.00 | 33.60 | 33.60 |
| PEG 400 | 9.60 | 8.40 | 10.80 | — | 10.80 | 9.60 | — | — |
| Glycerol | 16.00 | 14.00 | 18.00 | 16.00 | 18.00 | 16.00 | 12.00 | 12.00 |
| Propylene glycol | 8.00 | 7.00 | 9.00 | — | 9.00 | 8.00 | | — |
| Transcutol P | — | — | — | 14.40 | — | — | 12.00 | 12.00 |
| Disodium EDTA | 0.04 | 0.04 | 0.05 | 0.04 | 0.05 | 0.04 | 0.04 | 0.04 |
| Polysorbate 80 | 2.40 | 2.10 | 2.70 | — | 2.70 | 2.40 | 2.40 | 2.40 |

TABLE 37-continued

Prophetic Foam Formulations

| | Foam formulations | | | | | | | |
|---|---|---|---|---|---|---|---|---|
| Excipients | Foam 06 LO07 ACT | Foam 07 LO07 ACT | Foam 09 LO07 ACT | Foam 17 Foam premix 2 | Foam 18 Foam premix 1 | Foam 19 Foam premix 3 | Foam 20 Foam premix 4 | Foam 21 SSCR29 |
| (Tween 80) | | | | | | | | |
| Brij S2 | 1.74 | 1.53 | 1.96 | — | 1.67 | 3.20 | — | — |
| Brij S721 | 2.26 | 1.97 | 2.54 | — | — | — | — | — |
| Cetomacrogol 1000 | — | — | — | — | — | — | — | — |
| Polawax NF | — | — | — | — | — | — | — | — |
| Kolliphor CSA 50 | — | — | — | 4.00 | — | — | 4.00 | 4 |
| Kolliphor CS20 | — | — | — | 4.80 | — | 4.00 | 4.80 | 4.80 |
| Kollicream 3C | — | — | — | 2.00 | — | — | 2.00 | 2 |
| PEG 4000 | — | — | — | — | 14.18 | 5.21 | — | — |
| Cetostearyl alcohol | — | — | — | — | — | — | — | — |
| Cetyl alcohol | 2.40 | 2.10 | 2.70 | — | — | — | — | — |
| Stearyl alcohol | — | — | — | — | 1.80 | — | — | — |
| Light Mineral Oil | 2.80 | 2.45 | 3.15 | 5.20 | — | 3.20 | 5.20 | 5.20 |
| White Soft Paraffin | 1.20 | 1.05 | 1.35 | — | — | — | — | — |
| Castor Oil | — | — | — | — | — | — | — | — |
| Medium chain triglyceride (Crodamol GTCC) | 5.60 | 4.90 | 6.30 | — | — | — | — | — |
| Xanthan gum | — | — | — | — | 0.36 | 0.32 | — | — |
| Phosphoric acid solution Trolamine | To pH 5.5* | To pH 5.5* | To pH 5.5* | To pH 5.5* | To pH 5.5* | To pH 5.5* | To pH 5.5* | To pH 5.5* |
| 2nd addition of water | to 80% | to 70% | to 90% | to 80% | to 80% | to 80% | to 80% | to 80% |
| Phenoxyethanol | 0.80 | 0.70 | 0.90 | 0.80 | 0.80 | 0.80 | 0.80 | 0.80 |
| Sub-total | 80.00 | 70.00 | 90.00 | 80.00 | 80.00 | 80.00 | 80.00 | 80.00 |
| HFA-134 | 20.00 | 30.00 | — | 20.00 | 20.00 | 20.00 | 20.00 | — |
| DME | — | — | 10.00 | — | — | — | — | — |
| HFO-1234ze | — | — | — | — | — | — | — | 20 |
| Total | 100.00 | 100.00 | 100.00 | 100.00 | 100.00 | 100.00 | 100.00 | 100.00 |

*The pH can be prepared over a pH range from 2.0 to 8.0.

35

TABLE 38

Prophetic Pump Spray Formulations

| | Pump spray formulations | | | | | |
|---|---|---|---|---|---|---|
| Excipient | Sol10 | Sol12 | Sol13 | Sol14 | Sol15 | Sol16 |
| Water | 19.00 | 10.00 | 18.00 | 19.00 | 22.00 | 17.00 |
| PEG 400 | — | — | 4.00 | — | — | — |
| Glycerol | 9.00 | 9.00 | 9.00 | 9.00 | 5.00 | 3.00 |
| Propylene glycol | — | — | 10.00 | — | — | — |
| Sorbitol | — | — | — | — | — | — |
| Transcutol P | 13.00 | 13.00 | — | 13.00 | 8.00 | 5.00 |
| Phenoxyethanol | 1.00 | 1.00 | 1.00 | 1.00 | 1.00 | 1.00 |
| Disodium EDTA | — | — | — | — | — | — |
| BHT | — | 0.10 | 0.10 | 0.10 | 0.10 | 0.10 |
| Ethanol | 50.00 | 50.00 | 50.00 | 50.00 | 60.00 | 70.00 |
| Eudragit E 100 | — | — | — | — | — | — |
| Eudragit RL 100 | — | — | — | — | — | — |
| Poloxamer 407 | 1.00 | — | 1.00 | — | 1.00 | 1.00 |
| Gantrez ES-435 | — | 10.00 | — | — | — | — |
| Kollidon 90F | — | — | — | 0.50 | — | — |
| Phosphoric acid solution Trolamine | To pH 5.5* | To pH 5.5* | To pH 5.5* | To pH 5.5* | To pH 5.5* | To pH 5.5* |
| 2nd addition of water | Q.S. | Q.S. | Q.S. | Q.S. | Q.S. | Q.S. |
| Total | 100.00 | 100.00 | 100.00 | 100.00 | 100.00 | 100.00 |

| | Pump spray formulations | | | | | |
|---|---|---|---|---|---|---|
| Excipient | Sol17 | Sol18 | Sol19 | Sol20 | Sol21 | Sol22 |
| Water | 15.00 | 23.00 | 19.00 | 15.00 | 27.50 | 19.00 |
| PEG 400 | — | — | — | — | — | — |

TABLE 38-continued

Prophetic Pump Spray Formulations

| Glycerol | 5.00 | 5.00 | 3.00 | 3.00 | 3.00 | — |
|---|---|---|---|---|---|---|
| Propylene glycol | — | — | — | — | — | 3.00 |
| Sorbitol | — | — | — | — | — | — |
| Transcutol P | 11.00 | 8.00 | 3.00 | 5.00 | 3.00 | 3.00 |
| Phenoxyethanol | 1.00 | 1.00 | 1.00 | 1.00 | 1.00 | 1.00 |
| Disodium EDTA | — | — | — | — | — | — |
| BHT | 0.10 | 0.10 | 0.10 | 0.10 | 0.10 | 0.10 |
| Ethanol | 55.00 | 60.00 | 70.00 | 63.00 | 62.40 | 70.00 |
| Eudragit E 100 | — | — | — | — | — | — |
| Eudragit RL 100 | — | — | — | — | — | — |
| Poloxamer 407 | — | — | 1.00 | — | — | 1.00 |
| Gantrez ES-435 | 10.00 | — | — | 10.00 | — | — |
| Kollidon 90F | — | 0.50 | — | — | 0.50 | — |
| Phosphoric acid solution | To pH5.5* | To pH5.5* | To pH5.5* | To pH5.5* | To pH5.5* | To pH5.5* |
| Trolamine | | | | | | |
| 2nd addition of water | Q.S. | Q.S. | Q.S. | Q.S. | Q.S. | Q.S. |
| Total | 100.00 | 100.00 | 100.00 | 100.00 | 100.00 | 100.00 |

*The pH can be prepared over a pH range from 2.0 to 8.0.

TABLE 39

Prophetic Aqueous Gel Formulations

| | Aqueous gel formulations | | | | |
|---|---|---|---|---|---|
| Excipients | AG01 | AG02 | AG03 | AG04 | AG05 |
| Ruxolitinib phosphate | TBC | TBC | TBC | TBC | TBC |
| Water | 44.45 | 15.00 | 49.45 | 42.45 | 12.40 |
| PEG 400 | — | — | 10.00 | — | 45.00 |
| Glycerol | 20.00 | 19.00 | 5.00 | 20.00 | — |
| Propylene glycol | — | 15.00 | — | 10.00 | 15.00 |
| Transcutol P | 20.00 | 38.40 | 20.00 | 10.00 | 15.00 |
| Disodium EDTA | 0.05 | — | 0.05 | 0.05 | — |
| BHT | — | 0.10 | — | — | 0.10 |
| Polysorbate 80 (Tween 80) | 3.00 | — | — | 5.00 | — |
| Polyoxyl 35 castor oil | — | — | 3.00 | — | — |
| Phenoxyethanol | 1.00 | 1.00 | 1.00 | 1.00 | 1.00 |
| Phosphoric acid solution | To pH 5.0-8.0 | To pH 5.0-8.0 | To pH 5.0-8.0 | To pH 5.0-8.0 | To pH 5.0-8.0 |
| Trolamine | | | | | |
| 2nd addition of water | Q.S to 100% | — | Q.S to 100% | Q.S to 100% | Q.S to 100% |
| 2nd addition of Transcutol P | — | Q.S to 100% | — | — | — |
| Hydroxyethyl cellulose | — | — | 1.50 | 1.50 | — |
| Hypermellose | 1.50 | — | — | — | — |
| Hydroxypropyl Cellulose | — | 1.50 | — | — | 1.50 |
| Total | 100.00 | 100.00 | 100.00 | 100.00 | 100.00 |

TABLE 40

Prophetic Non-aqueous Gel Formulations

| | Non-aqueous gel formulations | | | | |
|---|---|---|---|---|---|
| Excipients | NA01 TBC | NA02 TBC | NA03 TBC | NA04 TBC | NA05 SSNA03 |
| Ruxolitinib phosphate | TBC | TBC | TBC | TBC | TBC |
| Ethanol | 20.00 | 10.00 | — | 15.00 | — |
| Hexylene Glycol | 12.00 | — | — | — | 9.90 |
| DIPA | — | — | 15.00 | — | — |
| PEG 400 | 17.00 | — | 15.00 | — | 50.50 |
| Glycerol | 20.00 | 20.00 | — | 20.00 | — |
| Propylene glycol | — | 20.00 | 20.00 | 20.00 | 18.00 |
| Transcutol P | 24.40 | 43.40 | 43.40 | 38.40 | 15.00 |
| BHT | 0.10 | 0.10 | 0.10 | 0.10 | 0.10 |
| Phosphoric acid | To pH | To pH | To pH | To pH | To pH |

TABLE 40-continued

Prophetic Non-aqueous Gel Formulations

| | Non-aqueous gel formulations | | | | |
|---|---|---|---|---|---|
| Excipients | NA01 TBC | NA02 TBC | NA03 TBC | NA04 TBC | NA05 SSNA03 |
| solution | 5.0-8.0 | 5.0-8.0 | 5.0-8.0 | 5.0-8.0 | 5.0-8.0 |
| Trolamine | | | | | |
| 2nd addition of Transcutol P | Q.S to 100% | Q.S to 100% | Q.S to 100% | Q.S to 100% | — |
| 2nd addition of PEG 400 | — | — | — | — | Q.S to 100% |
| Hydroxypropyl Cellulose | 1.50 | 1.50 | 1.50 | 1.50 | 1.50 |
| Total | 100.00 | 100.00 | 100.00 | 100.00 | 100.00 |

TABLE 41

| | Prophetic Emulsified Gel Formulations | | | | |
|---|---|---|---|---|---|
| | Emulsified gel formulations | | | | |
| Excipients | EG01 | EG02 | EG03 | EG04 | EG05 |
| Ruxolitinib phosphate | TBC | TBC | TBC | TBC | TBC |
| Water | 36.95 | 36.95 | 36.95 | 35.95 | 35.00 |
| PEG 400 | — | — | — | — | 14.95 |
| Glycerol | 20.00 | 20.00 | 20.00 | 20.00 | — |
| Propylene glycol | — | — | — | 10.00 | 15.00 |
| Transcutol P | 20.00 | 15.00 | 20.00 | 10.00 | 15.00 |
| Disodium EDTA | 0.05 | 0.05 | 0.05 | 0.05 | 0.05 |
| Polysorbate 80 (Tween 80) | 3.00 | 3.00 | 3.00 | — | — |
| Polyoxyl 35 castor oil | — | — | — | 4.00 | — |
| Phenoxyethanol | 1.00 | 1.00 | 1.00 | 1.00 | 1.00 |
| Phosphoric acid solution Trolamine | To pH 5.0-8.0 | To pH 5.0-8.0 | To pH 5.0-8.0 | To pH 5.0-8.0 | To pH 5.0-8.0 |
| 2nd addition of water | Q.S to 100% | Q.S to 100% | Q.S to 100% | Q.S to 100% | Q.S to 100% |
| Light Mineral Oil | — | — | — | 10.00 | — |
| Castor Oil | 10.00 | — | — | — | — |
| Medium Chain Triglycerides | — | 10.00 | 10.00 | — | 10.00 |
| Isopropyl myristate | — | 5.00 | — | — | — |
| Sepineo P600 | 4.00 | 4.00 | 4.00 | 4.00 | 4.00 |
| Total | 100.00 | 100.00 | 100.00 | 100.00 | 100.00 |

Example 16. Additional Short-Term Stability Testing

Additional formulations were selected for short-term stability testing. The formulations have been detailed in Tables 42 and 43. The formulations were assessed with 25° C. and 40° C. storage conditions at t=0 and the subsequent timepoints. Formulations were assessed in 7 mL borosilicate vials. The following tests were performed:

Ruxolitinib phosphate content;

Ruxolitinib phosphate related substances;

Macroscopic appearance;

Microscopic appearance;

Apparent pH;

Instability index by LUMi Sizer;

Given the nature of the formulations for topical administration, the apparent pH of the formulations for short term stability are presented in Table 44. The other characterization data (e.g., ruxolitinib phosphate content, ruxolitinib phosphate related substances macroscopic appearance, microscopic appearance, and instability index by LUMi-Sizer) are not presented herein.

TABLE 42

| | Compositions (% w/w) of the recommended ruxolitinib phosphate formulations for short term stability and IVPT. | | | | |
|---|---|---|---|---|---|
| | Solution 1 | Solution 2 | Solution 3 | AG17 | EG09 |
| Excipient | SS33 | SS21 | SS34 | SS45 | SS37 |
| Ruxolitinib phosphate | 2.73 | 6.93 | 9.15 | 2.36 | 2.89 |
| Water | 15.50 | 14.72 | 14.37 | 55.94 | 36.60 |
| Propylene glycol | — | — | — | — | — |
| Glycerol | 20.00 | 18.99 | 18.54 | 19.34 | 19.25 |
| Polyethylene glycol 400 | 61.77 | 56.98 | 53.30 | — | — |
| Transcutol P | — | — | — | 19.34 | 19.25 |
| Diisopropyl Adipate | — | — | — | — | — |
| Polysorbate 80 | — | — | — | — | — |
| Polyoxyl 35 Castor Oil | — | — | — | — | — |
| Trolamine | — | 2.37 | 4.64 | 1.00 | 1.00 |
| Butylhydroxytoluene | — | — | — | — | — |
| Edetate disodium | — | — | — | 0.01 | 0.01 |
| Phenoxyethanol | — | — | — | 1.00 | 1.00 |
| Hydroxyethyl Cellulose (Natrasol 250 HHX) | — | — | — | 1.00 | — |
| Poloxamer 407 | — | — | — | — | 14.00 |
| Castor Oil | — | — | — | — | 6.00 |
| Total | 100.00 | 100.00 | 100.00 | 100.00 | 100.00 |
| Ruxolitinib freebase saturated solubility (% w/w) | 2.632 | 6.691 | 8.832 | 2.282 | 3.419 |
| Ruxolitinib freebase loading in intended formulation (% w/w) | 2.063 | 5.246 | 6.924 | 1.789 | 2.188 |
| Formulation Type | | Solution | | Emulsified Gel | |

TABLE 43

| | CR06* | CR10 2.93% | CR10 1.47% | OO04 | SUOO02 |
|---|---|---|---|---|---|
| Excipient | SS49 | SS37 | SS37 | SS11 | —— |
| Ruxolitinib phosphate | 1.54 | 2.93 | 1.47 | 0.528 | 1.982 |
| Water | 47.06 | 37.12 | 37.67 | — | — |
| Glycerol | — | 19.54 | 20.00 | 3.00 | — |
| Polyethylene glycol 400 | 5.00 | — | — | — | — |
| Transcutol P | 20.00 | 19.54 | 20.00 | 9.00 | — |
| Polyoxyl 35 Castor Oil | 4.00 | — | — | — | — |
| Trolamine | 2.50 | 1.00 | 1.00 | 1.00 | 1.00 |
| Butylhydroxytoluene | | | | 0.10 | — |
| Edetate disodium | 0.05 | 0.01 | 0.01 | — | — |
| Phenoxyethanol | 1.00 | 1.00 | 1.00 | — | — |
| Castor Oil | 2.00 | 2.00 | 2.00 | — | — |
| Isopropyl Myristate | 2.00 | 2.00 | 2.00 | — | — |
| Soybean Oil | 5.00 | 5.00 | 5.00 | — | — |
| Brij S721 | 1.66 | 1.66 | 1.66 | — | — |
| Brij S2 | 2.34 | 2.34 | 2.34 | — | — |
| Polowax | 5.85 | 5.85 | 5.85 | — | — |
| Medium chain triglycerides | — | — | — | 10.00 | 20.27 |
| Glycerol Monostearate (GMS II) | — | — | — | 5.00 | 5.00 |
| White soft paraffin | — | — | — | 51.37 | 51.75 |
| Novata BC PH | — | — | — | 20.00 | 20.00 |
| Total | 100.00 | 100.00 | 100.00 | 100.00 | 100.00 |
| Ruxolitinib freebase saturated solubility (% w/w) | 1.800 | 3.419 | 3.419 | 3.856 | 0.002** |
| Ruxolitinib freebase loading in intended formulation (% w/w) | 1.169 | 2.220 | 2.220 | 0.401 | 1.500 |
| Formulation Type | | O/W cream | | Oleaginous ointment | Oleaginous ointment (suspension) |

*Back up formulation.
**Based on solubility in medium chain triglycerides

Apparent pH

The apparent pH of the manufactured formulations was assessed at t=0 and the subsequent timepoints, following storage at 25 and 40° C. The results are presented in Error! Reference source not found.

At t=0, the apparent pH of the formulations ranged from 3.95-10.75, with the corresponding placebo formulations being 0.67-5.39 apparent pH units higher than active, which was as expected considering the addition of trolamine in the placebo formulations, in the absence of ruxolitinib phosphate. It should be noted that the apparent pH of the active formulation SU0002 was difficult to measure as a result of the formulation being a suspension, and a measurement was only achieved at the t=4 week timepoint at 40° C.

The lowest apparent pH was observed in the active formulations Solution 1, EG09 and CR10 2.93% (3.95, 4.51 and 4.54 apparent pH, respectively) which contained zero or low levels (1% w/w) of trolamine, and as expected, as the level of trolamine was increased in the Solutions (2.47 and 5% w/w trolamine in Solution 2 and 3, respectively), the apparent pH increased accordingly.

Following t=2 and 4 weeks storage at 25 and 40° C., there was no obvious change in apparent pH for any of the formulations assessed (formulations were within 0.48 apparent pH units from t=0).

TABLE 44

Apparent pH of formulations at t = 0 and the subsequent timepoints following storage at 25 and 40° C.

| | | Apparent pH | | | |
|---|---|---|---|---|---|
| | | 2 weeks | | 4 weeks | |
| Formulation | t = 0 | 25° C. | 40° C. | 25° C. | 40° C. |
| Solution 1 ACT | 3.95 | 3.86 | 3.81 | 3.91 | 3.85 |
| Solution 1 PBO | 7.93 | 8.41 | 7.91 | 8.14 | 7.67 |
| Solution 2 ACT | 5.08 | 5.14 | 5.01 | 5.09 | 5.07 |
| Solution 2 PBO | 10.47 | 10.37 | 10.19 | 10.33 | 10.24 |
| Solution 3 ACT | 7.20 | 7.07 | 7.15 | 7.19 | 7.18 |
| Solution 3 PBO | 10.75 | 10.63 | 10.49 | 10.62 | 10.57 |
| SUOO02 ACT | N/A* | N/A* | N/A* | N/A* | 6.54** |
| SUOO02 PBO | 9.00 | 8.53 | 9.11 | 8.65 | 8.81 |
| OO04 ACT | 8.26 | 8.26 | 8.09 | 8.21 | 8.32 |
| OO04 PBO | 8.93 | 8.91 | 8.79 | 8.71 | 8.85 |
| CR06 ACT | 8.24 | 8.19 | 8.16 | 8.19 | 8.21 |
| CR06 PBO | 9.66 | 9.59 | 9.44 | 9.53 | 9.36 |
| EG09 ACT | 4.51 | 4.51 | 4.44 | 4.59 | 4.51 |
| EG09 PBO | 9.19 | 9.11 | 9.10 | 9.34 | 8.94 |
| AG17 ACT | 6.28 | 6.25 | 6.24 | 6.21 | 6.30 |
| AG17PBO | 9.72 | 9.59 | 9.51 | 9.59 | 9.53 |
| CR10 1.47% w/w ACT | 7.33 | 7.30 | 7.23 | 7.53 | 7.36 |
| CR10 2.93% w/w ACT | 4.54 | 4.50 | 4.54 | 4.56 | 4.55 |
| CR10PBO | 9.46 | 9.34 | 9.31 | 9.44 | 9.20 |

Various modifications of the presently claimed subject matter, in addition to those described herein, will be apparent to those skilled in the art from the foregoing description. Such modifications are also intended to fall within the scope of the appended claims. Each reference cited in the present disclosure, including all patent, patent applications, and publications, is incorporated herein by reference in its entirety.

What is claimed is:

1. A topical formulation for treating a skin disease comprising a JAK 1/2 inhibitor, which is ruxolitinib, or a pharmaceutically acceptable salt thereof, and an organic amine pH adjusting agent.

2. The formulation of claim 1, wherein the organic amine pH adjusting agent is a tertiary amine or an alkanol amine.

3. The formulation of claim 1, wherein the JAK 1/2 inhibitor, or a pharmaceutically acceptable salt thereof, is ruxolitinib phosphate.

4. The formulation of claim 1, wherein the formulation comprises from about 0.05% to about 3.0% or about 0.05% to about 1.5% w/w of the ruxolitinib, or a pharmaceutically acceptable salt thereof, on a free base basis.

5. The formulation of claim 1, wherein the formulation is in a form chosen from a cream, a lotion, a foam or foamable formulation, a pump spray, an aqueous gel, a non-aqueous gel, and an emulsified gel.

6. The formulation of claim 1, wherein the formulation is an aqueous formulation.

7. The formulation of claim 1, further comprising one or more of water, an oil component, an emulsifier or stabilizer component, and a solvent component.

8. The formulation of claim 7, wherein the oil component comprises an emulsifier or stabilizer component or an emulsifier or wetting agent component.

9. The formulation of claim 1, further comprising one or more of a stabilizing agent and an antioxidant.

10. The formulation of claim 1, wherein the formulation has a pH from about 4.0 to about 8.0, from about 4.0 to about 7.0, from about 4.0 to about 6.0, about 5.0 to about 8.0, from about 5.5 to about 7.5, from about 5.5 to about 7.0, from about 5.5 to about 6.5, from about 5.0 to about 6.0, and at about 5.5.

11. The formulation of claim 1, wherein the amine pH adjusting agent is independently selected from trolamine, tris, ethanolamine, diethanolamine, ammonia, diisopropanolamine, 1-amino-2-propanol, 2-amino-2-ethyl-1,3-propanediol, 2-amino-2-methyl-1-propanol, diisopropylamine, imidazole, and pyridine.

12. The formulation of claim 11, wherein the amine pH adjusting agent is trolamine.

13. The formulation of claim 1, further comprising one or more pH adjusting agents, chelating agents, preservatives, co-solvents, penetration enhancers, humectants, thickening agents, gelling agents, viscosity building agents, surfactants, propellants, fragrances, colorants, and any combination thereof.

14. The formulation of claim 1, wherein the organic amine pH adjusting agent is trolamine and further comprising Transcutol P and glycerol.

15. The formulation of claim 1, wherein the organic amine pH adjusting agent is trolamine and further comprising ethanol and water.

16. The formulation of claim 1, wherein the form is a cream.

17. The formulation of claim 16, wherein the cream is an oil-in-water emulsion.

18. The formulation of claim 16, wherein the cream comprises water and an oil component.

19. The formulation of claim 16, wherein the cream comprises water, a solvent component, and an oil component.

20. The formulation of claim 19, wherein the oil component comprises an emulsifying or wetting agent component.

21. The formulation of claim 17, wherein the oil component comprises one or more stabilizing agents.

22. The formulation of claim 1, wherein the form is a lotion.

23. The formulation of claim 22, wherein the lotion formulation is an oil-in-water emulsion.

24. The formulation of claim 22, wherein the lotion formulation comprises water and an oil component.

25. The formulation of claim 22, wherein the lotion formulation comprises water, a solvent component, and an oil component.

26. The formulation of claim 25, wherein the oil component comprises an emulsifying or wetting agent component.

27. The formulation of claim 22, wherein the oil component comprises one or more stabilizing agents.

28. The formulation of claim 1, wherein the form is a foam or foamable formulation.

29. The formulation of claim 28, wherein the foam comprises a base component and a propellant component.

30. The formulation of claim 28, wherein the base component is an oil-in-water emulsion.

31. The formulation of claim 29, wherein the propellant component comprises one or more hydrofluorocarbons (HFCs) or hydrofluoroolefins (HFOs).

32. The formulation of claim 1, wherein the form is a spray.

33. The formulation of claim 32, wherein the spray comprises an aqueous spray formulation.

34. The formulation of claim 32, wherein the spray formulation comprises water, a solvent component, and a volatile excipient.

35. The formulation of claim 32, the spray formulation comprises water, a solvent component, a volatile excipient, and a film-forming component.

36. The formulation of claim 1, wherein the form is an aqueous gel.

37. The formulation of claim 36, wherein the aqueous gel comprises water, a solvent component, a stabilizing component, and a gelling agent component.

38. The formulation of claim 36, wherein the aqueous gel formulation comprises water, a solvent component, stabilizing component, a gelling agent component, and a preservative.

39. The formulation of claim 36, wherein the aqueous gel formulation comprises water, a solvent component, component stabilizing component, a gelling agent component, a preservative, and a chelating agent.

40. The formulation of claim 1, wherein the form is a non-aqueous gel formulation.

41. The formulation of claim 40, wherein the non-aqueous gel formulation comprises a solvent component.

42. The formulation of claim 40, wherein the non-aqueous gel formulation comprises a solvent component and a volatile excipient.

43. The formulation of claim 40, wherein the non-aqueous gel formulation comprises a solvent component, a volatile excipient, and a preservative.

44. The formulation of claim 40, wherein the non-aqueous gel formulation comprises a solvent component, a volatile excipient, a preservative, and a gelling component.

45. The formulation of claim 1, wherein the form is an emulsified gel formulation.

46. The formulation of claim 45, wherein the emulsified gel formulation comprises water, a solvent component, and an oil component.

47. The formulation of claim 46, wherein the oil component comprises an emulsifier component.

48. The formulation of claim 45, wherein the emulsified gel formulation comprises water, a solvent component, an oil component, an emulsifier component, and a chelating agent.

49. The formulation of claim 45, wherein the emulsified gel formulation comprises water, a solvent component, an oil component, an emulsifier component, a chelating agent, and a preservative component.

* * * * *